US012486259B2

(12) United States Patent
Ma et al.

(10) Patent No.: US 12,486,259 B2
(45) Date of Patent: Dec. 2, 2025

(54) FXR AGONIST HAVING PYRAZINE STRUCTURE, AND PREPARATION METHOD AND USE

(71) Applicant: JIANGSU TASLY DIYI PHARMACEUTICAL CO., LTD., Jiangsu (CN)

(72) Inventors: Weiwei Ma, Jiangsu (CN); Guocheng Wang, Jiangsu (CN)

(73) Assignee: JIANGSU TASLY DIYI PHARMACEUTICAL CO., LTD., Jiangsu (CN)

( * ) Notice: Subject to any disclaimer, the term of this patent is extended or adjusted under 35 U.S.C. 154(b) by 376 days.

(21) Appl. No.: 18/034,869

(22) PCT Filed: Dec. 29, 2020

(86) PCT No.: PCT/CN2020/140588

§ 371 (c)(1),
(2) Date: May 1, 2023

(87) PCT Pub. No.: WO2022/134146

PCT Pub. Date: Jun. 30, 2022

(65) Prior Publication Data

US 2023/0406846 A1 Dec. 21, 2023

(30) Foreign Application Priority Data

Dec. 22, 2020 (CN) ......................... 202011524465.9

(51) Int. Cl.
*C07D 413/12* (2006.01)
*A61P 1/16* (2006.01)
*C07D 413/14* (2006.01)

(52) U.S. Cl.
CPC .............. *C07D 413/12* (2013.01); *A61P 1/16* (2018.01); *C07D 413/14* (2013.01)

(58) Field of Classification Search
CPC ........ C07D 413/12; C07D 413/14; A61P 1/16
See application file for complete search history.

(56) References Cited

FOREIGN PATENT DOCUMENTS

| | | | |
|---|---|---|---|
| CN | 103702719 | A | 4/2014 |
| CN | 109071470 | A | 12/2018 |
| WO | WO 2011/020615 | A1 | 2/2011 |
| WO | WO 2013/007387 | A1 | 1/2013 |
| WO | WO 2013/037482 | A1 | 3/2013 |
| WO | WO 2017/201150 | A1 | 11/2017 |
| WO | WO 2020/033382 | A1 | 2/2020 |

OTHER PUBLICATIONS

Kinzel et al., Novel substituted isoxazole FXR agonists with cyclopropyl, hydroxycyclobutyl and hydroxyazetidinyl linkers: Understanding and improving key determinants of pharmacological properties, Aug. 1, 2016, Bioorganic & Medicinal Chemistry Letters, vol. 25 iss. 15, pp. 3746-3753. (Year: 2016).*

Haubertin et al., A Database of Historically-Observed Chemical Replacements, Jun. 1, 2007, Journal of Chemical Information and Modeling, vol. 47 iss. 4, pp. 1294-1302. (Year: 2007).*

International Patent Application No. PCT/CN2020/140588; Int'l Search Report; dated Sep. 24, 2021; 4 pages.

Kinzel et al.; "Novel substituted isoxazole FXR agonists with cyclopropyl, hydroxycyclobutyl and hydroxyazetidinyl linkers: Understanding and improving key determinants of pharmacological properties"; Bioorganic & Medicinal Chemistry Letters; vol. 26; Aug. 2016; p. 3746-3753 (abstract only).

* cited by examiner

*Primary Examiner* — Ali Soroush
(74) *Attorney, Agent, or Firm* — BakerHostetler

(57) ABSTRACT

The present invention relates to a novel FXR agonist having a pyrazine structure, a preparation method therefor and the use thereof, and in particular relates to a compound as represented by the following general formula (I), or a hydrate, a solvate or a pharmaceutically acceptable salt thereof or a resolved single isomer thereof, which has the effect of treating non-alcoholic fatty liver disease.

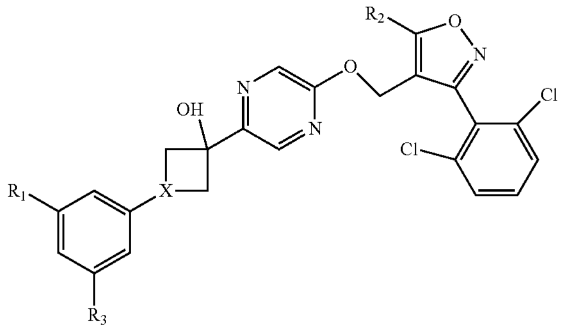

11 Claims, 11 Drawing Sheets

FXR AGONIST HAVING PYRAZINE STRUCTURE, AND PREPARATION METHOD AND USE

CROSS-REFERENCE TO RELATED APPLICATIONS

This application is the U.S. National Stage of International Application No. PCT/CN2020/140588, filed on Dec. 29, 2020, which claims priority to Chinese Patent Application No. 202011524465.9, filed on Dec. 22, 2020, the entire contents of both of which are incorporated herein by reference.

TECHNICAL FIELD

The present invention relates to a preparation method of pharmaceutical compounds, in particular to a novel FXR agonist having a pyrazine structure, and a preparation method therefor and a use thereof.

BACKGROUND ART

Since the discovery in 1999 that bile acids can activate farnesoid X nuclear receptor (FXR) to produce a variety of physiological functions, selective and highly active FXR agonists have been discovered. These FXR agonists can be classified into steroids and non-steroids by structure. The steroids are mainly chenodeoxycholic acid (CDCA, one of bile acids) and its derivatives and FXR agonist MFA-1 developed by Merck. The non-steroids include isoxazole compounds GW4064 and analogues thereof, Fexaramine compounds, azaindole compounds XL335 and derivatives thereof, benzimidazolyl amides, Pyrazolidine diketones and the like.

Nonalcoholic fatty liver disease (NAFLD) is a group of clinicopathological syndromes characterized by hepatic parenchymal cell steatosis and fat storage without a history of excessive alcohol consumption, and which the histological changes of the liver is similar to those of alcoholic liver disease, including simple fatty liver, and steatohepatitis and cirrhosis evolving from it. Nowadays, NAFLD has become the second chronic liver disease affecting human health after hepatitis B. Nonalcoholic steatohepatitis (NASH) is a chronic progressive liver disease caused by accumulation of fat in the liver, which can lead to cirrhosis, liver failure and hepatocellular carcinoma. Specifically, NASH is only a stage in the development of NAFLD.

Among the drugs under the studies of clinical trails, obeticholic acid is a FXR agonist, approved by FDA in May 2016 for the treatment of primary billiary cirrhosis (PBC), it is also the first NASH drug to enter the phase III clinical trail. The interim analysis of the pivotal phase III REGENERATE study of obeticholic acid in NASH patients with grade 2-3 liver fibrosis yielded positive results.

Other FXR agonists such as PX-104 has entered Phase II clinical trials with primary indication also being NAFLD.

6-ECDCA

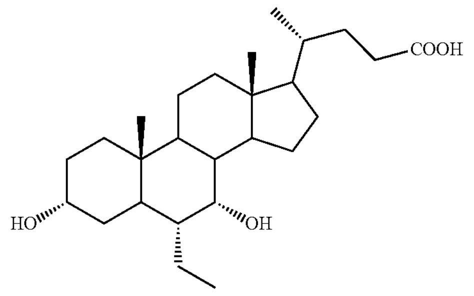

PX-104

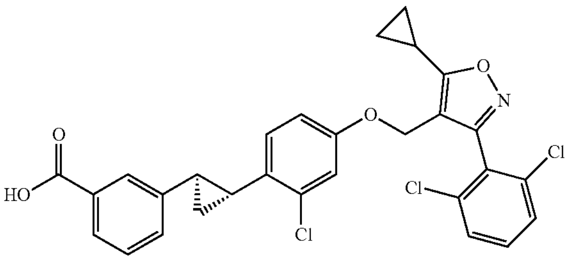

In 2000, Maloney etc. reported the first isoxazole FXR agonist GW4064 with high activity and selectivity. It's extracellular activity was $EC_{50}$=15 nmol·$L^{-1}$, and the $EC_{50}$ value was 90 nmol·$L^{-1}$ at the cellular level, which can completely activate the FXR target protein. However, in terms of pharmacokinetics, the oral availability at t½=3.5 h was only 10%, which did not meet the conditions of drug formation, so it is used as a tool compound for studying FXR function and related diseases. Subsequently, GSK, Novartis, Roche, Lilly, Phenex and other companies respectively modified the structure of GW4064 to obtain new compounds with higher activity, better oral availability and more drug-forming properties. Up to now, a large number of isoxazole compounds have been successfully synthesized, but they are deficient in terms of activity, water solubility, oral bioavailability, etc.

GW4064

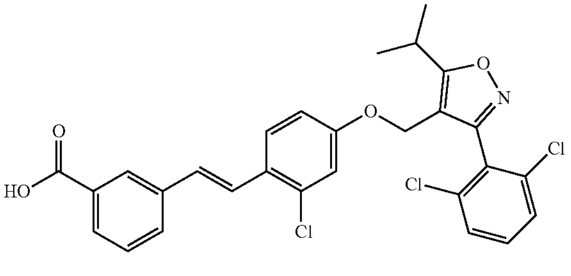

Chinese patent CN103702719A discloses novel FXR (NR1H4) binding and activity modulating compounds, and specifically discloses the following compounds:

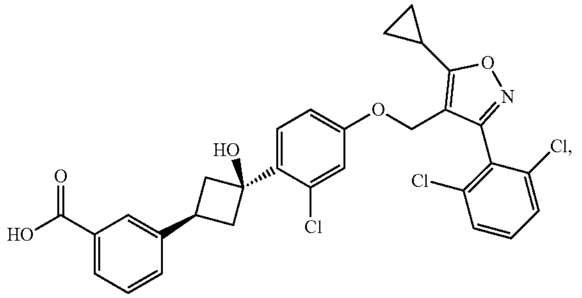

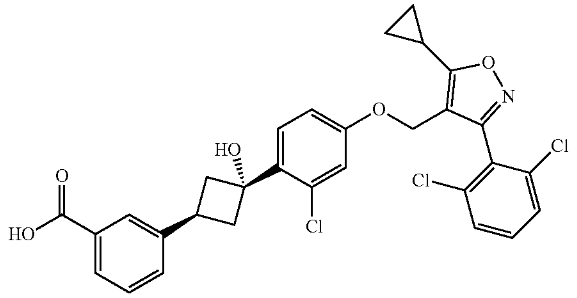

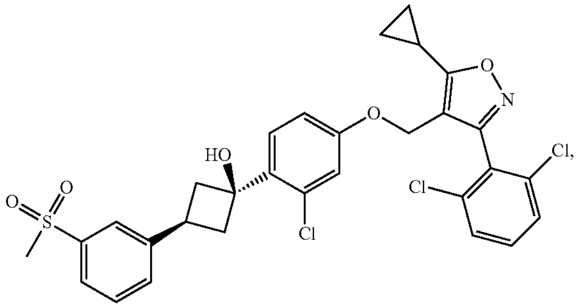

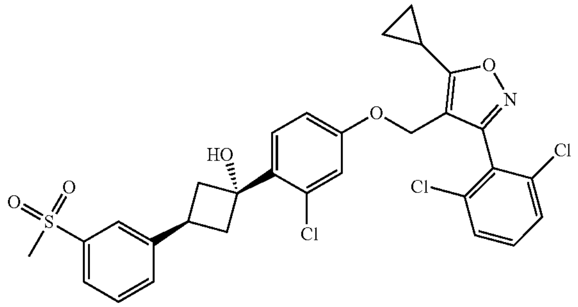

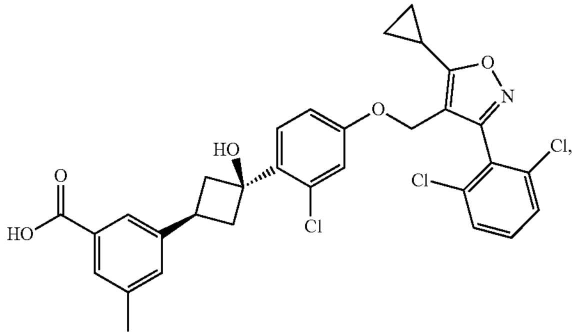

-continued

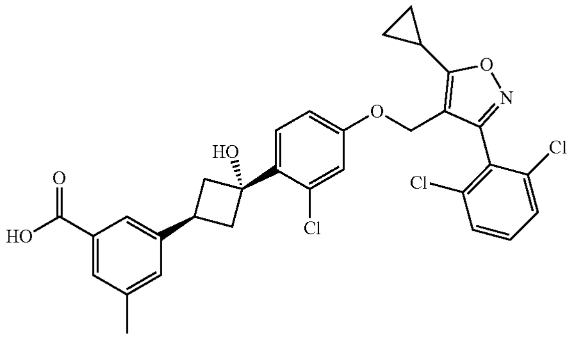

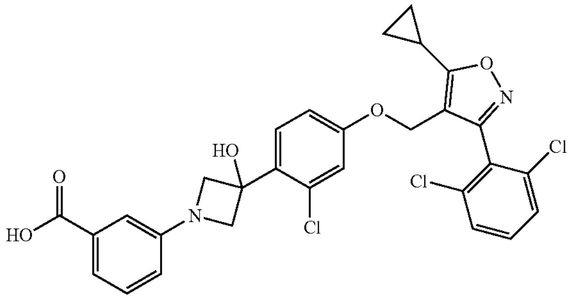

and the use of these compounds in the treatment of diseases such as NAFLD or NASH. These compounds are improved on the basis of compounds disclosed in WO2011/020615 by substituting the 1,3-cyclobutylene of the 1,2-cyclopropylidene or introducing a polar hydroxyl group to 1, 3-azocyclobutane. The results show that the resulting compounds retain activity at the FXR receptor and exhibit improved physicochemical properties, such as higher water solubility and/or membrane permeability. Better water solubility and membrane permeability result in higher oral bioavailability. However, these compounds have relatively lower activation activity at the FXR target.

SUMMARY OF THE INVENTION

In order to solve the above technical problems, the present invention provides a compound having the structure of Formula (I), or a hydrate, a solvate, a pharmaceutically acceptable salt or a resolved single isomer thereof:

Formula (I)

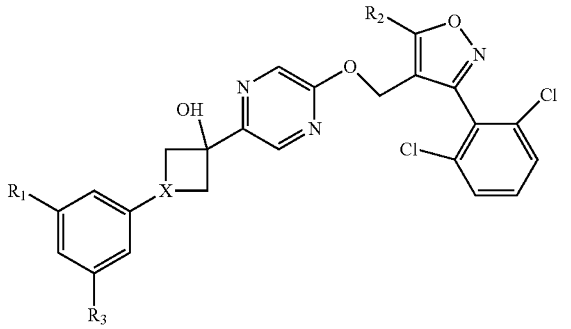

where $R_1$ is selected from of halogen, —COOH,

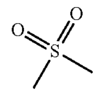 , or 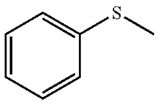 ;

$R_2$ is selected from $C_1$-$C_6$ alkyl, cyclic hydrocarbyl, aryl, substituted alkyl or substituted aryl;

$R_3$ is selected from —H or $C_1$-$C_3$ alkyl, cyclic hydrocarbyl, or substituted alkyl;

X is C or N.

Preferably, $R_1$ is selected from —Br;

$R_2$ is selected from $C_1$-$C_3$ alkyl or cyclic hydrocarbyl;

$R_3$ is selected from —$CH_3$;

X is C or N.

More preferably, $R_2$ is selected from

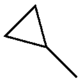 , 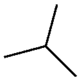 or 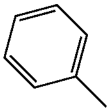 .

Most preferred compounds are selected from the group consisting of:

TM-1

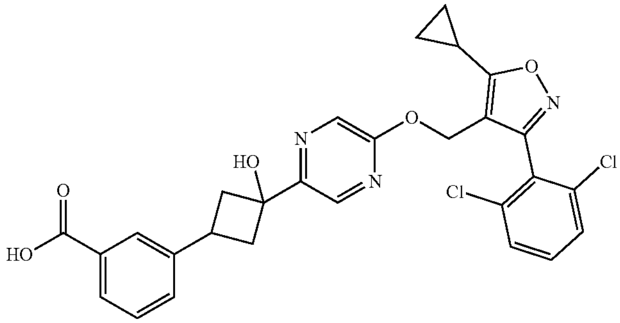 [SMILES: O=C(O)c1cccc(C2CC(O)(c3cnc(OCc4c(-c5c(Cl)cccc5Cl)noc4C4CC4)cn3)C2)c1]

Chemical Formula: $C_{28}H_{23}Cl_2N_3O_5$
Mass: 551.10
Molecular weight: 552.41

TM-2

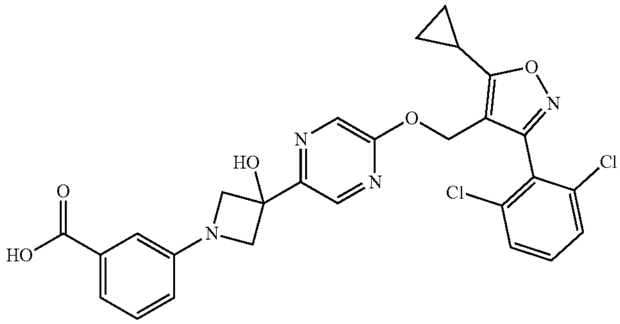 [SMILES: O=C(O)c1cccc(N2CC(O)(c3cnc(OCc4c(-c5c(Cl)cccc5Cl)noc4C4CC4)cn3)C2)c1]

Chemical Formula: $C_{27}H_{22}Cl_2N_4O_5$
Mass: 552.10
Molecular weight: 553.39

TM-3

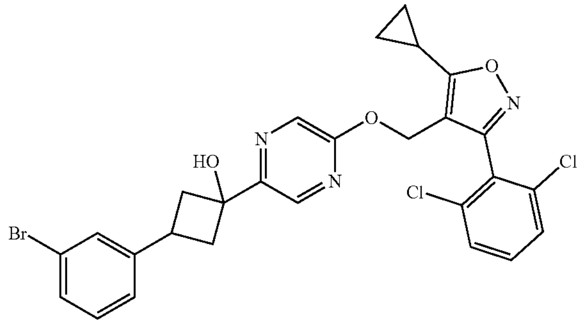 [SMILES: OC1(c2cnc(OCc3c(-c4c(Cl)cccc4Cl)noc3C3CC3)cn2)CC(c2cccc(Br)c2)C1]

Chemical Formula: $C_{27}H_{22}BrCl_2N_3O_3$
Mass: 585.02
Molecular weight: 587.29

-continued
TM-4
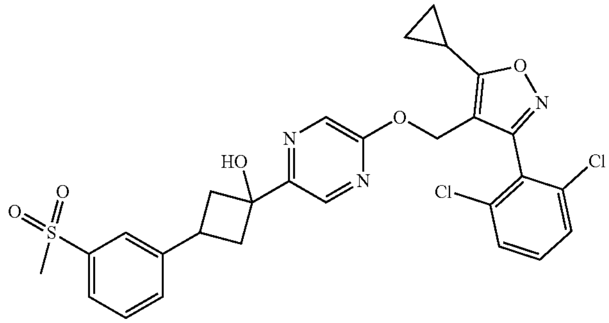 [SMILES: CS(=O)(=O)c1cccc(C2CC(O)(c3cnc(OCc4c(-c5c(Cl)cccc5Cl)noc4C4CC4)cn3)C2)c1]
Chemical Formula: $C_{28}H_{25}Cl_2N_3O_5S$
Mass: 585.1
Molecular weight: 586.49
TM-5
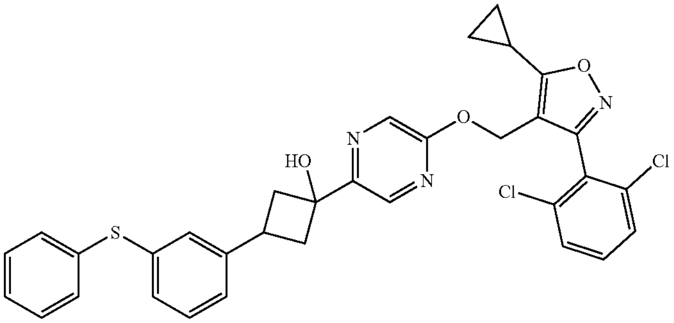 [SMILES: OC1(c2cnc(OCc3c(-c4c(Cl)cccc4Cl)noc3C3CC3)cn2)CC(c2cccc(Sc3ccccc3)c2)C1]
Chemical Formula: $C_{33}H_{27}Cl_2N_3O_3S$
Mass: 615.12
Molecular weight: 616.56
TM-6
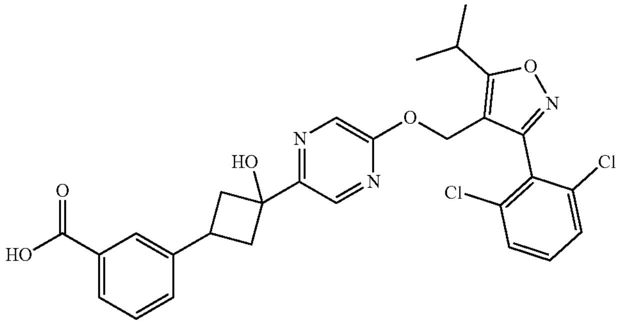 [SMILES: CC(C)c1onc(-c2c(Cl)cccc2Cl)c1COc1cnc(C2(O)CC(c3cccc(C(=O)O)c3)C2)cn1]
Chemical Formula: $C_{28}H_{25}Cl_2N_3O_5$
Mass: 553.12
Molecular weight: 554.42
TM-7
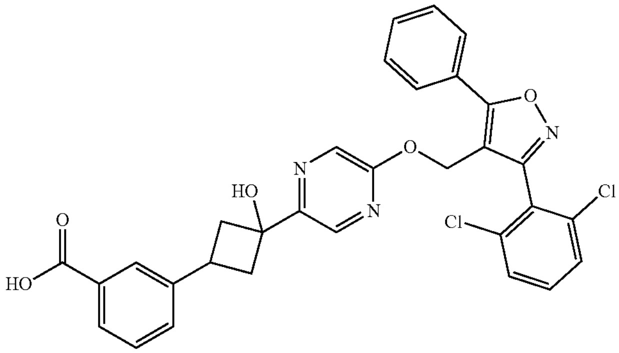 [SMILES: O=C(O)c1cccc(C2CC(O)(c3cnc(OCc4c(-c5c(Cl)cccc5Cl)noc4-c4ccccc4)cn3)C2)c1]
Chemical Formula: $C_{31}H_{23}Cl_2N_3O_5$
Mass: 587.10
Molecular weight: 588.44

-continued

TM-8

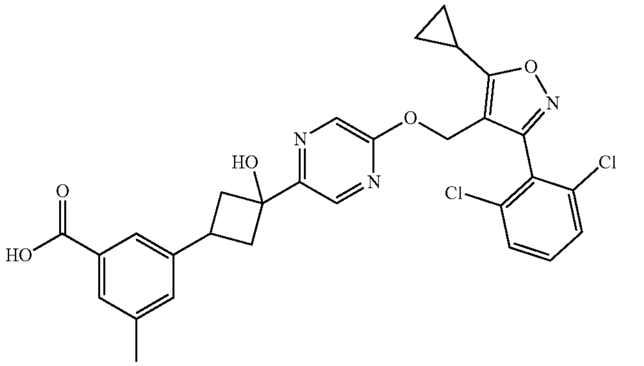 [SMILES: Cc1cc(C(=O)O)cc(C2CC(O)(c3cnc(OCc4c(-c5c(Cl)cccc5Cl)noc4C4CC4)cn3)C2)c1]

Chemical Formula: $C_{29}H_{25}Cl_2N_3O_5$
Mass: 565.12
Molecular weight: 566.44

TM-9

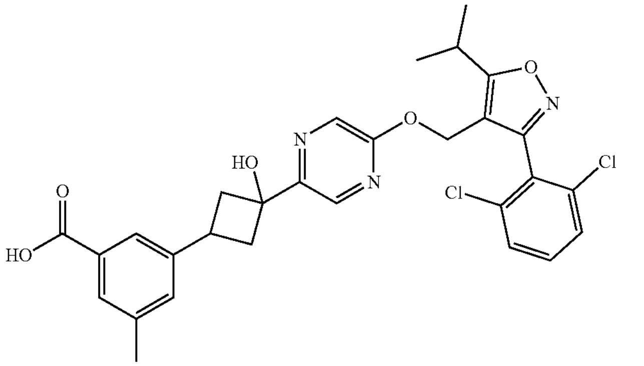 [SMILES: Cc1cc(C(=O)O)cc(C2CC(O)(c3cnc(OCc4c(-c5c(Cl)cccc5Cl)noc4C(C)C)cn3)C2)c1]

Chemical Formula: $C_{29}H_{27}Cl_2N_3O_5$
Mass: 567.13
Molecular weight: 568.45

TM-10

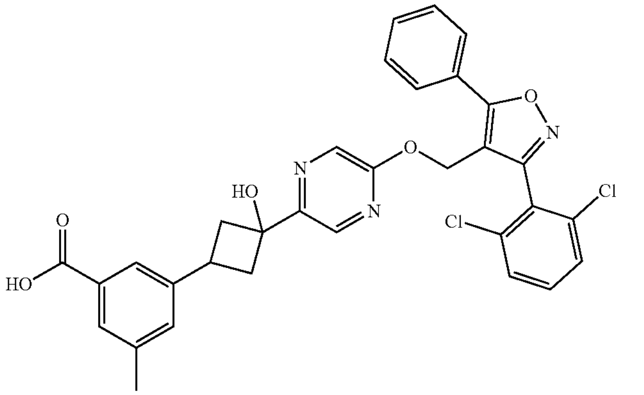 [SMILES: Cc1cc(C(=O)O)cc(C2CC(O)(c3cnc(OCc4c(-c5c(Cl)cccc5Cl)noc4-c4ccccc4)cn3)C2)c1]

Chemical Formula: $C_{32}H_{25}Cl_2N_3O_5$
Mass: 601.12
Molecular weight: 602.47

The present invention further provides a pharmaceutical composition comprising the compound as an active ingredient.

The pharmaceutical composition, if desired, may also contain a pharmaceutically acceptable carrier.

The present invention further provides a preparation method of the compound comprising the steps of:

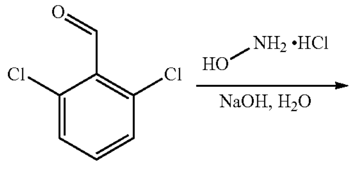

1a

-continued

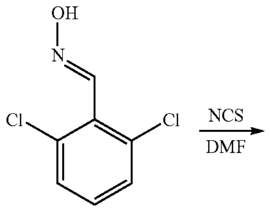

1b

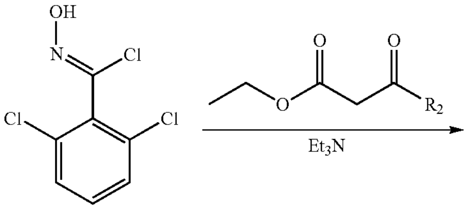

1c

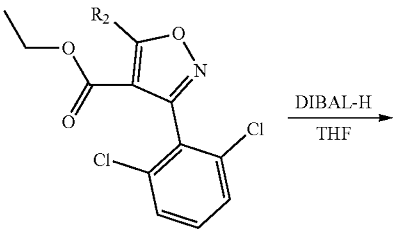

1d~1f

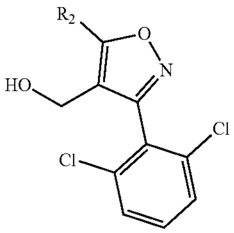

1-a~1-c

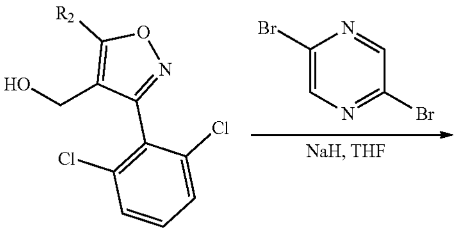

1-a~1-c

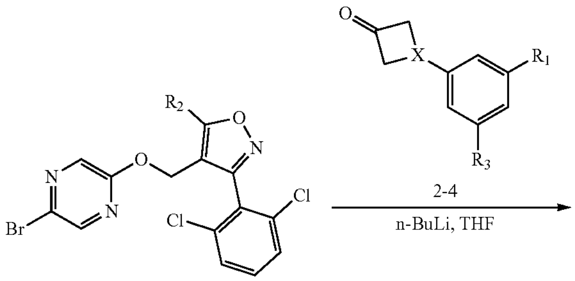

2-a~2-c

-continued

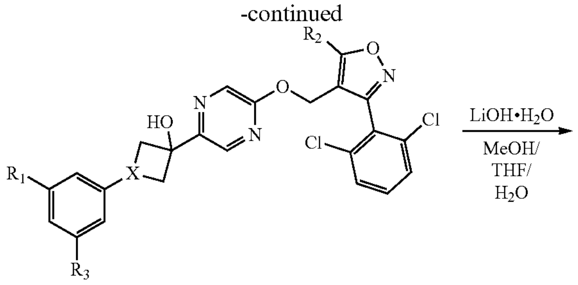

3-a~3-g

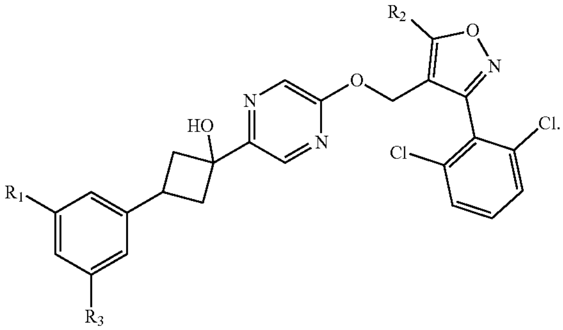

TM

A use of the compound according to the invention for the preparation of a medicament for the treatment of non-alcoholic fatty liver disease is provided.

The non-alcoholic fatty liver disease is non-alcoholic steatohepatitis.

The use of the pharmaceutical composition according to the invention is provided for preparation of a medicament for the treatment of non-alcoholic fatty liver disease, preferably non-alcoholic steatohepatitis.

The compound of the present invention includes all isomeric forms and isomeric mixtures thereof. It may also exist in the form of solvates.

The pharmaceutical composition of the invention, preferably in the form of a unit dose pharmaceutical formulation, may be formulated into any pharmaceutically acceptable dosage form selected from tablets, sugar-coated tablets, film-coated tablets, enteric-coated tablets, capsules, hard capsules, soft capsules, oral liquids, buccal preparations, granules, suspensions, solutions, injections, suppositories, ointments, plasters, creams, sprays, or patches. Oral formulation forms are preferred, with tablets or capsules being most preferred.

Such pharmaceutical formulations may be prepared using conventional techniques of formulation. The pharmaceutically acceptable carrier includes, but not limited to, mannitol, sorbitol, sorbic acid or potassium salts, sodium metabisulfite, sodium bisulfite, sodium thiosulfate, cysteine hydrochloride, thioglycolic acid, methionine, vitamin A, vitamin C, vitamin E, vitamin D, azone, disodium EDTA, calcium disodium edetate, carbonates of monovalent alkali metals, acetates, phosphates or aqueous solutions thereof, hydrochloric acid, acetic acid, sulfuric acid, phosphoric acid, amino acids, fumaric acid, sodium chloride, potassium chloride, sodium lactate, xylitol, maltose, glucose, fructose, dextran, glycine, starch, sucrose, lactose, silicon derivatives, cellulose and its derivatives, alginates, gelatin, polyvinylpyrrolidone, glycerol, propylene glycol, ethanol, tween 60-80, span-80, beeswax, lanolin, liquid paraffin, cetyl alcohol, gallates, agar, triethanolamine, basic amino acids, urea, allantoin, calcium carbonate, calcium bicarbonate, polyethylene glycol, cyclodextrins (such as beta-cyclodextrin), phospholipid materials, kaolin, talc, calcium stearate, magnesium stearate, and the like.

The pharmaceutical composition of the present invention, when formulated into a medicament, may contain 0.1-1000 mg of the pharmaceutically active substance of the present invention in the unit dosage, with the remainder being the pharmaceutically acceptable carrier. The pharmaceutically acceptable carrier may be 0.1-99.9% by weight of the total weight of the formulation.

The pharmaceutical composition of the present invention is used in an amount determined according to the patient's condition.

The preferred preparation method of the present invention comprises the following steps.

1) The synthesis method of isoxazole intermediates: benzaldehyde 1a is condensated with hydroxylamine hydrochloride under alkaline conditions to obtain benzaldehyde oxime 1b, which is subjected to NCS/DMF conditions to generate chlorobenzaldehyde oxime 1c followed by a 1,3-dipolar cycloaddition reaction with a keto ester to give trisubstituted isoxazole rings 1d-1f. DIBAL-H is added under the protection of nitrogen to reduce an ester bond to a hydroxyl group to obtain an intermediate 1-a-1-c.
2) Nucleophilic substitution of the isoxazole intermediate with dibromopyrazine under alkaline conditions provides the pyrazine intermediate 2-a-2-c; with the temperature kept at −78° C., lithium bromide exchange with n-butyllithium and carbon-carbon bond connection with the four-membered rings 2a-d give the terminal ester group product 3-a-3-g, and finally an ester hydrolysis reaction under alkaline conditions gives the target compound TM.

Advantageous Effects of the Invention. The compounds of the present invention, in particular TM-01 and TM-09, have a significant lowering effect on liver triglyceride and cholesterol levels, increase the liver weight and liver/body weight in mice, reduce pathological scores and collagen deposition in the liver, and have an improving effect on non-alcoholic fatty liver disease.

The compounds of the present invention have strong agonistic activity on the farnesoid X nuclear receptor, and show high permeability between cell membranes. They exhibit dose-dependent effect on fat-enriched liver weight in high-fat fed mouse model. It is predicted to show better use in the treatment of metabolic diseases such as obesity, diabetes and non-alcoholic fatty liver disease (NASH). The beneficial effects of the present invention are illustrated by the following experimental data.

Test Example I, Study of Agonistic Activity of the Compound of the Present Invention on FXR Receptor Experimental procedures: FXR (GST-labeled recombinant human FXR protein, manufacturer: Invitroren, Item number: PV4835) and SRC-1 (steroid receptor co-activator-1) are thawed on ice. Three solutions of ABC are prepared by a buffer solution, solution A, 0.4 n M FXR and 30 nM SRC-1; solution B, 10 ug/ml Acceptor Beads; solution C, 10 ug/ml Donor Beads. Solution A is added to the plate at 15 uL per well. It is incubated at room temperature for 1 hour. Solution B is added to the plate at 7.5 uL per well. It is incubated at room temperature for 1 hour. Solution C is added to the plate at 7.5 uL per well. It is incubated at room temperature for 1 hour. It is read from the microplate reader Envision. The data are curve fitted by using Prism 5.0 to calculate the $EC_{50}$. The results are shown in Table 1.

TABLE 1

| No. | Sample No. | Structural formula | $EC_{50}$ (μM) |
|---|---|---|---|
| 1 | TNT-747 | 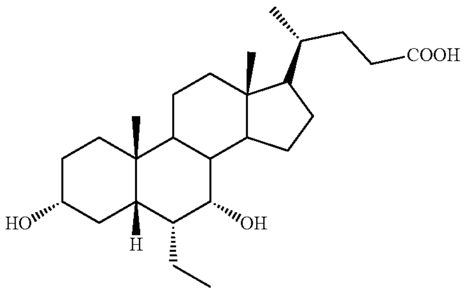 | 1.06 |
| 2 | GW4064 | 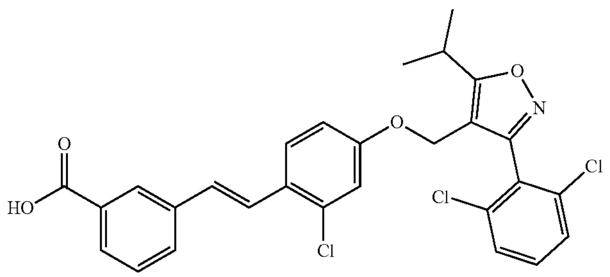 GW4064 | 0.23 |

TABLE 1-continued
| No. | Sample No. | Structural formula | $EC_{50}$ (μM) |
|---|---|---|---|
| 3 | M2 | 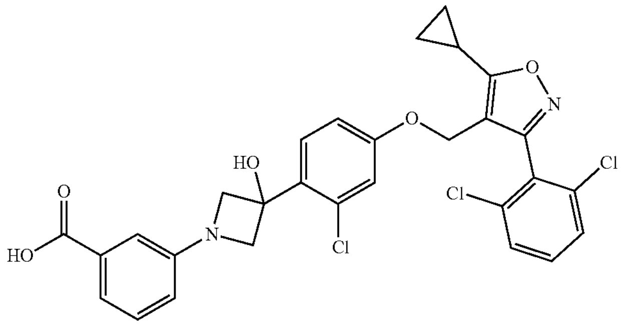 [SMILES: O=C(O)c1cccc(N2CC(O)(c3ccc(OCc4c(-c5c(Cl)cccc5Cl)noc4C4CC4)cc3Cl)C2)c1] | 1.80 |
| 4 | M3 | 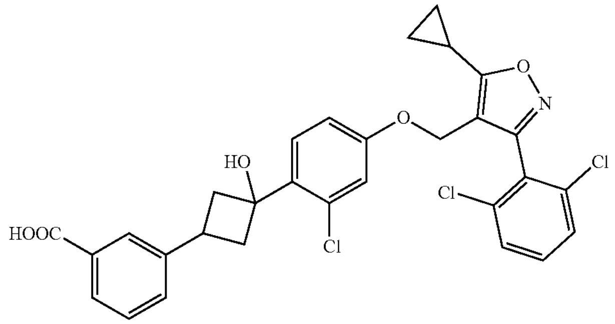 [SMILES: O=C(O)c1cccc(C2CC(O)(c3ccc(OCc4c(-c5c(Cl)cccc5Cl)noc4C4CC4)cc3Cl)C2)c1] | 1.09 |
| 5 | TM-01 | 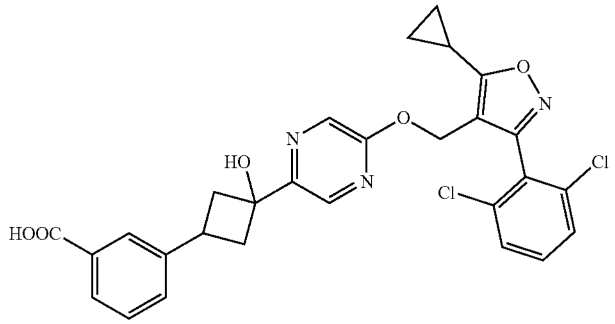 [SMILES: O=C(O)c1cccc(C2CC(O)(c3cnc(OCc4c(-c5c(Cl)cccc5Cl)noc4C4CC4)cn3)C2)c1] | 0.54 |
| 6 | TM-02 | 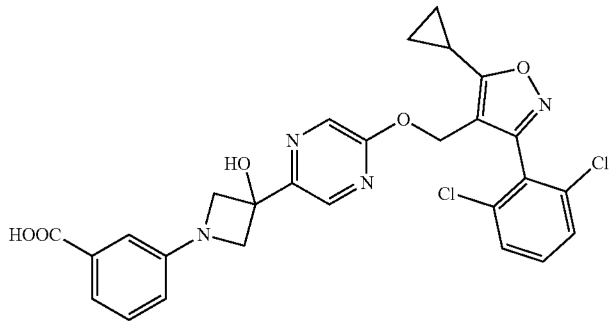 [SMILES: O=C(O)c1cccc(N2CC(O)(c3cnc(OCc4c(-c5c(Cl)cccc5Cl)noc4C4CC4)cn3)C2)c1] | 2.32 |

TABLE 1-continued
| No. | Sample No. | Structural formula | $EC_{50}$ (μM) |
|---|---|---|---|
| 7 | TM-03 | 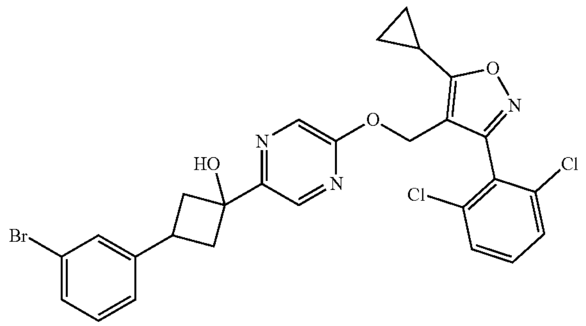 [SMILES: OC1(c2cnc(OCc3c(-c4c(Cl)cccc4Cl)noc3C3CC3)cn2)CC(c2cccc(Br)c2)C1] | 0.24 |
| 8 | TM-04 | 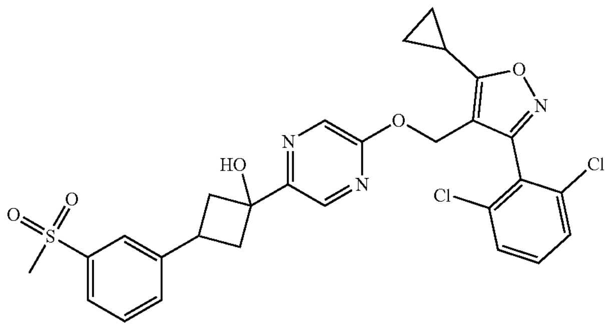 [SMILES: CS(=O)(=O)c1cccc(C2CC(O)(c3cnc(OCc4c(-c5c(Cl)cccc5Cl)noc4C4CC4)cn3)C2)c1] | 1.35 |
| 9 | TM-05 | 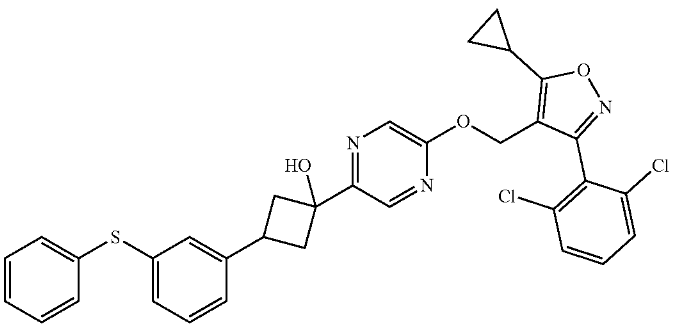 [SMILES: OC1(c2cnc(OCc3c(-c4c(Cl)cccc4Cl)noc3C3CC3)cn2)CC(c2cccc(Sc3ccccc3)c2)C1] | 5.01 |
| 10 | TM-06 | 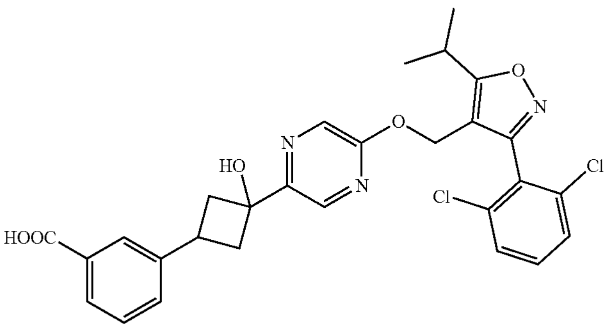 [SMILES: CC(C)c1onc(-c2c(Cl)cccc2Cl)c1COc1cnc(C2(O)CC(c3cccc(C(=O)O)c3)C2)cn1] | 2.41 |

TABLE 1-continued
| No. | Sample No. | Structural formula | $EC_{50}$ (μM) |
|---|---|---|---|
| 11 | TM-07 | 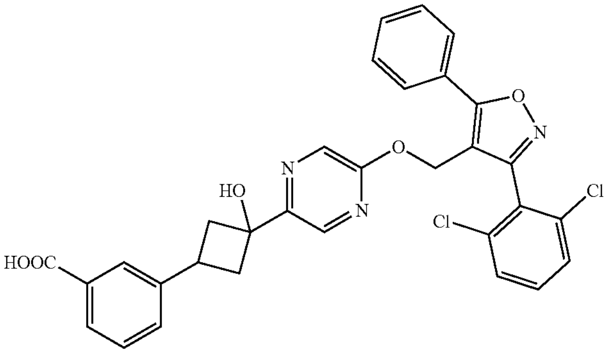 [SMILES: O=C(O)c1cccc(C2CC(O)(c3cnc(OCc4c(-c5c(Cl)cccc5Cl)noc4-c4ccccc4)cn3)C2)c1] | 4.21 |
| 12 | TM-08 | 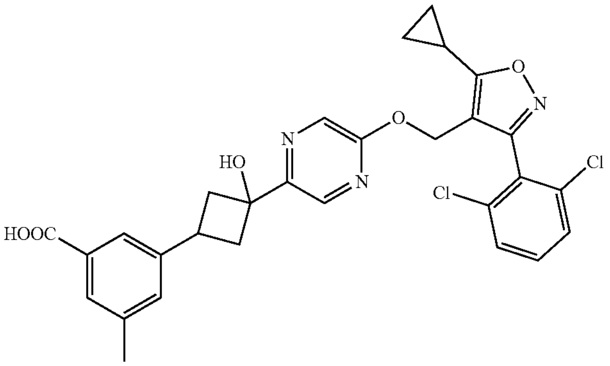 [SMILES: Cc1cc(C(=O)O)cc(C2CC(O)(c3cnc(OCc4c(-c5c(Cl)cccc5Cl)noc4C4CC4)cn3)C2)c1] | 0.24 |
| 13 | TM-09 | 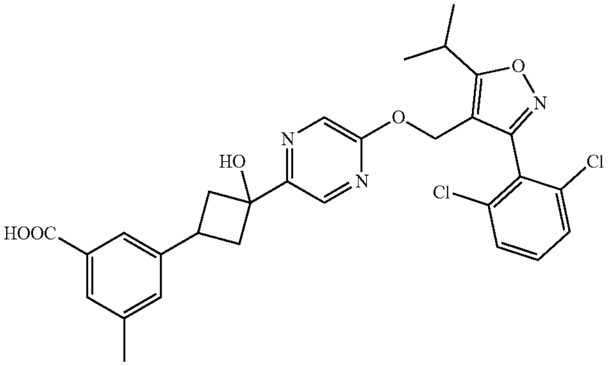 [SMILES: Cc1cc(C(=O)O)cc(C2CC(O)(c3cnc(OCc4c(-c5c(Cl)cccc5Cl)noc4C(C)C)cn3)C2)c1] | 0.48 |
| 14 | TM-10 | 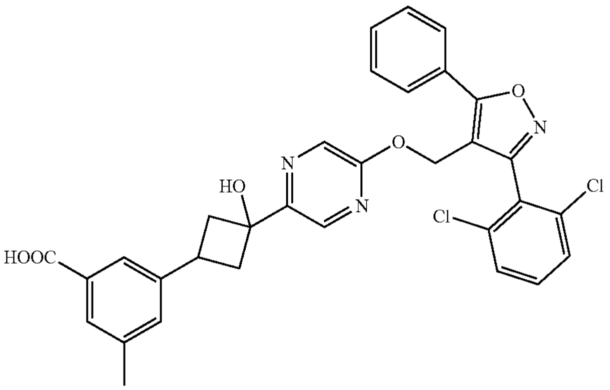 [SMILES: Cc1cc(C(=O)O)cc(C2CC(O)(c3cnc(OCc4c(-c5c(Cl)cccc5Cl)noc4-c4ccccc4)cn3)C2)c1] | 5.66 |

According to the sample activity results in Table 1, TM-05, TM-07 and TM-10 with poor activity were removed, and the other 7 samples were selected for intracellular FXR-TR-FRET experiment.

Test Example II, Intracellular FXR-TR-FRET Experiment

1. Cell culture: a, trypsinize dishes and seed cells are taken with appropriate density in 10 ml of complete trypsin at 37° C. b. Cells are incubated for 24 hours in 5% $CO_2$ and humidified.
2. Cell inoculation and transfection: FuGENE HD transfection reagent is used as a transfection reagent.
a. The transfection mixture is prepared according to the following procedure:

| | |
|---|---|
| Fusion expression vector (pBIND-FXR) | 25 ng/well |
| Mammalian cell two-hybrid system vector (pG5Luc) | 25 ng/well |
| Transfection reagent (FuGENE HD) | 0.15 μl/well |
| Non-fetal bovine serum medium (No FBS media) | 1.85 μl/well |
| Total mix | 2.5 μl/well |

b. The tube is tapped vigorously to mix the contents. The mixture is incubated at room temperature for 15 minutes.
c. Discs are trypsinized and cell density is determined.
d. The cytolymph is diluted to the desired volume at a density of 500,000 cells/ml (100 ul/well for 96-well plate).
e. The required volume of previously prepared transfection mixture is added to both cytolymph, and then 100 ul/well of cytolymph is dispensed onto the assay plate.
f. The assay plate is incubated under humidified conditions at 37° C., 5% $CO_2$ for 24 hours.
3. Compound preparation:
a. Compound stocks are prepared with a FXR working concentration of 10 mM and then diluted 3-fold in 100% DMSO.
b. 10 ul compound is added to 90 ul complete medium.
c. 5 ul compound solution is added to each well.
d. The plate is incubated at 37° C., 5% $CO_2$ and humidified for 18 hours.
4. Dual luciferase assay: the firefly and *Renilla* luciferase signals are analyzed by Dual Luciferase Reporter Assay System from Promega. Envision is used as a photometer.
5. Result calculation: data values are normalized by dividing the firefly signal by the *Renilla* signal. "F/R" means "firefly/*Renilla*". This normalization eliminates differences in different cell numbers and transfection efficiencies in each well. The % Activation value is calculated. The % Activation value is calculated by the following formula.

$$\%\ \text{Activation} = \left(\frac{X - \text{Min}}{\text{Max} - \text{Min}}\right) \times 100\%$$

X is the "F/R" value for each concentration point. The minimum value is the average "F/R" value for the no compound control. The maximum value is the average "F/R" value of the reference compound control.

6. The activity results are shown in Table 2.

TABLE 2

Activity results

| Sample No. | $EC_{50}$ (μM) |
|---|---|
| TM-01 | 1.28 |
| TM-02 | 3.14 |
| TM-03 | >5000 |
| TM-04 | >5000 |
| TM-06 | 1.79 |
| TM-08 | 1.51 |
| TM-09 | 0.26 |
| GW4064 | 0.30 |
| M3 | 1.49 |

The test compounds are investigated for their activity against FXR-TR-FRET and most of these compounds with pyrazine structure show better agonistic activity at the cellular level compared to the controls GW4064 and M3. Based on the results of the FXR-TR-FRET assay, TM-03 and TM-04 are removed and the remainder of the compound is subjected to the Caco-2 monolayer cell membrane transport experiment.

Test Example III, Caco-2 Monolayer Cell Membrane Transport Experiment

The bi-directional transport of target compounds from apical side (AP) to basolateral side (BL) and from BL side to AP side is studied by using human colon adenocarcinoma cell line Caco-2 monolayer model. The transport parameters, apparent permeability coefficient (Papp) and efflux ratio are calculated by quantitative analysis with high performance liquid chromatography (HPLC). Taking M3 as positive control and P-gp function substrate digoxin as reference, the five samples with higher intracellular activity are selected for the test to predict the in vivo oral bioavailability and the affinity with P-gp of the pyrazine isoxazole derivatives. The results are shown in Tables 3, 4 and 5.

TABLE 3

Apparent permeability coefficient of A-to-B in Caco-2 cell model

| Compounds | | Papp (10–6 cm/s) Sample-01 | Sample-02 | Average | Relative standard deviation (%) |
|---|---|---|---|---|---|
| Nadolol | A-B | 0.07 | 0.06 | 0.07 | 10.20 |
| | B-A | / | / | / | / |
| Metoprolol | A-B | 19.46 | 16.75 | 18.10 | 10.59 |
| | B-A | / | / | / | / |
| Digoxin | A-B | <0.05 | <0.04 | <0.04 | NA |
| | B-A | 11.74 | 11.52 | 11.63 | 1.37 |
| M3 | A-B | <0.16 | <0.14 | <0.15 | NA |
| | B-A | 13.31 | 9.96 | 11.63 | 20.38 |
| TM-01 | A-B | 6.42 | 9.91 | 8.17 | 0.30 |
| TM-02 | A-B | 8.57 | 9.47 | 9.02 | 0.07 |
| TM-06 | A-B | 7.86 | 6.48 | 7.17 | 0.13 |
| TM-08 | A-B | 1.01 | 0.94 | 0.97 | 0.07 |
| TM-09 | A-B | 8.46 | 9.05 | 8.75 | 0.05 |

TABLE 4

| Permeable membrane mass recovery rate in Caco-2 cell model | | | | | |
|---|---|---|---|---|---|
| | | Recovery rate % | | | Relative standard |
| Compounds | | Sample-01 | Sample-02 | Average | deviation (%) |
| Nadolol | A-B | 91.54 | 87.96 | 89.75 | 2.82 |
| | B-A | / | / | / | / |
| Metoprolol | A-B | 93.18 | 94.33 | 93.76 | 0.86 |
| | B-A | / | / | / | / |
| Digoxin | A-B | <85.23 | <88.72 | <86.97 | NA |
| | B-A | 93.73 | 95.44 | 94.59 | 1.28 |
| M3 | A-B | <27.17 | <16.42 | <21.80 | NA |
| | B-A | 36.33 | 35.57 | 35.95 | 1.50 |
| TM-01 | A-B | 63.92 | 78.51 | 71.21 | 0.14 |
| TM-02 | A-B | 64.86 | 76.84 | 70.85 | 0.12 |
| TM-06 | A-B | 81.02 | 67.31 | 74.17 | 0.13 |
| TM-08 | A-B | 99.57 | 98.50 | 99.04 | 0.01 |
| TM-09 | A-B | 80.89 | 81.99 | 81.44 | 0.01 |

TABLE 5

| Efflux rate in Caco-2 cell model | | | | | |
|---|---|---|---|---|---|
| | Caco-2 cell line (21 days) | | | | |
| Compounds | Papp (10−6 cm/s) A-B | Relative standard deviation (%) | Papp (10−6 cm/s) B-A | Relative standard deviation (%) | Efflux rate a |
| Nadolol | 0.07 | 10.20 | / | / | / |
| Metoprolol | 18.10 | 10.59 | / | / | / |
| Digoxin | <0.04 | NA | 11.63 | 1.4 | >262.93 |
| M3 | <0.15 | NA | 11.63 | 20.4 | >76.78 |
| TM-01 | 8.25 | 0.14 | 32.58 | 0.06 | 3.95 |
| TM-02 | 8.87 | 0.06 | 33.26 | 0.12 | 3.75 |
| TM-06 | 7.54 | 0.08 | 38.57 | 0.32 | 5.12 |
| TM-08 | 0.58 | 0.08 | 9.89 | 0.04 | 16.92 |
| TM-09 | 6.91 | 0.02 | 29.18 | 0.08 | 4.22 |

Note:
a Efflux rate = Papp B-A/Papp A-B

Experimental results are shown in Table 3, the A-to-B Papp values of the series of pyrazine-based isoxazole compounds of the present invention are higher than the P-gp's substrate digoxin (Papp A-to-B <0.04), and better than M3 (Papp A-to-B <0.15). In particular, the four compounds TM-01, TM-02, TM-06 and TM-09 with Papp, A-to-B values >2.5x10-6 cm/s, belong to highly permeable substrates. These data indicate that these pyrazine-based isoxazole compounds have good membrane penetration ability and are predicted to be superior to M3 for in vivo absorption.

The recovery rate of these pyrazine-based compounds after membrane permeation is shown in Table 4. The five compounds are evaluated for their bi-directional transport, with the results as shown in Table 5. It can be seen from the efflux rate that these derivatives greatly reduce the efflux compared with M3, and their efflux rates are far less than that of the control digoxin (efflux rate >262.93). The in vivo oral absorption is predicted to be improved accordingly.

According to the results of Test Example III, TM-08 with poor effect is removed, and other compounds are retained for animal experiments. Regarding the control group, M3 is excluded because of poor permeation. GW4064 is excluded as a tool molecule in previous studies due to its poor drug-forming property and low oral bioavailability. M2 is also used as a previous control compound and is excluded as less active than the compounds of the present invention in the first screening of protein level. Obeticholic acid is a drug currently in clinical study in the field of non-alcoholic fatty liver disease, and is proximate to be approved, so it is selected as the control substance for animal test.

Test Example IV: Pharmacodynamic Test of Methionine-Choline Deficient Diet (MCD) to Simulate Non-Alcoholic Fatty Liver Disease Obeticholic acid is a drug currently in clinical study in the field of non-alcoholic fatty liver disease, and is proximate to be approved, so it is selected as the control substance for animal test.

1. Experimental Animals

Animal strain: C57/BL6, Animal Grade: SPF Grade, Gender: male, Animal Age: 8 weeks old, Animals Received Date: 2018 Sep. 28, Animal Source: Shanghai Lingchang Biotechnology Co. Ltd., Animal Certificate No: SCXK (Shanghai)2013-0018 2013001836799, Mouse feeding Environment: temperature 20-26° C., humidity 40-70%, 12 hour day and night cycle.

2. Experimental Design and Method 2.1 Drug Preparation 2.1.1 Menstruum Preparation:

5% Solutol HS15/Normal saline: after Solutol HS15 (polyethylene glycol 15 hydroxystearate solubilizer) is dissolved in a water bath at 37° C., 5 ml of it is dissolved in 100 ml of normal saline, thoroughly stirred for later use.

2.1.2 Preparation of Administration Solution:

Obeticholic acid/5% Solutol HS15/Normal saline: 0.15 ml Solutol HS15 is added to accurately weighed 12 mg obeticholic acid to fully dissolve it, and 2.85 ml normal saline is added, vigorously mixed and dissolved by the ultrasound.

TM-01 Group/5% Solutol HS15/Normal saline: 2.5 ml of 6 mg/ml TM-01 suspension is taken, 2.5 ml of 5% Solutol HS15/normal saline is added, and the mixture is mixed well.

TM-02 Group/5% Solutol HS15/Normal saline: 2.5 ml of 6 mg/ml TM-02 suspension is taken, 2.5 ml of 5% Solutol HS15/normal saline is added, and the mixture is mixed well.

TM-06 Group/5% Solutol HS15/Normal saline: 2.5 ml of 6 mg/ml TM-06 suspension is taken, 2.5 ml of 5% Solutol HS15/Normal saline is added, and the mixture is mixed well.

TM-09 Group/5% Solutol HS15/Normal saline: 2.5 ml of 6 mg/ml TM-09 suspension is taken, 2.5 ml of 5% Solutol HS15/Normal saline is added, and the mixture is mixed well.

All drugs are freshly prepared prior to administration.

2.2 Route and Volume of Administration

Menstruum and test compounds are administered by gavage at a dose volume of 10 ml/kg;

2.3 Experimental Procedure, Grouping and Specific Administration Mode

After reaching the animal house, 70 8-week-old C57/BL6 mice are fed adaptively and randomly divided into 7 groups according to body weight after the average body weight reaches 23 g. They are given the model feed. The first group receives the control diet MCS and the remaining groups receive the MCD diet, while each group of mice receives compound treatment as follows:

Group 1. Control Group: MCS, menstruum, administered once daily by gavage;

Group 2. Model Group: MCD, menstruum, administered once daily by gavage;

Group 3. Obeticholic acid group: MCD, 40 mpk obeticholic acid, administered once daily by gavage;

Group 4. TM-01 Group: MCD, 30 mpk TM-01, administered once daily by gavage;

Group 5. TM-02 Group: MCD, 30 mpk TM-02, administered once daily by gavage;

Group 6. TM-06 Group: MCD, 30 mpk TM-06, administered once daily by gavage;

Group 7. TM-09 Group: MCD, 30 mpk TM-09, administered once daily by gavage;

2.4 Experimental Methods

Body weight and food intake are measured weekly during the experiment. Twenty-one days after administration, tail tips are bled with microcapillaries for AST, ALT measurements. Twenty-eight days after administration, mice are terminated, hearts are bled, and liver tissues are collected and weighed. One portion is snap frozen with liquid nitrogen for subsequent analysis and the other portion are fixed for pathological analysis.

2.4.1 Blood Index Determination

Mouse blood is centrifuged at 5000 rpm for 10 minutes and supernatants are collected for determination of TG (triglycerides), TC (total cholesterol), HDL (high density lipoprotein), LDL (low density lipoprotein), AST (aspartate aminotransferase) and ALT (alanine aminotransferase).

AST and ALT after administration for three and four weeks are determined according to the instructions of kit. The blood lipid index 4 weeks after administration is sent to Adicon Medical Laboratory Co. Ltd. for detection.

2.4.2 Determination of Blood Cytokines

Mouse blood is centrifuged at 5000 rpm for 10 minutes and the supernatant is collected for cytokine (mKC and MCP1) detection. Serum is stored at −80° C. prior to testing.

mKC and MCP1 assays are performed according to the kit instructions.

2.4.3 Assays of Liver TC and TG

The livers are removed from −80° C., homogenized in PBS (phosphate buffered saline), extracted with chloroform methanol organic phase, and subjected to TC and TG assays using the kit, normalized for protein content.

2.4.4 Tissue Collection

Four weeks after administration, the mice are anesthetized. The heart is bled, the liver is isolated and weighed. The right lobe is snapfrozen with liquid nitrogen and stored at −80° C. for liver lipid analysis. The left lobe is isolated and fixed in 10% formalin for subsequent HE and Sirius Red staining.

2.5 Result Processing and Data Analysis

Test results are expressed as Mean±SEM and significance analysis is performed using T-Test. * indicates a significant difference at $p<0.05$, * * indicates a strong significant difference at $p<0.01$, and * * * indicates a very significant difference at $p<0.001$ compared to the model group.

3 Test Results and Data Analysis 3.1 Effect of Compounds on Body Weight and Food Intake in Mice Mice fed with MCD show a significant decrease in body weight as expected. Body weight is also decreased continuously over time. Each experimental group treated with the compounds also has a slight decrease in body weight compared to the model group (Table 6).

TABLE 6

Effect of compounds on body weight of mice

| | Weight (g) | | | | |
|---|---|---|---|---|---|
| Group | 0 week | 1 week | 2 weeks | 3 weeks | 4 week |
| Group 1-control | 23.75 ± 0.30 | 23.64 ± 0.26 | 23.62 ± 0.30 | 25.13 ± 0.34 | 25.73 ± 0.33 |
| Group 2-model + vehicle | 23.59 ± 0.27 | 21.27 ± 0.24 | 19.09 ± 0.28 | 18.21 ± 0.21 | 16.97 ± 0.27 |
| Group 3-obeticholic acid | 23.72 ± 0.46 | 21.28 ± 0.42 | 18.97 ± 0.41 | 17.60 ± 0.35 | 15.72 ± 0.35 |
| Group 4-TM-01 30 mpk | 23.78 ± 0.47 | 21.24 ± 0.42 | 18.49 ± 0.41 | 16.97 ± 0.38 | 14.70 ± 0.20 |
| Group 5-TM-02 30 mpk | 23.71 ± 0.35 | 21.52 ± 0.42 | 18.81 ± 0.49 | 16.69 ± 0.34 | 15.48 ± 0.35 |
| Group 6-TM-06 30 mpk | 23.75 ± 0.27 | 21.36 ± 0.27 | 18.29 ± 0.28 | 16.41 ± 0.25 | 15.70 ± 0.22 |
| Group 7-TM-09 30 mpk | 23.60 ± 0.29 | 21.26 ± 0.34 | 19.29 ± 0.39 | 17.18 ± 0.31 | 15.90 ± 0.31 |

TABLE 7

Effect of compounds on food intake in mice

| | Food intake (g) | | | |
|---|---|---|---|---|
| Group | 1 week | 2 weeks | 3 weeks | 4 weeks |
| Group 1-control | 2.472 ± 0.018 | 2.429 ± 0.139 | 2.940 ± 0.014 | 2.316 ± 0.458 |
| Group 2-model + vehicle | 2.378 ± 0.116 | 2.572 ± 0.188 | 1.934 ± 0.150 | 1.881 ± 0.347 |
| Group 3-obeticholic acid | 2.992 ± 0.396 | 2.945 ± 0.315 | 2.092 ± 0.320 | 2.073 ± 0.031 |
| Group 4-TM-01 30 mpk | 3.011 ± 0.555 | 2.746 ± 0.466 | 1.909 ± 0.215 | 1.697 ± 0.027 |
| Group 5-TM-02 30 mpk | 2.190 ± 0.504 | 2.400 ± 0.288 | 1.688 ± 0.266 | 1.518 ± 0.376 |

TABLE 7-continued

| Effect of compounds on food intake in mice | | | | |
|---|---|---|---|---|
| | Food intake (g) | | | |
| Group | 1 week | 2 weeks | 3 weeks | 4 weeks |
| Group 6-TM-06 30 mpk | 2.356 ± 0.213 | 2.664 ± 0.194 | 2.093 ± 0.250 | 1.932 ± 0.137 |
| Group 7-TM-09 30 mpk | 2.364 ± 0.186 | 2.707 ± 0.187 | 2.284 ± 0.342 | 2.109 ± 0.661 |

3.2 Effect of Compounds on Blood Indices

Three weeks after MCD and compounds treatment, tail tip bleeds are taken for AST and ALT assays. The results show that ALT in the model group is increased about 3-fold and AST is increased more than 2-fold compared to the control group. The obeticholic acid group results in higher levels of AST and ALT than the model group. ALT and AST are significantly reduced in the TM-41, TM-06 and TM-09 groups compared to the model group, with the TM-02 group showing the same way as the obeticholic acid group. (Table 8)

After 4 weeks of MCD and compounds treatment, blood lipid levels are slightly higher in the model group than in the control group. The obeticholic acid treatment reduces cholesterol levels in the blood. Groups TM-01, TM-02, TM-06 and TM-09 have different reductions in blood lipids (Table 9).

TABLE 8

| Change in AST and ALT after 3 and 4 weeks of compounds treatment | | | | |
|---|---|---|---|---|
| | ALT (U/L) | | AST (U/L) | |
| Group | 3 weeks | 4 weeks | 3 weeks | 4 weeks |
| Group 1-control | 5.64 ± 0.29** | 10.24 ± 2.27** | 25.54 ± 1.14*** | 36.24 ± 2.27** |
| Group 2-model + vehicle | 60.80 ± 9.73 | 18.66 ± 1.30 | 74.04 ± 10.45 | 67.27 ± 10.16 |
| Group 3-obeticholic acid | 323.00 ± 37.79*** | 93.37 ± 10.36*** | 197.24 ± 21.54*** | 126.59 ± 20.25*** |
| Group 4-TM-01 30 mpk | 41.58 ± 10.32 | 14.28 ± 13.21** | 53.50 ± 19.62 | 40.36 ± 26.31* |
| Group 5-TM-02 30 mpk | 183.36 ± 29.85*** | 90.68 ± 42.13*** | 113.46 ± 13.79** | 83.24 ± 12.08 |
| Group 6-TM-06 30 mpk | 48.97 ± 26.07 | 49.13 ± 33.04 | 52.14 ± 18.73 | 45.23 ± 13.21* |
| Group 7-TM-09 30 mpk | 40.27 ± 21.48* | 14.30 ± 4.19* | 45.04 ± 12.08* | 38.40 ± 4.19* |

TABLE 9

| Changes in blood lipid levels after 4 weeks of compounds treatment | | | | |
|---|---|---|---|---|
| Group | TG (mmol/L) | TC (mmol/L) | LDL (mmol/L) | HDL (mmol/L) |
| Group 1-control | 0.52 ± 0.10* | 0.77 ± 0.09*** | 2.05 ± 0.06*** | 0.34 ± 0.03** |
| Group 2-model + vehicle | 0.60 ± 0.03 | 1.12 ± 0.08 | 2.90 ± 0.04 | 0.60 ± 0.01 |
| Group 3-obeticholic acid | 0.56 ± 0.02 | 0.86 ± 0.04** | 2.80 ± 0.03 | 0.55 ± 0.01** |
| Group 4-TM-01: 30 mpk | 0.53 ± 0.10 | 0.95 ± 0.44* | 2.61 ± 0.26* | 0.59 ± 0.11 |
| Group 5-TM-02 30 mpk | 0.57 ± 0.06 | 1.25 ± 0.14 | 2.93 ± 0.12 | 0.61 ± 0.02* |
| Group 6-TM-06 30 mpk | 0.59 ± 0.02 | 0.97 ± 0.16 | 3.01 ± 0.09* | 0.42 ± 0.06*** |
| Group 7-TM-09 30 mpk | 0.54 ± 0.04* | 0.86 ± 0.09* | 2.52 ± 0.07** | 0.56 ± 0.02* |

3.3 Effect of Compounds on Liver Fat Content

After 4 weeks of MCD and compounds treatment, livers are collected for lipid assays, and liver lipid content is homogenized with protein. Liver triglycerides and cholesterol are significantly higher in the model group than in the control group. Both of these indicators are decreased slightly after obeticholic acid treatment. The groups TM-01, TM-02, TM-06 and TM-09 have different lowering effects on liver triglyceride (liver TC) and total cholesterol content (liver TG), with the TM-01 and TM-09 groups showing significant lowering levels. (Table 10)

TABLE 10

| Hepatic lipid content change after compounds treatment | | |
|---|---|---|
| Group | liver TG (mol/g protein) | liver TC (mol/g protein) |
| Group 1-control | 112.55 ± 8.59*** | 21.47 ± 1.29*** |
| Group 2-model + vehicle | 339.42 ± 40.24 | 44.94 ± 5.50 |
| Group 3-obeticholic acid | 298.46 ± 36.25 | 35.7 ± 3.38 |
| Group 4-TM-01: 30 mpk | 246.69 ± 54.09* | 34.85 ± 8.20 |
| Group 5-TM-02 30 mpk | 307.38 ± 26.30 | 41.67 ± 5.73 |
| Group 6-TM-06 30 mpk | 303.5 ± 46.52 | 38.2 ± 35.04 |
| Group 7-TM-09 30 mpk | 231.73 ± 18.4* | 37.67 ± 3.65* |

3.4 Effect of Compounds on Body Weight of Mice

After 4 weeks of MCD and compounds treatment, livers are collected and weighed. The liver weight and liver-to-body weight ratio of mice in model group are significantly lower than those in control group. When analyzing the results, it is unexpectedly found that such compounds have a significant effect on liver weight. Each of TM-01, TM-02, TM-06 and TM-09 significantly increases mouse liver weight and liver/body weight. (Table 11)

TABLE 11

| Effect of compounds treatment on liver weight | | |
|---|---|---|
| | Effect of compounds treatment on liver weight | |
| Group | liver weight(g) | liver/body weight(%) |
| Group 1-control | 0.98 ± 0.02** | 3.79 ± 0.05* |
| Group 2-model + vehicle | 0.51 ± 0.01 | 3.02 ± 0.05 |
| Group 3-obeticholic acid | 0.90 ± 0.03*** | 5.76 ± 0.26*** |
| Group 4-TM-01 30 mpk | 0.89 ± 0.05*** | 6.32 ± 0.26*** |
| Group 5-TM-02 30 mpk | 0.85 ± 0.05*** | 5.48 ± 0.28*** |
| Group 6-TM-06 30 mpk | 0.67 ± 0.03*** | 4.23 ± 0.13*** |
| Group 7-TM-09 30 mpk | 0.74 ± 0.04*** | 4.98 ± 0.25*** |

3.5 Effect of Compounds on Liver Pathology

After liver fixed, HE and Sirius Red staining is performed. After staining is completed, the scanning is performed for the whole film. Six 20× fields are randomly selected. Pathological scoring (i.e. HE score) is performed on a combination of six 20× fields stained with HE. Pathological scoring criteria are shown in Table 12. Six 20× field images stained with Sirius Red are used to calculate the ratio of positively stained area by Sirius Red to total area (i.e., Sirius red staining area) by using Image J.

TABLE 12

| Pathology scoring criteria | | |
|---|---|---|
| Pathological manifestation | Standard | Scoring |
| Hepatocyte | None | 0 |
| balloon | Small number of cells | 1 |
| degeneration | Many cells | 2 |
| Inflammation | No inflammatory foci | 0 |
| of liver lobule | Less than 2 inflammatory foci per 200x field | 1 |
| | 2-4 inflammatory foci per 200x field | 2 |
| | More than 4 inflammatory foci per 200x field | 3 |
| Steatosis | Less than 5% | 0 |
| | 5%-33% | 1 |
| | Greater than 33% to 66% | 2 |
| | Greater than 66% | 3 |

After fed with MCD for 4 weeks, there are accumulation of adipocytes and occasionally infiltration of inflammatory cells in liver. Adipocytes accumulation and inflammatory cells infiltration are more significant after treatment with obeticholic acid. Pathological scoring shows that after MCD feeding, the pathological score of model group is about 2. The score of obeticholic acid treatment is increased, while the pathological condition is relieved after compounds treatment (Table 13).

TABLE 13

| Pathology scoring results | | |
|---|---|---|
| | Effect of hepatic pathological changes after compounds treatment | |
| Group | HE score | Sirius red staining area (%) |
| Group 1-control | 0 | 0.232 ± 0.023*** |
| Group 2-model + vehicle | 2 | 0.559 ± 0.051 |
| Group 3-obeticholic acid | 2.6 | 0.344 ± 0.057 |
| Group 4-TM-01 30 mpk | 1 | 0.365 ± 0.069** |
| Group 5-TM-02 30 mpk | 1.4 | 0.398 ± 0.030 |
| Group 6-TM-06 30 mpk | 1.6 | 0.421 ± 0.081 |
| Group 7-TM-09 30 mpk | 1.1 | 0.392 ± 0.057** |

3.4 Conclusion.

After 4 weeks of MCD feeding, AST, ALT and lipids in blood are induced to increase, which promotes the accumulation of fat in the liver and the generation of inflammatory foci. The model had the characteristics of non-alcoholic fatty liver disease.

The compounds provided by the present invention, especially TM-01 and TM-09, have a significant lowering effect on liver triglyceride and cholesterol levels, increase the liver weight and liver/body weight in mice, and reduce pathological scoring and collagen deposition in liver to some extent. They are preliminarily judged to have an improving effect on the non-alcoholic fatty liver disease in animals.

DETAILED DESCRIPTION

Figure 1:
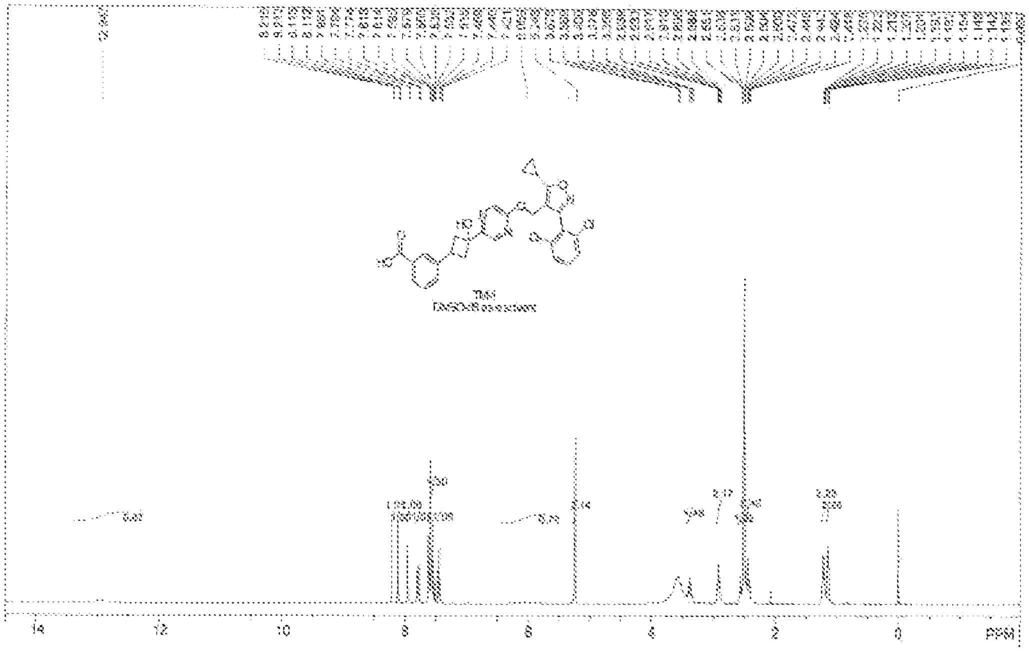
FIG. 1 is the $^1$H-NMR spectrogram of compound TM-1 of the present invention.

The present invention is explained in detail below in conjunction with specific embodiments. Those skilled in the art can more fully understand the present patent. The specific embodiments are merely illustrative of the technical solutions of the present invention and do not limit the invention in any way.

1. The synthetic route for the (3-(2, 6-dichlorophenyl)-4-hydroxymethyl-5-cyclopropylisoxazole) intermediate is as follows:

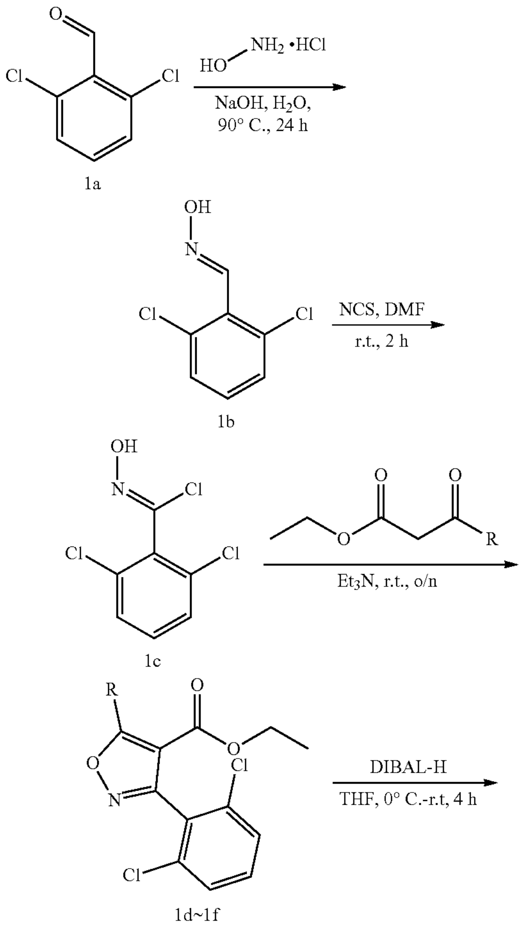

1a

1b

1c

1d~1f

-continued

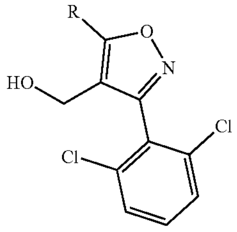

1-a~1-c

The synthesis method is as follows:

Synthesis of 2, 6-dichlorobenzaldehyde oxime

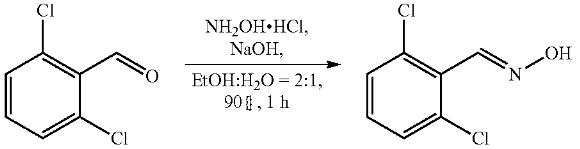

1a

1b

Hydroxylamine hydrochloride (11 g, 1 eq) and sodium hydroxide (6.3 g, 1.2 eq) were dissolved in water. A solution of 2, 6-dichlorobenzaldehyde (25 g, 0.14 mmol, 1.2 eq) in ethanol (200 mL) was added at room temperature. The mixture was stirred at 90° C. for 1 h. After cooling to room temperature, the ethanol was distilled off under reduced pressure. After the suction filtration, the filter cake is washed by water (2×100 mL). After drying, a white solid (2, 6-dichlorobenzaldehyde oxime) 9.46 g was obtained in 84% yield.

1.2 Synthesis of 2, 6-dichloro-N-hydroxy-chlorobenzaldehyde oxime

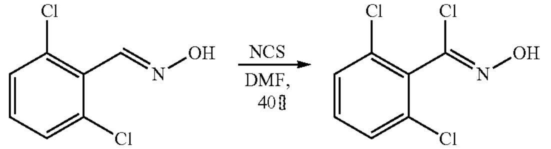

1b

1c

A solution of N-chlorosuccinimide (16.08 g, 0.12 mol, 1 eq) in DMF (90 mL) was slowly added dropwise to a solution of 2, 6-dichlorobenzaldehyde oxime (22.8 g, 0.12 mol, 1 eq) in DMF (90 mL) at 40° C., stirred and monitored by TLC. After the reaction, the mixture was cooled to room temperature, poured into ice water (200 mL), extracted three times with methyl tert-butyl ether (3×100 mL). The organic phase was combined, and then washed with water (3×100 mL) and saturated salt solution (100 mL). After drying the ester layer with anhydrous sodium sulfate, suction filtration was performed, and the organic solvent was distilled off under reduced pressure to obtain the crude product as a yellow oil, which was separated and purified by silica gel column chromatography with gradient elution (PE:EA=5:1, v/v) to give a white solid (2,6-dichloro-N-hydroxy-chlorobenzaldehyde oxime) 26 g, yield 97%.

1.3 Synthesis of 3-(2, 6-dichlorophenyl)-5-cyclopropylisoxazole-4-methyl formate

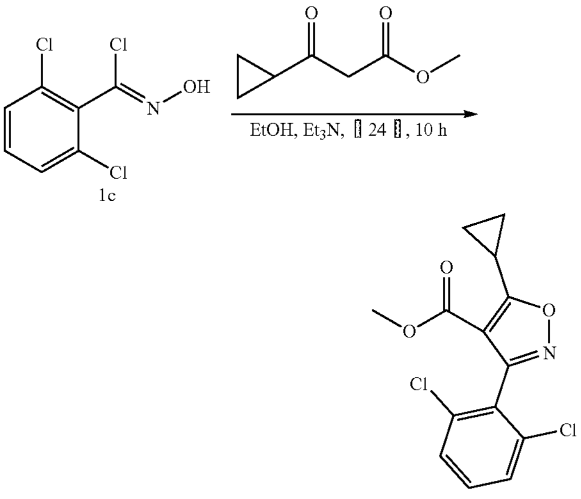

1c

1d

3-Cyclopropyl-methyl 3-oxopropionate (637.7 mg, 4.49 mmol, 1 eq) was added to a 100 mL reaction flask, which was sealed with a rubber stopper. Triethylamine (907.9 mg, 8.97 mmol, 2 eq) was added via a syringe to the reaction flask. The mixture was stirred vigorously at room temperature for 30 min. The reaction liquid was cooled to below 10° C. in an ice bath. A solution of 2, 6-dichloro-N-hydroxy-chlorobenzaldehyde oxime (1.0 g, 4.49 mmol, 1 eq) in ethanol was slowly added dropwise with stirring (monitoring internal temperature <24° C.). After slowly warming to room temperature and vigorously stirring overnight, the ethanol was distilled off under reduced pressure and extracted three times with ethyl acetate (3×100 mL). The organic layer was washed with water (3×100 mL), saturated salt solution (100 mL) and dried over anhydrous sodium sulfate to obtain crude oil. Silica gel column chromatography gradient elution separation and purification (PE:EA=40:1, v/v) was performed to give a white solid (methyl 3-(2, 6-dichlorophenyl)-5-cyclopropylisoxazole-4-methyl formate) 0.89 g, yield 55%.

1.4 Synthesis of 3-(2,6-dichlorophenyl)-4-hydroxymethyl-5-cyclopropylisoxazole

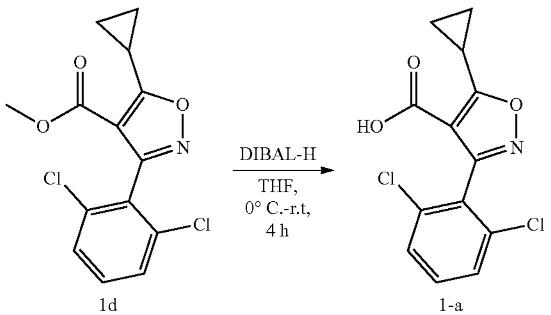 [SMILES: COC(=O)c1c(-c2c(Cl)cccc2Cl)noc1C1CC1 ; O=C(O)c1c(-c2c(Cl)cccc2Cl)noc1C1CC1]

1d 1-a

A solution of diisobutylaluminium hydride in toluene (4.0 mL, 6.0 mmol, 2.1 eq, 1.5M toluene solution) was slowly added dropwise to a solution of 3-(2, 6-dichlorophenyl)-5-cyclopropylisoxazole-4-methyl formate (0.89 g, 2.8 mmol, 1 eq) in anhydrous THF under the condition of nitrogen protection and ice bath. The mixture was allowed to warm to room temperature with vigorous stirring overnight. The reaction solution was re-cooled to 0° C. Methanol (2 mL) was slowly added dropwise and stirred for 10 min. The reaction solution was poured into 50 mL ice-water mixture, resulting in a gel-like suspension. The mixture was filtered by kieselguhr and extracted three times with ethyl acetate (3×100 mL). The combined ester layer was washed with water (3×100 mL) and saturated salt solution (100 mL), dried over anhydrous sodium sulfate and filtered to remove the solvent to give a white solid. Silica gel column chromatography gradient elution separation and purification (PE:EA=20:1, v/v) was performed to give a white solid (3-(2, 6-dichlorophenyl)-4-hydroxymethyl-5-cyclopropylisoxazole) 0.45 g in 56% yield.

2. Synthesis of 3-(2, 6-dichlorophenyl)-4-hydroxymethyl-5-isopropylisoxazole

2.1 Synthesis of 3-(2, 6-dichlorophenyl)-5-isopropylisoxazole-4-methyl formate

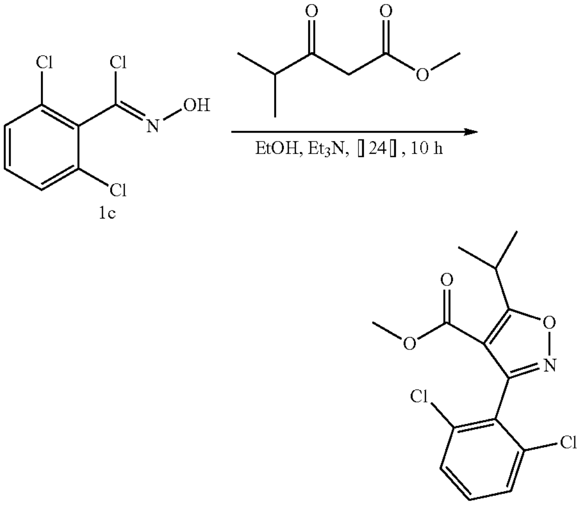

1c

1e

Methyl isobutyrylacetate (16.6 mL, 0.12 mol, 1 eq) was added into a 100 mL reaction flask, which was sealed with a rubber stopper. Triethylamine (33.25 mL, 0.24 mol, 2 eq) was added into the reaction flask via a syringe. The reaction flask was vigorously stirred at room temperature for 30 min. The reaction solution was cooled below 10° C. in an ice bath. A solution of 2, 6-dichloro-N-hydroxy-chlorobenzaldehyde oxime (26.6 g, 0.12 mol, 1 eq) in ethanol was slowly added dropwise with stirring (monitoring internal temperature <24° C.), slowly warmed to room temperature and vigorously stirred overnight. After removing ethanol by distillation under reduced pressure, ethyl acetate was added and the mixture was extracted three times (3×100 mL). The organic layer was washed with water (3×100 mL), saturated salt solution (100 mL) and dried over anhydrous sodium sulfate to obtain crude oil. Silica gel column chromatography gradient elution separation and purification (PE:EA=40:1, v/v) was performed to give a white solid (3-(2, 6-dichlorophenyl)-5-isopropylisoxazole-4-methyl formate) 21 g, yield 56%.

2.2 Synthesis of 3-(2, 6-dichlorophenyl)-4-hydroxymethyl-5-isopropylisoxazole

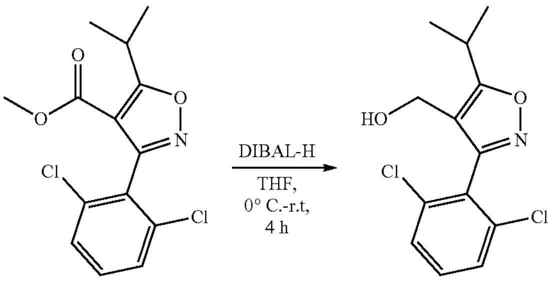

1e 1-b

A solution of diisobutylaluminium hydride in toluene (92 mL, 0.14 mol, 2.1 eq, 1.5M toluene solution) was slowly added dropwise to a solution of 3-(2, 6-dichlorophenyl)-5-isopropylisoxazole-4-methyl formate (20 g, 0.06 mol, 1 eq) in anhydrous THF under the condition of nitrogen protection and ice bath. The mixture was allowed to warm to room temperature with vigorous stirring overnight. The reaction solution was re-cooled to 0° C. Methanol (20 mL) was slowly added dropwise and stirred for 10 min. The reaction solution was poured into 50 mL ice-water mixture, resulting in a gel-like suspension. The mixture was filtered by kieselguhr and extracted three times with ethyl acetate (3×100 mL). The combined ester layer was washed with water (3×100 mL) and saturated salt solution (100 mL), dried over anhydrous sodium sulfate and filtered to remove the solvent to give a white solid. Silica gel column chromatography gradient elution separation and purification (PE:EA=40:1, v/v) was performed to give a white solid (3-(2, 6-dichlorophenyl)-4-hydroxymethyl-5-isopropylisoxazole) 18 g in 94% yield.

3 Synthesis of 3-(2, 6-dichlorophenyl)-4-hydroxymethyl-5-phenylisoxazole

3.1 Synthesis of 3-(2, 6-dichlorophenyl)-5-phenylisoxazole-4-ethyl formate

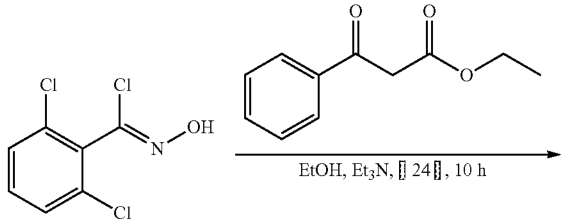

1c

-continued

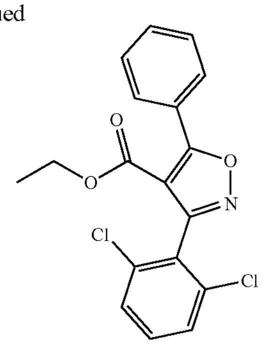

1f

Ethyl benzoylacetate (5.7 mL, 50 mmol, 1 eq) was added into a 100 mL reaction flask, which was sealed with a rubber stopper. Triethylamine (13.86 mL, 100 mmol, 2 eq) was added into the reaction flask via a syringe. The reaction flask was vigorously stirred at room temperature for 30 min. The reaction solution was cooled below 10° C. in an ice bath. A solution of 2, 6-dichloro-N-hydroxy-chlorobenzaldehyde oxime (10 g, 50 mmol, 1 eq) in ethanol was slowly added dropwise with stirring (monitor internal temperature <24° C.), slowly warmed to room temperature, and vigorously stirred overnight. After removing ethanol by distillation under reduced pressure, ethyl acetate was added and the mixture was extracted three times (3×100 mL). The organic layer was washed with water (3×100 mL), saturated salt solution (100 mL) and dried over anhydrous sodium sulfate to obtain crude oil. Silica gel column chromatography gradient elution separation and purification (PE:EA=40:1, v/v) was performed to give a white solid (3-(2, 6-dichlorophenyl)-5-phenylisoxazole-4-methyl formate) 11.7 g, yield 65%.

3.2 Synthesis of 3-(2, 6-dichlorophenyl)-4-hydroxymethyl-5-phenylisoxazole

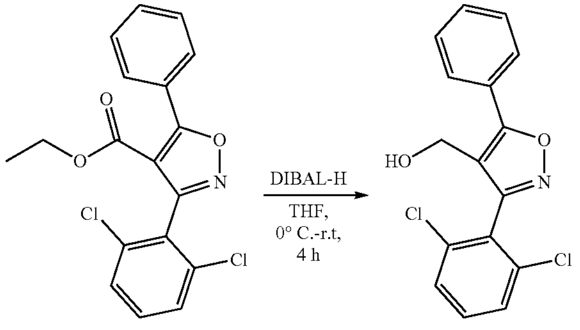

1f 1-c

A solution of diisobutylaluminium hydride in toluene (18 mL, 27 mmol, 2.1 eq, 1.5M toluene solution) was slowly added dropwise to a solution of 3-(2, 6-dichlorophenyl)-5-phenylisoxazole-4-methyl formate (4.72 g, 13 mmol, 1 eq) in anhydrous THF under the condition of nitrogen protection and ice bath. The mixture was allowed to warm to room temperature with vigorous stirring overnight. The reaction solution was re-cooled to 0° C. Methanol (20 mL) was slowly added dropwise and stirred for 10 min. The reaction solution was poured into 200 mL ice-water mixture, resulting in a gel-like suspension. The mixture was filtered by kieselguhr and extracted three times with ethyl acetate (3×100 mL). The combined ester layer was washed with water (3×100 mL) and saturated salt solution (100 mL), dried over anhydrous sodium sulfate and filtered to remove the solvent to give a white solid. Silica gel column chromatography gradient elution separation and purification (PE: EA=20:1, v/v) was performed to give a white solid (3-(2,6-dichlorophenyl)-4-hydroxymethyl-5-phenylisoxazole) 9.1 g, 70% yield.

Embodiment 1: Synthetic Route of Compound TM-1

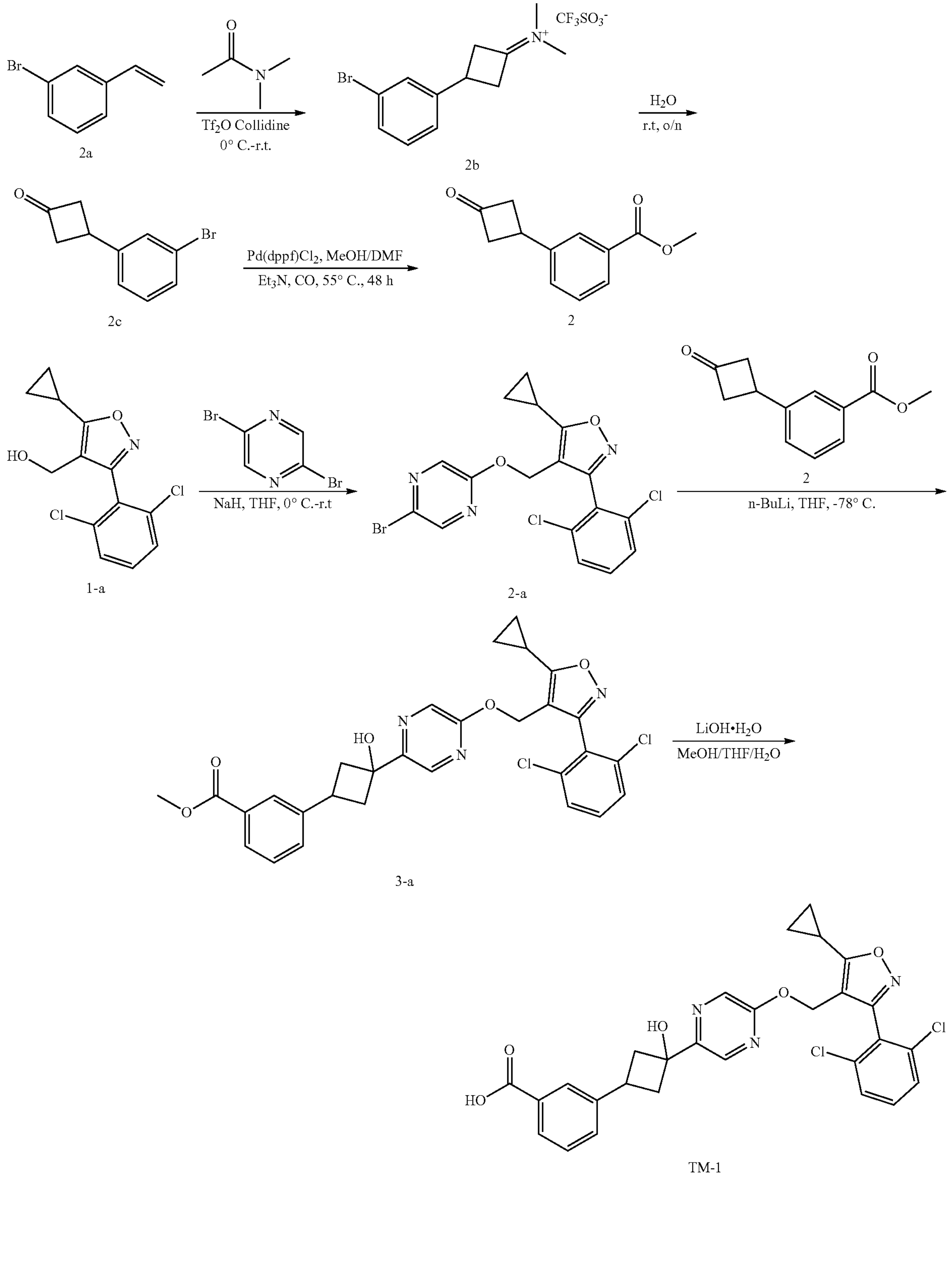

2a

2b

2c

2

1-a

2

2-a 3-a

TM-1

3-(3-bromophenyl) cyclobutanone

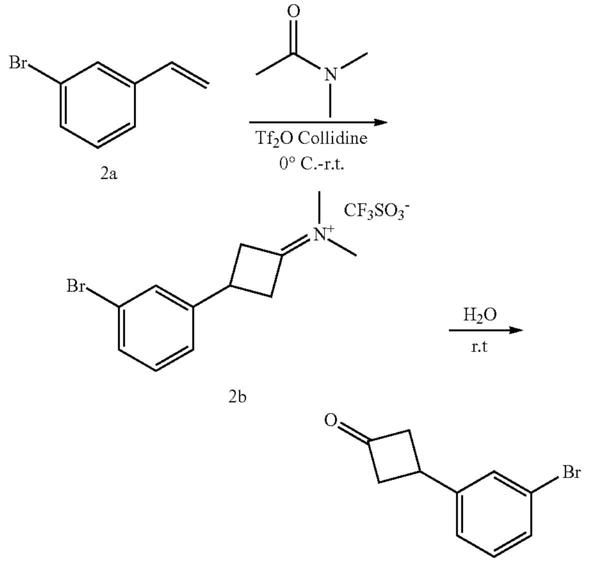

2a

2b

2c

To a solution of N, N-dimethylformamide (2.1 g, 24.6 mmol) in 1, 2-dichloroethane (40 mL) at −15° C., triflic anhydride (11.6 g, 41.0 mmol) was slowly added dropwise and the mixture was stirred at −15° C. for 30 min. 3-bromostyrene (3.0 g, 16.4 mmol) and 2, 4, 6-collidine (2.9 g, 24.6 mmol) were then added and the mixture was stirred at room temperature overnight. The reaction was quenched by adding water. The mixture was stirred at room temperature overnight. Dichloromethane was added to dilute and separate the organic phase, which was washed with water and saturated salt solution (200 ml), dried over anhydrous magnesium sulfate, filtered by suction, concentrated under reduced pressure, and separated and purified by silica gel column chromatography gradient elution (PE:EA=15:1, v/v) to obtain 3-(3-bromophenyl) cyclobutanone as a yellow solid, 1.3 g, yield 35%.

3-(3-oxocyclobutyl) methyl benzoate

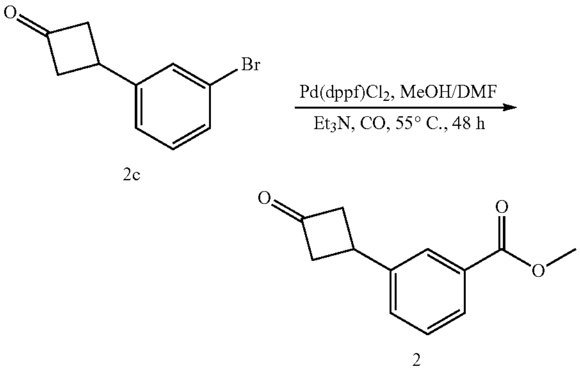

2c

2

Triethylamine (2.2 g, 21.3 mmol) was added to a mixed solvent of 3-(3-oxocyclobutyl) methyl benzoate (1.6 g, 7.1 mmol) and (1, 1-bis (diphenylphosphino) ferrocene) dichloropalladium (520 mg, 0.7 mmol) in methanol (20 mL) and N,N-dimethylformamide (10 mL) at room temperature under a carbon monoxide balloon atmosphere. The mixture was heated to 55° C. for 18 hours, distilled off the solvent under reduced pressure and dissolved in ethyl acetate, washed with water. The organic layer was dried over anhydrous magnesium sulfate, suction filtered, concentrated under reduced pressure, and separated and purified by silica gel column chromatography gradient elution (PE:EA=3:1, v/v) to obtain 3-(3-oxocyclobutyl) methyl benzoate as a yellow oily solid 1.1 g, yield 75%.

4-(5-bromopyrazine-2-ylmethoxy)-5-cyclopropyl-3-(2, 6-dichlorophenyl) isoxazole

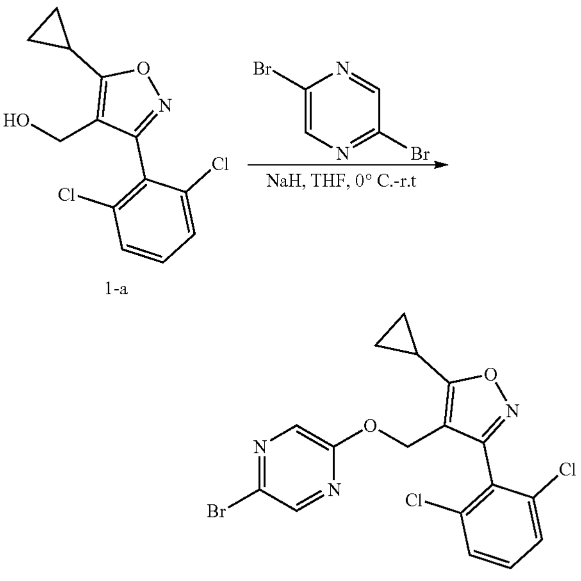

1-a 2-a

In a 100 ml round bottom flask, sodium hydride (4.9 g, 121.6 mmol) was placed, a small amount of petroleum ether was added, and the kerosene layer on the surface of the sodium hydride was washed twice. Tetrahydrofuran (30 ml) was added and the reaction flask was cooled in an ice bath at 0° C. 2, 5-dibromopyrazine (13.1 g, 55.3 mmol) was dissolved in tetrahydrofuran (10 ml) and added dropwise to the round bottom flask with stirring. After the reaction of 20 min, 1-a (5-cyclopropyl-3-(2,6-dichlorophenyl)-isoxazole-4-yl) methanol (15.7 g, 55.3 mmol) was dissolved in tetrahydrofuran (10 ml), and then slowly added dropwise to the reaction flask via a syringe. The temperature was warmed to room temperature and the reaction lasted for 12 h. After the reaction, the reaction solution was poured into 100 ml of ice-water mixture, and then extracted with ethyl acetate (3×100 ml). The combined organic phase was washed with water and saturated salt solution and then dried by anhydrous $MgSO_4$. Silica gel column chromatography gradient elution separation and purification (PE:EA=10:1, v/v) was performed to give white solid 6 (namely, 2-a) (4-(5-bromopyrazine-2-ylmethoxy)-5-cyclopropyl-3-(2, 6-dichlorophenyl) isoxazole) 20.2 g, 83% yield.

3-(3-(5-((5-cyclopropyl-3-(2, 6-dichlorophenyl) isoxazol-4-yl) methoxy) pyrazine-2-yl)-3-hydroxy-cyclobutyl) methyl benzoate

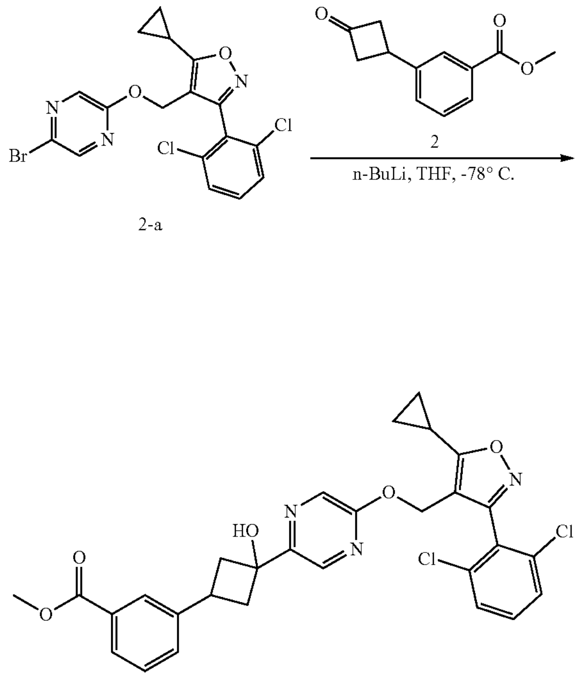

3-a

In a 100 ml three-necked flask under nitrogen protection, 6 (20.2 g, 45.8 mmol) was dissolved in tetrahydrofuran (80 ml) and the mixture was added into the reaction flask. Then the temperature was lowered to −78° C. N-butyl lithium (1.6M in hexane, 30.0 mL, 48.0 mmol) was slowly added dropwise. After stirring for 10 min, a solution of 3-(3-oxocyclobutyl) methyl benzoate 2 (9.0 g, 43.6 mmol) dissolved in tetrahydrofuran (20 ml) was slowly added dropwise. After reaction for 2 h at −78° C., the mixture was allowed to warm to room temperature overnight. After the reaction, the reaction was quenched with saturated ammonium chloride. The mixture was extracted with ethyl acetate. The organic phase was washed with saturated salt solution (200 ml), dried over anhydrous magnesium sulfate, and suction filtered. The organic solvent was distilled off under reduced pressure. Separated and purified by silica gel column chromatography gradient elution (PE:EA=15:1, v/v) was performed to obtain 3-(3-(5-((5-cyclopropyl-3-(2, 6-dichlorophenyl) isoxazol-4-yl) methoxy) pyrazine-2-yl)-3-hydroxycyclobutyl) methyl benzoate as a yellow solid 5.6 g, 19% yield.

3-(3-(5-(5-cyclopropyl-3-(2, 6-dichlorophenyl)-4-ylmethoxy)-2-pyrazine)-1-hydroxycyclobutane) benzoic acid

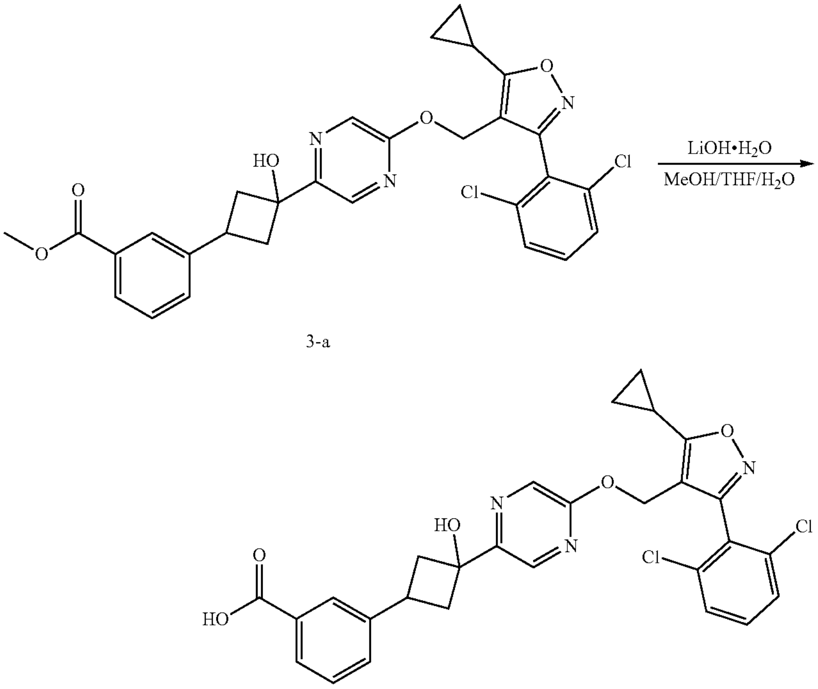

TM-1

3-(3-(5-((5-cyclopropyl-3-(2, 6-dichlorophenyl) isoxazol-4-yl) methoxy) pyrazine-2-yl)-3-hydroxycyclobutyl) methyl benzoate (5.6 g, 10.1 mmol) was dissolved in a mixed solvent of THF (10 mL) and methanol (10 mL). A solution of $LiOH \cdot H_2O$ (1.8 g, 42.6 mmol) in water (5 ml) was added at 35° C. The mixture was stirred overnight. The organic solvent was removed by distillation under reduced pressure. The pH was adjusted to 5 with 1N hydrochloric acid. The mixture was extracted three times by adding ethyl acetate, dried with anhydrous magnesium sulfate, with the solvent removed by distillation under reduced pressure, and separated and purified by high-pressure preparative liquid chromatography (acetonitrile:water=3:4, v/v) to obtain TM-1 3-(3-(5-(5-cyclopropyl-3-(2, 6-dichlorophenyl) isoxazole-4-ylmethoxy)-2-pyrazine)-1-hydroxycyclobutane) benzoic acid as a white solid 3.28 g, 57% yield.

As shown in FIG. 1, $^1H$-NMR (400 MHz, DMSO-D6): δ 12.95 (s, 1H), 8.22-8.21 (m, 1H), 8.12-8.11 (m, 1H), 7.95-7.94 (m, 1H), 7.72 (d, J=2 Hz, 1H), 7.66-7.49 (m, 4H), 7.48-7.37 (m, 1H), 6.06 (s, 1H), 5.24 (s, 2H), 3.57-3.37 (m, 1H), 2.94-2.89 (m, 2H), 2.55-2.42 (m, 3H), 1.21 (d, J=24 Hz, 2H), 1.15 (d, J=16 Hz, 2H).

Figure 2:
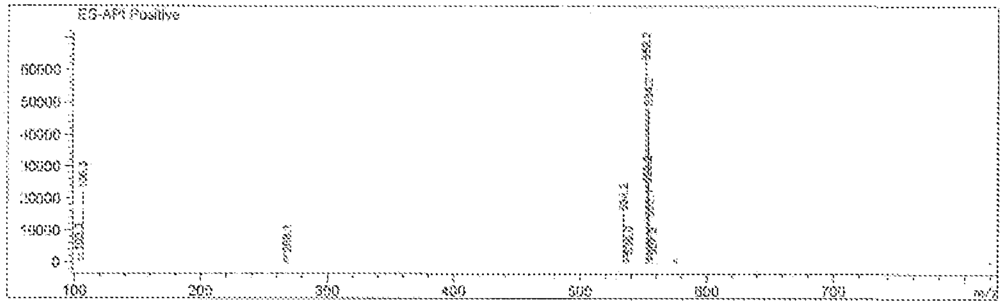
FIG. 2 is the mass spectrogram of compound TM-1 of the present invention.

As shown in FIG. 2, SI-MS: m/z[M+H]+: Calcd. for $C_{28}H_{23}Cl_2N_3O_5$: 551.1, Found: 552.2.

Embodiment 2: Synthetic Route of Compound TM-2

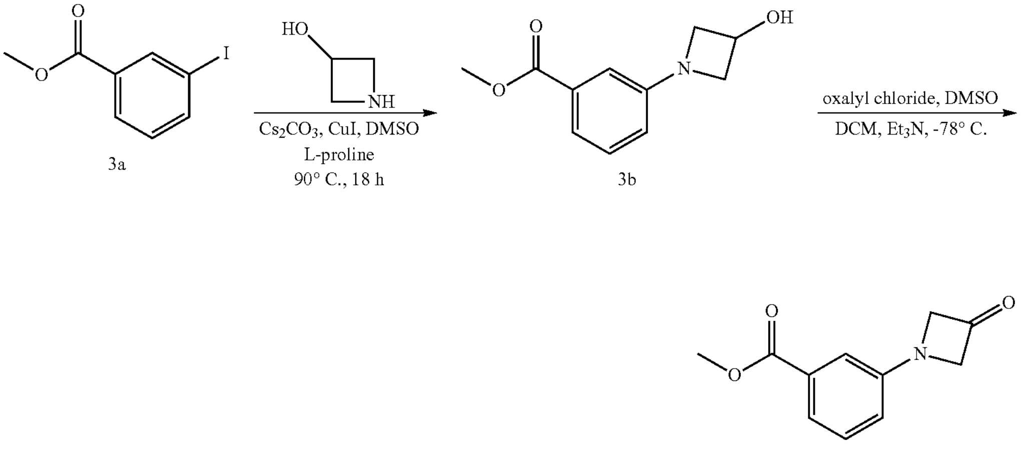

3a
3b
3

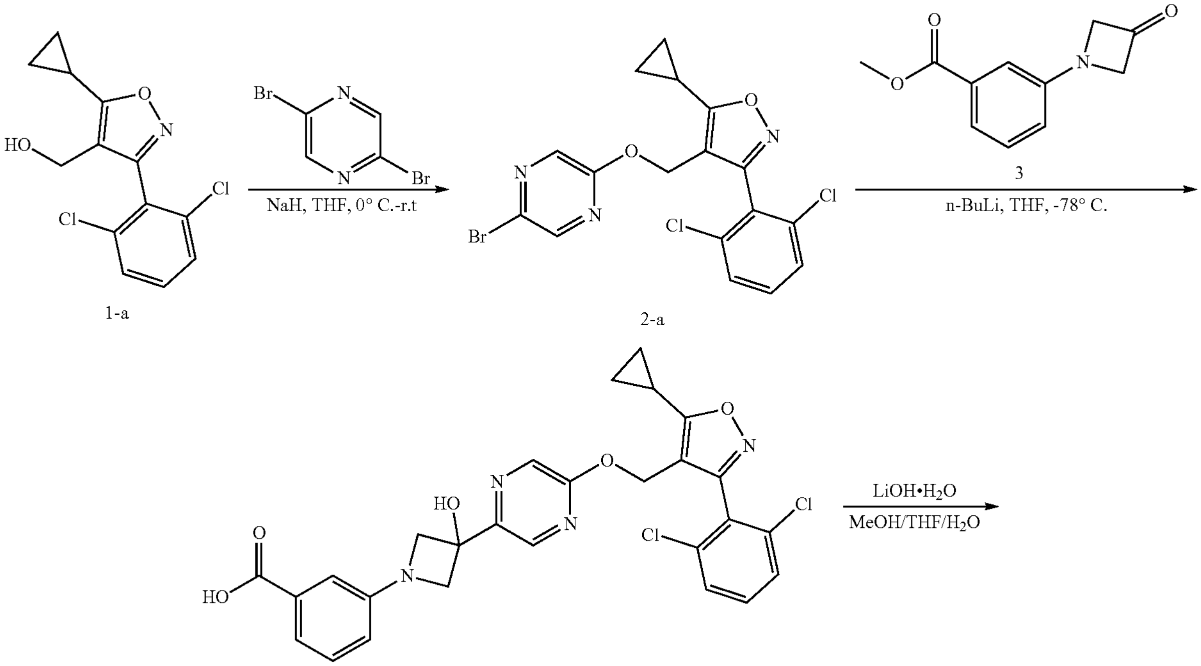

1-a
2-a
3
3-b

-continued

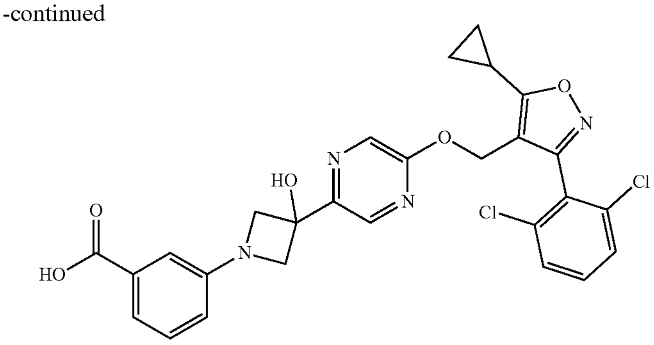

TM-2

Synthetic Steps

Synthesis of 3-(3-hydroxyazetidin-1-yl) methyl benzoate 3b

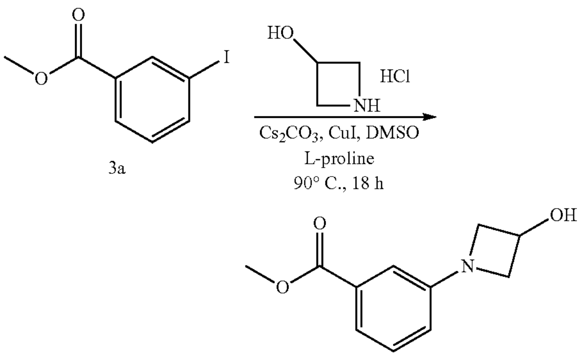

3a

3b

To a solution of methyl 3-iodobenzoate 3a (5.0 g, 19.1 mmol) in DMSO-$D_6$ (70 mL) was added 3-azetidine-3-ol hydrochloride (2.5 g. 22.9 mmol), $Cs_2CO_3$ (15.5 g, 47.7 mmol), CuI (726 mg, 3.8 mmol) and L-proline (878 mg, 7.6 mmol). The mixture was then heated at 90° C. for 18 hours under argon atmosphere. The solution was diluted with ethyl acetate and water. Then the organic layer was washed with saline water three times, concentrated under reduced pressure, and separated and purified by silica gel column chromatography (DCM/MeOH=10/1, v/v) to give the product 3b as a white solid (2.7 g, 68%).

Synthesis of 3-(3-oxazacyclobutane-1-yl) methyl benzoate 3

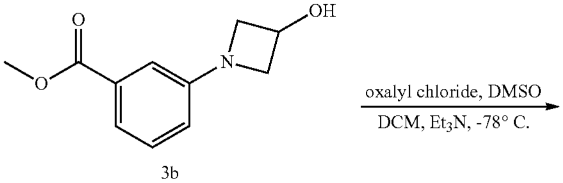

3b

-continued

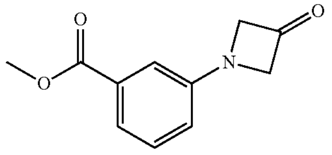

3

Dimethyl sulfoxide (1.6 g, 20.3 mmol) was dissolved in dichloromethane (30 mL). Oxalyl chloride (1.3 g, 10.1 mmol) was added at −78° C. The mixture was stirred at −78° C. for 30 minutes. Then 3-(3-hydroxyazetidin-1-yl) methyl benzoate (1.4 g, 6.8 mmol) was dissolved in dichloromethane and slowly added dropwise to the reaction liquid at −78° C. with time controlled at 30 minutes, and then stirred at −78° C. for 30 minutes, followed by the addition of triethylamine (4.1 g, 40.5 mmol). The mixture reacted at −78° C. for 1 hour, and warmed to room temperature and reacted at room temperature for 2 hours. The reaction solution was diluted with water and extracted with ethyl acetate. The organic phase was washed with saturated salt solution, dried over anhydrous sodium sulfate, concentrated by suction filtration, and separated and purified by silica gel column chromatography (PE/EA=2/1) to give the product 3 as a white solid (0.9 g, 65%).

3-(3-(5-((5-cyclopropyl-3-(2, 6-dichlorophenyl) isoxazol-4-yl) methoxy)pyrazin-2-yl)-3-hydroxyazetidin-1-yl) methyl benzoate

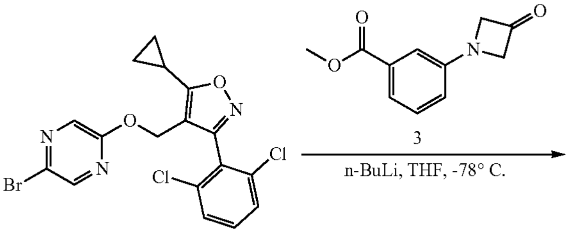

3

2-a

-continued

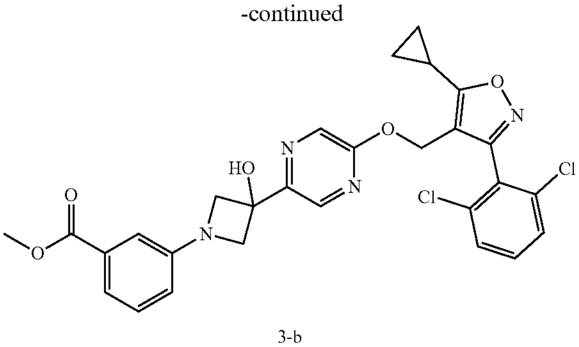

3-b

In a 100 ml three-necked flask under nitrogen protection, 6 (1.9 g, 4.4 mmol) was dissolved in tetrahydrofuran (25 ml) and added into the reaction flask. The temperature was lowered to −78° C. N-butyl lithium (2.5M in hexane, 2.6 mL, 6.6 mmol) was slowly added dropwise. After stirring for 10 min, a solution of 3-(3-oxazacyclobutane-1-yl) methyl benzoate 3 (0.9 g, 4.4 mmol) dissolved in tetrahydrofuran (5 ml) was slowly added dropwise. After reaction for 2 h at −78° C., the mixture was allowed to warm to room temperature overnight. After the reaction, the reaction was quenched with saturated ammonium chloride. The mixture was extracted with ethyl acetate. The organic phase was washed with saturated salt solution (200 ml), dried over anhydrous magnesium sulfate, and suction filtered. The organic solvent was distilled off under reduced pressure. Separated and purified by silica gel column chromatography gradient elution (PE:EA=15:1, v/v) was performed to obtain a yellow solid 7 (namely 3-b) 3-(3-(5-((5-cyclopropyl-3-(2, 6-dichlorophenyl) isoxazol-4-yl) methoxy) pyrazine-2-yl)-3-hydroxycyclobutyl) methyl benzoate 560 mg, 22% yield.

3-(3-(5-((5-cyclopropyl-3-(2, 6-dichlorophenyl) isoxazol-4-yl) methoxy) pyrazine-2-yl)-3-hydroxyazetidin-1-yl) benzoic acid

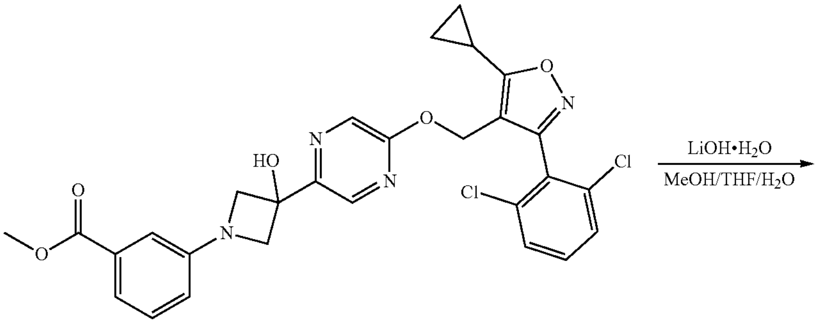

3-b

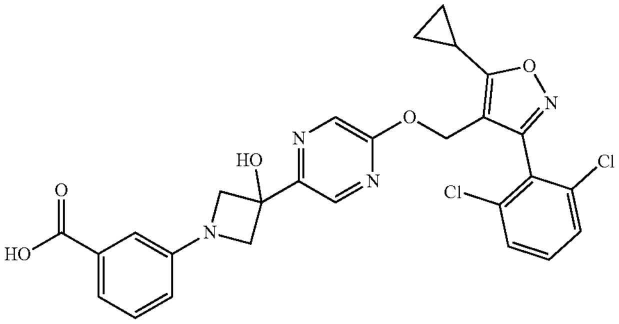

TM-2

3-(3-(5-((5-cyclopropyl-3-(2, 6-dichlorophenyl) isoxazol-4-yl) methoxy) pyrazine-2-yl)-3-hydroxycyclobutyl) methyl benzoate (270 mg, 0.5 mmol) was dissolved in a mixed solvent of THF (3 ml) and methanol (3 ml). A solution of $LiOH \cdot H_2O$ (60 mg, 1.5 mmol) in water (3 ml) was added at 35° C. The mixture was stirred overnight. The organic solvent was removed by distillation under reduced pressure. The pH was adjusted to 5 with 1N hydrochloric acid. The mixture was extracted three times by adding ethyl acetate, dried with anhydrous magnesium sulfate, with the solvent removed by distillation under reduced pressure. Separated and purified by high-pressure preparative liquid chromatography (acetonitrile:water=3:4, v/v) was performed to obtain 3-(3-(5-((5-cyclopropyl-3-(2, 6-dichlorophenyl) isoxazol-4-yl) methoxy) pyrazine-2-yl)-3-hydroxycyclobutyl benzoic acid) (namely TM-2) as a white solid 40 mg, yield 15%.

Figure 3:
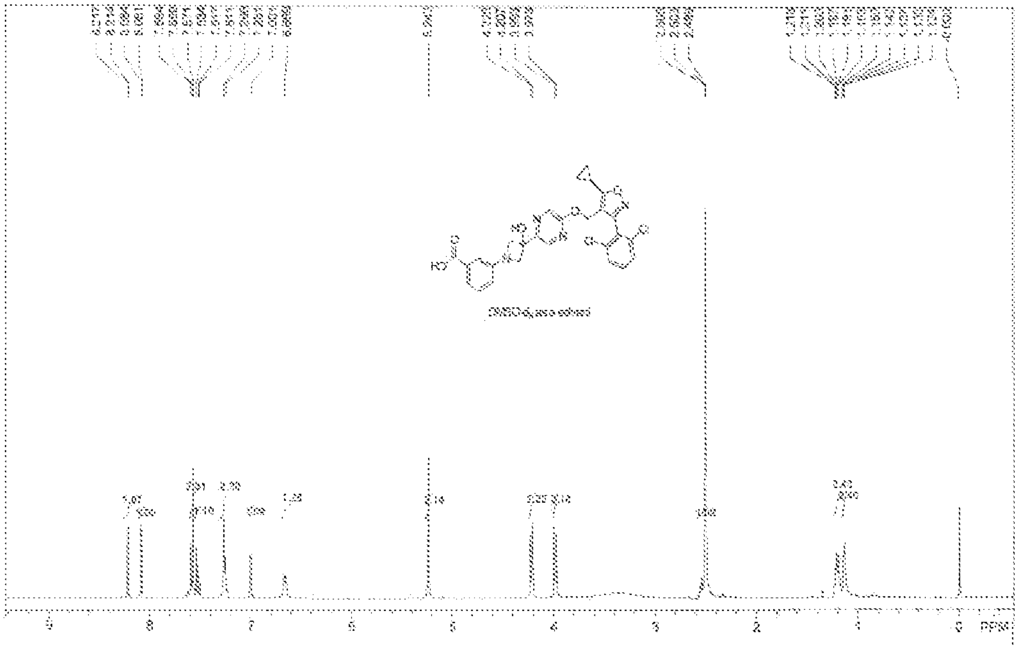
FIG. 3 is the $^1$H-NMR spectrogram of compound TM-2 of the present invention.

As shown in FIG. 3, $^1$H-NMR (400 MHz, DMSO-D6): δ 8.22-8.21 (m, 1H), 8.08-8.08 (m, 1H), 7.59-7.51 (m, 4H), 7.27-7.25 (m, 2H), 7.00 (s, 1H), 6.67 (s, 1H), 5.24 (s, 2H), 4.21 (d, J=16 Hz, 2H), 3.98 (d, J=16 Hz, 2H), 2.51-2.50 (m, 1H), 1.22-1.18 (m, 2H), 1.15-1.12 (m, 2H).

Figure 4:
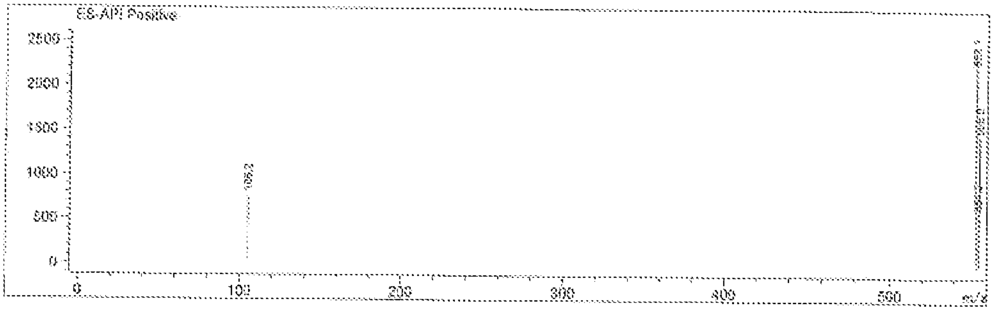
FIG. 4 is the mass spectrogram of compound TM-2 of the present invention.

As shown in FIG. 4, ESI-MS: m/z[M+H]+: Calcd. for $C_{27}H_{22}Cl_2N_4O_5$: 552.1, Found: 553.1 (note, values are on right side of figure).

Embodiment 3: Synthetic Route of Compound TM-3

3-(3-bromophenyl)-1-(5-((5-cyclopropyl-3-(2, 6-dichlorophenyl) isoxazol-4-yl) methoxy) pyrazine-2-yl) cyclobutanol

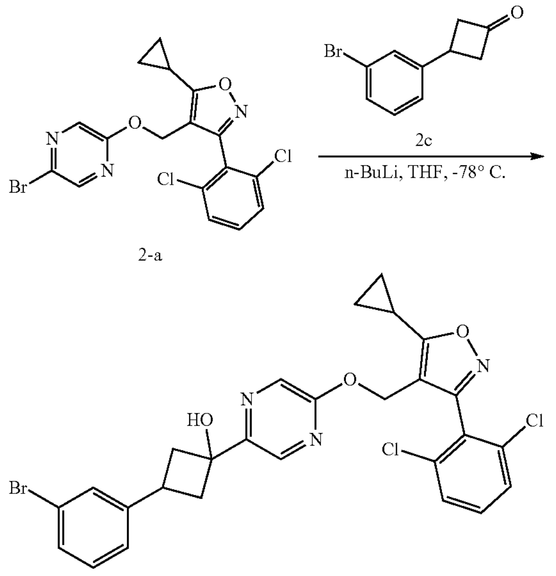

2-a
TM-3

In a 100 ml three-necked flask under nitrogen protection, 4-(5-bromopyrazine-2-ylmethoxy)-5-cyclopropyl-3-(2, 6-dichlorophenyl) isoxazole (1.14 g, 2.3 mmol) dissolved in anhydrous tetrahydrofuran (5 mL) was put into a reaction flask. Ethanol and liquid nitrogen were added into a 500 mL low-temperature Dewar flask to reduce the temperature to −78° C. N-butyllithium (1.7 ml, 2.7 mmol) was slowly added dropwise, and the mixture was stirred for 10 min. A solution of 3-(3-oxocyclobutanone) methyl benzoate (0.56 g, 2.5 mmol) dissolved in tetrahydrofuran (10 mL) was slowly added dropwise. The mixture was allowed to react for 2 h at −78° C. and then warm to room temperature to react overnight. After the reaction, the reaction liquid was slowly poured into an ice-water mixture, and extracted with ethyl acetate. The ester layer was washed with water (100 mL), dried over anhydrous magnesium sulfate, suction filtered, with the organic solvent distilled off under reduced pressure, and separated and purified by silica gel column chromatography gradient elution (PE:EA=10:1, v/v) to obtain 3-(3-bromophenyl)-(5-(5-cyclopropyl-3-(2, 6-dichlorophenyl) isoxazol-4-yl) methoxy) pyrazine-2-yl) cyclobutane-1-ol as a white solid, 567 mg, 42% yield.

Figure 5:
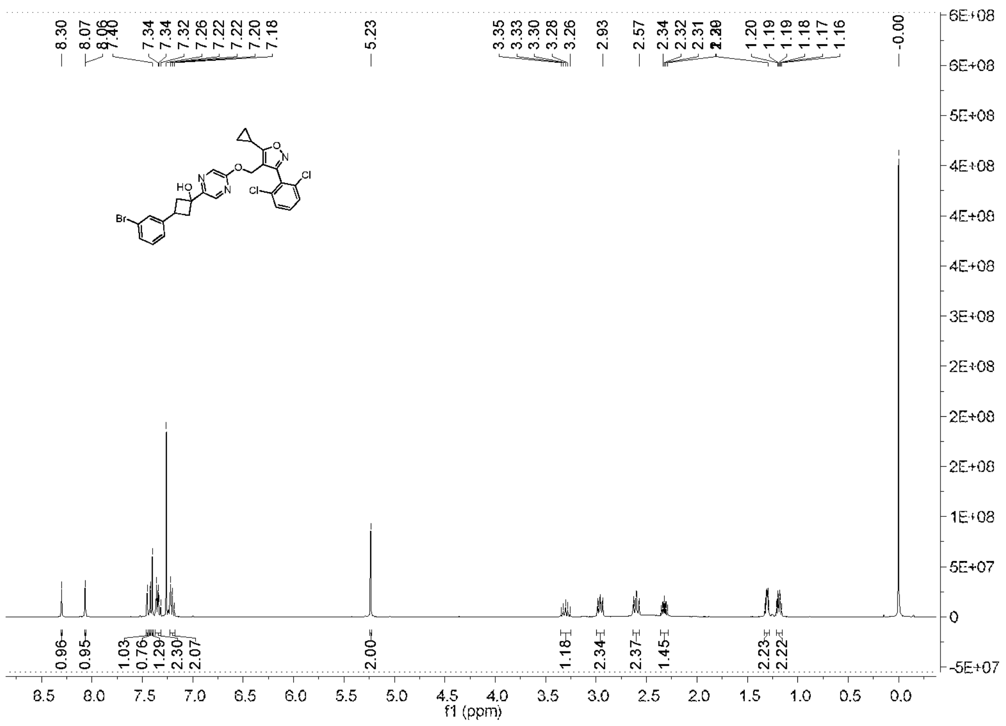
FIG. 5 is the $^1$H-NMR spectrogram of compound TM-3 of the present invention.
Figure 6:
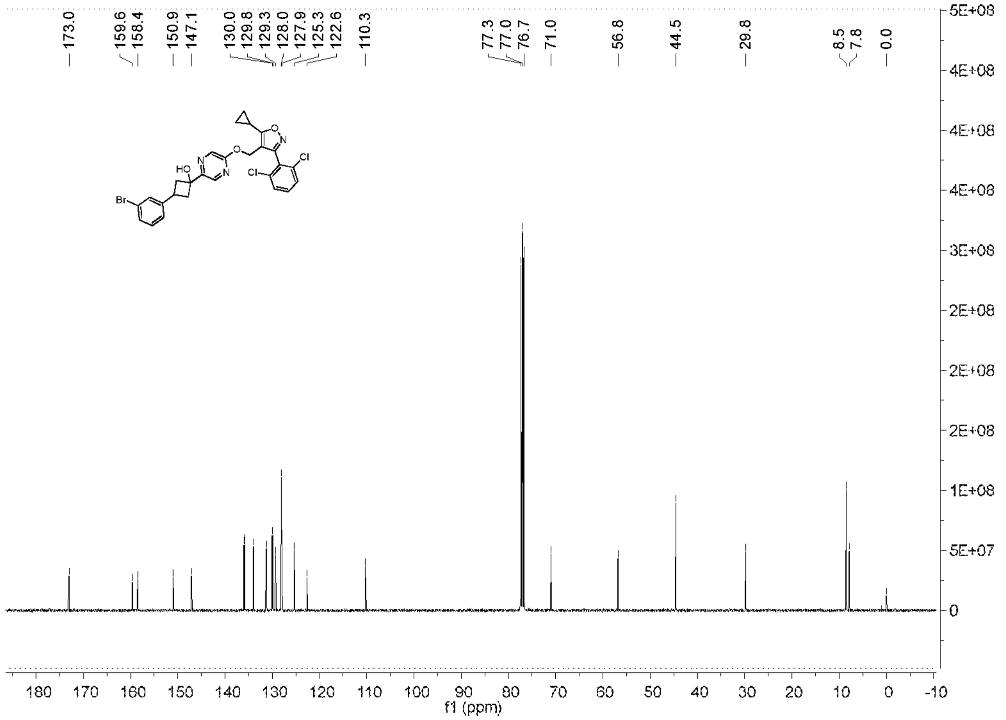
FIG. 6 is the 1$^3$C-NMR spectrogram of compound TM-3 of the present invention.

As shown in FIG. 5, $^1$H-NMR (400 MHz, CDCl3): δ 8.30 (1H, s), 8.06 (1H, d, J=4 Hz), 7.45 (1H, s), 7.42 (1H, d, J=1.6 Hz), 7.40 (1H, s), 7.36-7.32 (2H, m, J=16 Hz), 7.22-7.18 (2H, m, J=16 Hz), 5.23 (2H, s), 3.35-3.26 (1H, m), 2.99-2.93 (2H, m), 2.63-2.57 (2H, m), 2.36-2.29 (1H, m), 1.33-1.29 (2H, d, J=24 Hz), 1.21-1.16 (2H, d, J=16 Hz). As shown in FIG. 6, 1$^3$C-NMR (100 MHz, DMSO-D6): 173.0, 159.6, 158.4, 150.9, 147.1, 130.0, 129.8, 129.3, 128.0, 127.9, 125.3, 122.6, 110.3, 71.0, 56.8, 44.5, 29.8, 8.5, 7.8.

Figure 7:
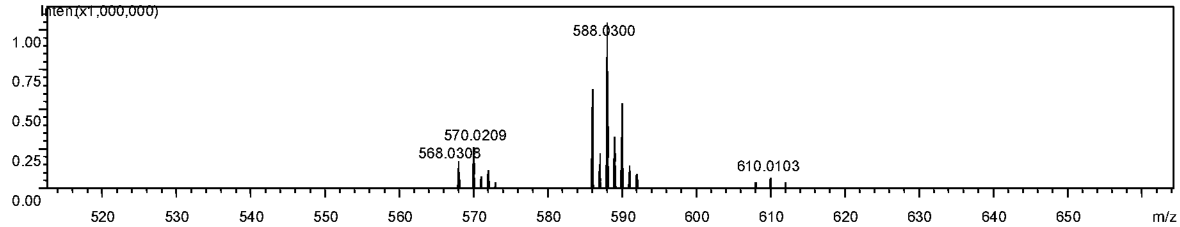
FIG. 7 is the mass spectrogram of compound TM-3 of the present invention.

As shown in FIG. 7, ESI-MS: m/z[M+2+H]+: Calcd. for $C_{27}H_{22}BrCl_2N_3O_3$: 585.0222, Found: 588.0300.

Embodiment 4: Synthetic Route of Compound TM-4

1-(5-((5-cyclopropyl-3-(2, 6-dichlorophenyl) isoxazol-4-yl) methoxy) pyrazine-2-yl)-3-(3-(methylsulfonyl) phenyl) cyclobutanol

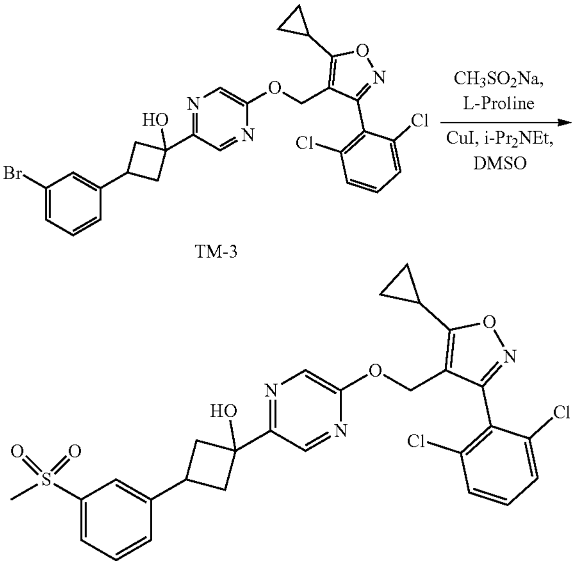

TM-3
TM-4

To a solution of 3-(3-bromophenyl)-1-(5-((5-cyclopropyl-3-(2, 6-dichlorophenyl) isoxazol-4-yl) methoxy) pyrazine-2-yl) cyclobutanol (500 mg, 0.85 mmol) in DMSO-D6 was added sodium methanesulfinate (130 mg, 1.28 mmol), CuI (50.2 mg, 0.26 mmol), L-proline (97.9 mg, 0.85 mmol) and diisopropylethylamine (DIPEA) (109.9 mg, 0.85 mmol). The mixture was stirred at 95° C. overnight, then diluted with water and extracted with EA. The organic phases were combined, washed with water and dried over $Na_2SO_4$. It was concentrated to dryness under reduced pressure and separated and purified by high pressure preparative liquid chromatography (acetonitrile:water=3:4, v/v) to obtain 1-(5-((5-cyclopropyl-3-(2, 6-dichlorophenyl) isoxazol-4-yl) methoxy) pyrazine-2-yl)-3-(3-(methylsulfonyl) phenyl) cyclobutanol as a white solid 324 mg, yield 65%.

Figure 8:
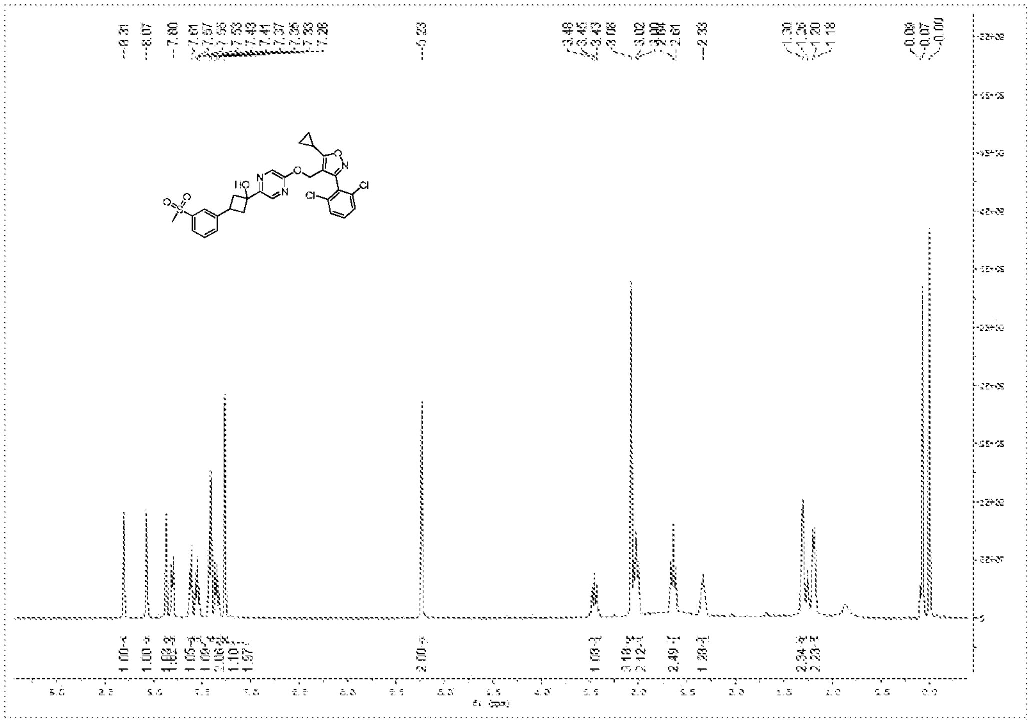
FIG. 8 is the $^1$H-NMR spectrogram of compound TM-4 of the present invention.

As shown in FIG. 8, $^1$H-NMR (400 MHz, CDCl3): δ 8.15 (s, 1H), 7.92 (s, 1H), 7.72-7.65 (m, 2H), 7.42-7.40 (m, 2H), 7.28-7.12 (m, 2H), 5.08 (s, 2H), 3.33-3.29 (m, 1H), 2.93-2.85 (m, 5H), 2.51-2.46 (m, 2H), 2.21-2.18 (m, 1H), 1.15 (d, J=16 Hz, 2H), 1.05 (d, J=16 Hz, 2H).

Figure 9:
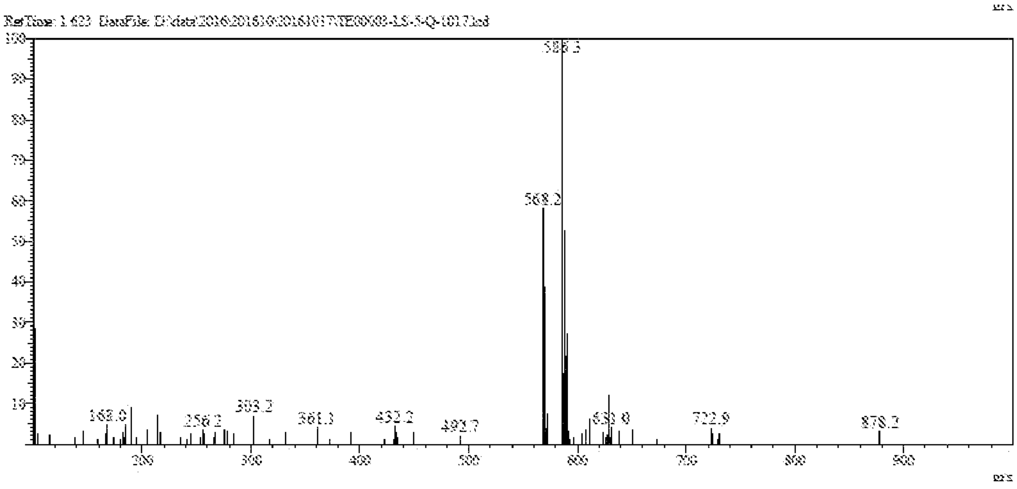
FIG. 9 is the mass spectrogram of compound TM-4 of the present invention.

As shown in FIG. 9, ESI-MS: m/z[M+H]+: Calcd. for $C_{28}H_{25}Cl_2N_3O_5S$: 585.1, Found: 586.3.

Embodiment 5: Synthetic Route of Compound TM-5

1-(5-((5-cyclopropyl-3-(2, 6-dichlorophenyl) isoxazol-4-yl) methoxy) pyrazine-2-yl)-3-(3-(phenylthio) phenyl) cyclobutanol

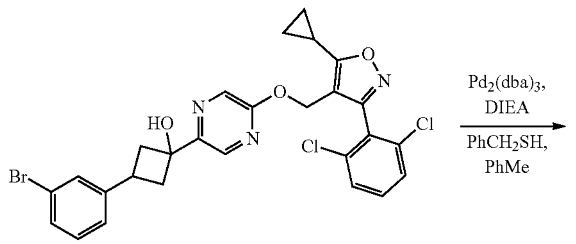

TM-3

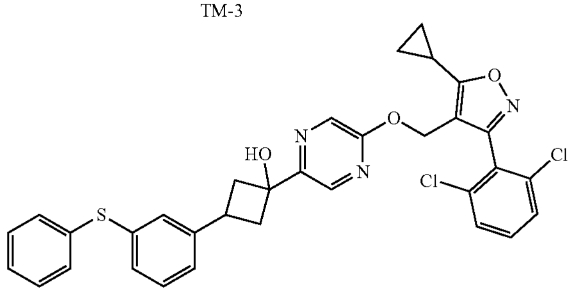

TM-5

To a solution of 3-(3-bromophenyl)-1-(5-((5-cyclopropyl-3-(2, 6-dichlorophenyl) isoxazol-4-yl) methoxy) pyrazine-2-yl) cyclobutanol (1.0 g, 1.7 mmol) in toluene under argon protection was added DIEA (0.44 g, 3.41 mmol), thiobenzyl alcohol (0.21 g, 1.7 mmol), $Pd_2(dba)_3$ (0.34 g, 0.37 mmol) and 4, 5-bisdiphenylphosphino-9, 9-dimethylxanthene (0.16 g, 0.27 mmol). The mixture was then stirred at 115° C. for 4 hours, and cooled to room temperature, diluted with water and extracted with EA. The organic phases were combined, washed with water and dried over $Na_2SO_4$. It was concentrated to dryness under reduced pressure and separated and purified by high pressure preparative liquid chromatography (acetonitrile:water=3:4, v/v) to obtain 1-(5-((5-cyclopropyl-3-(2, 6-dichlorophenyl) isoxazol-4-yl) methoxy) pyrazine-2-yl)-3-(3-(phenylthio) phenyl) cyclobutanol 367 mg as a white solid, yield 35%.

Figure 10:
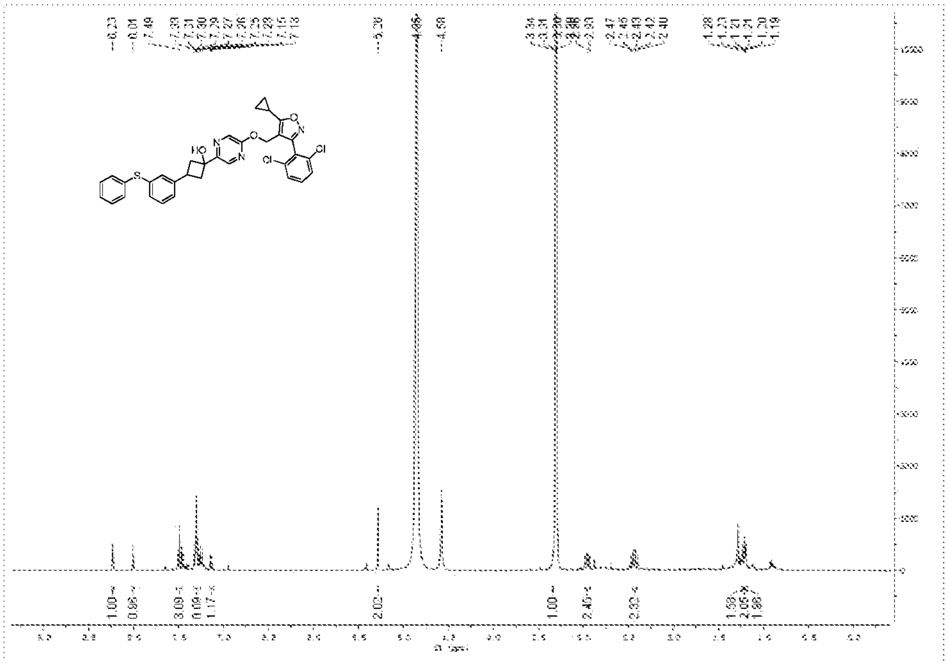
FIG. 10 is the $^1$H-NMR spectrogram of compound TM-5 of the present invention.

As shown in FIG. 10, $^1$H-NMR (400 MHz, CDCl3): δ 8.23 (s, 1H), 8.01 (s, 1H), 7.46-7.54 (m, 3H), 7.23-7.33 (m, 8H), 7.14 (br d, J=7.6 Hz, 1H), 5.28 (s, 2H), 3.31-3.34 (m, 1H), 4.85 ($H_2O$), 4.58 (HDO), 3.30 ($CD_3OD$), 2.92-3.02 (m, 2H), 2.41-2.50 (m, 2H), 1.23 (s, 1H), 1.21 (br d, J=2.0 Hz, 2H), 1.19 (br d, J=2.0 Hz, 2H).

Figure 11:
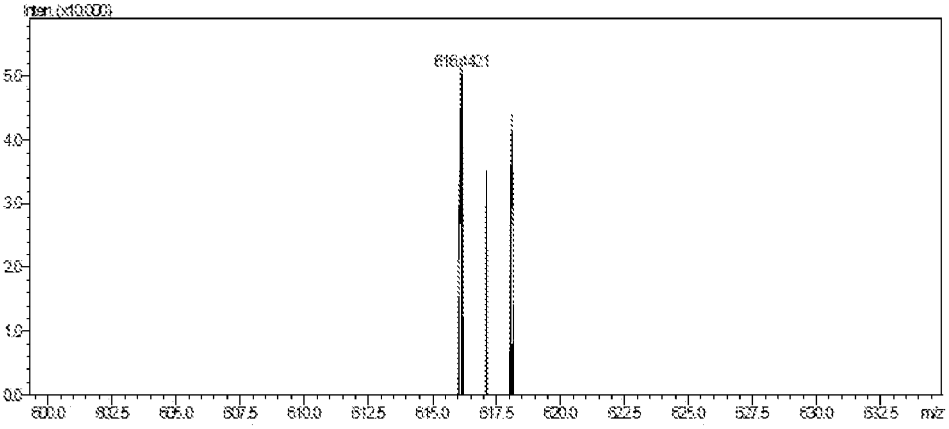
FIG. 11 is the mass spectrogram of compound TM-5 of the present invention.

As shown in FIG. 11, ESI-MS: m/z[M+H]+: Calcd. for $C_{33}H_{27}Cl_2N_3O_3S$: 615.1150, Found: 616.1421.

Embodiment 6: Synthesis of Compound TM-6

Synthesis of 4-(5-bromopyrazine-2-ylmethoxy)-5-isopropyl-3-(2, 6-dichlorophenyl) isoxazole

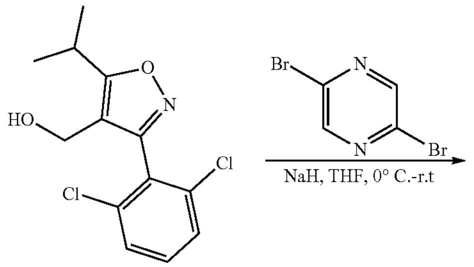

1-b

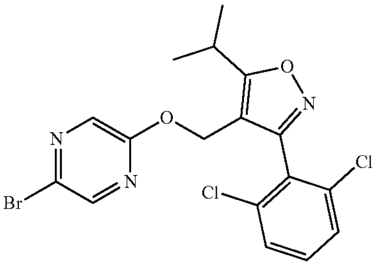

2-b

In a 100 mL round bottom flask, sodium hydride (60%, 0.83 g, 21 mmol) was placed, a small amount of petroleum ether was added, and the kerosene layer on the surface of the NaH was washed twice. 30 mL tetrahydrofuran was added and the reaction flask was cooled in a 0° C. ice bath. 2, 5-dibromopyrazine (833 mg, 3.5 mmol) was dissolved in 10 mL tetrahydrofuran and added dropwise to the round bottom flask with stirring. After the reaction for 20 min, 3-(2, 6-dichlorophenyl)-4-hydroxymethyl-5-isopropylisoxazole (1 g, 3.5 mmol) was dissolved in 10 mL of tetrahydrofuran, and the mixture was slowly dropped into the reaction flask by the needle tube. The reaction was allowed to warm to room temperature for 12 h. After the reaction, the reaction solution was poured into 100 mL of ice-water mixture, and then extracted with ethyl acetate (3×100 mL). The combined organic phase was washed with water and saturated salt solution and dried by anhydrous $MgSO_4$. Separation and purification by silica gel column chromatography gradient elution (PE:EA=10:1, v/v) was performed to give 4-(5-bromopyrazine-2-ylmethoxy)-5-isopropyl-3-(2, 6-dichlorophenyl) isoxazole as a white solid, 0.7 g, 53% yield.

Synthesis of 3-(3-(5-((3-(2, 6-dichlorophenyl)-5-isopropylisoxazol-4-yl) methoxy) pyrazine-2-yl)-3-hydroxycyclobutyl) methyl benzoate

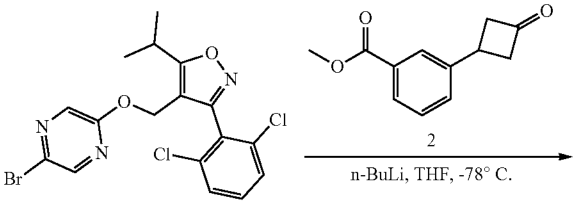

2-b

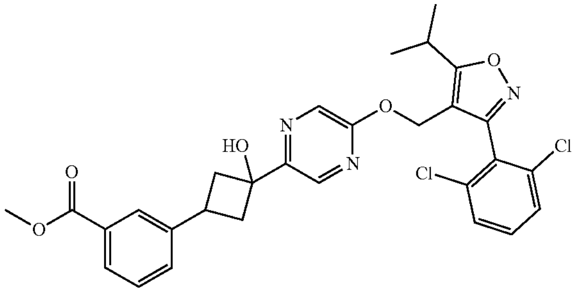

3-c

In a 100 ml three-necked flask under nitrogen protection, 4-(5-bromopyrazine-2-ylmethoxy)-5-isopropyl-3-(2, 6-dichlorophenyl) isoxazole (Ig, 2.3 mmol) dissolved in anhydrous tetrahydrofuran (20 mL) was put into a reaction flask. Ethanol and liquid nitrogen were added into a 500 mL low-temperature Dewar flask to reduce the temperature to −78° C. N-butyllithium (1.7 ml, 2.7 mmol) was slowly added dropwise, and the mixture was stirred for 10 min. A solution of 3-(3-oxocyclobutanone) methyl benzoate (0.51 g, 2.5 mmol) in tetrahydrofuran (10 mL) was slowly added dropwise. The mixture was allowed to warm to room temperature overnight after reaction for 2 h at −78° C. After the reaction, the reaction solution was slowly poured into an ice-water mixture and extracted with ethyl acetate, with the ester layer washed with water (100 mL), dried over anhydrous magnesium sulfate, suction filtered, with the organic solvent distilled off under reduced pressure, and separated and purified by silica gel column chromatography gradient elution (PE:EA=10:1, v/v) to obtain 3-(3-(5-((3-(2, 6-dichlorophenyl)-5-isopropylisoxazol-4-yl) methoxy) pyrazine-2-yl)-3-hydroxycyclobutyl) methyl benzoate as a white solid 549 mg, 42% yield.

Synthesis of 3-(3-(5-(5-isopropyl-3-(2, isoxazole-4-ylmethoxy)-2-pyrazine)-1-hydroxycyclobutane) benzoic acid

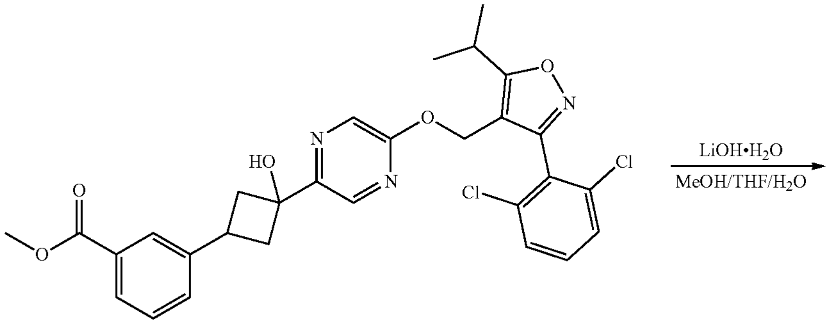

3-c

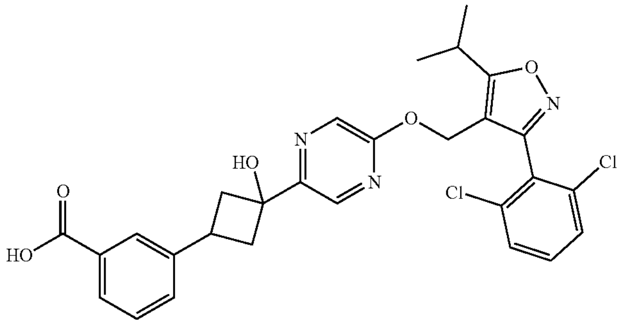

TM-6

3-(3-(5-((3-(2, 6-dichlorophenyl)-5-isopropylisoxazol-4-yl) methoxy) pyrazine-2-yl)-3-hydroxycyclobutyl) methyl benzoate (319 mg, 0.6 mmol, 1 eq) was dissolved in 20 mL THF and a solution of $LiOH \cdot H_2O$ (99 mg, 2.4 mmol, 4.2 eq) in water (5 mL) was added at 35° C. The mixture was stirred overnight. The organic solvent was removed by distillation under reduced pressure. The pH was adjusted to 5 with 1N hydrochloric acid. The mixture was extracted three times by adding ethyl acetate, dried with anhydrous magnesium sulfate, with the solvent removed by distillation under reduced pressure, and separated and purified by high-pressure preparative liquid chromatography. A Waters XBridge C18 column (150 nm*4.6 nm*3.5 um) is used, with a mobile phase of acetonitrile and water, a flow rate of 18 mL/min, fractions collected with a gradient of 45%-75%, and most of the acetonitrile removed by concentrating. The mixture was treated by lyophilization with a lyophilizer to give 126 mg of (3-(3-(5-(5-isopropyl-3-(2, 6-dichlorophenyl) isoxazole-4-ylmethoxy)-2-pyrazine)-1-hydroxycyclobutane) benzoic acid as a white powdery solid, yield 38%.

Figure 12:
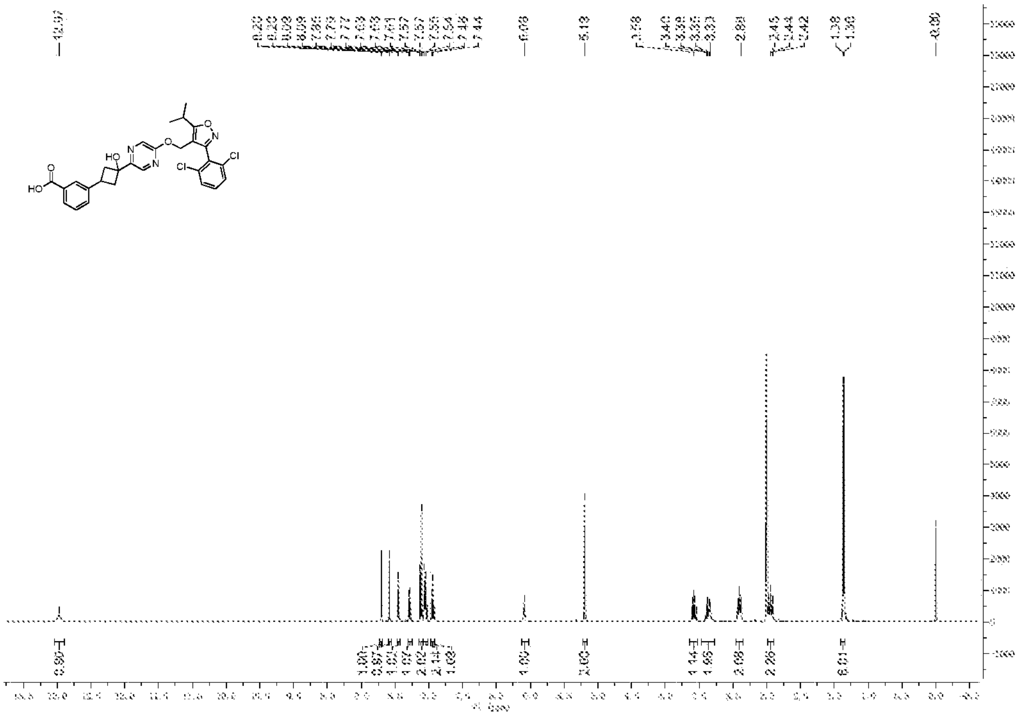
FIG. 12 is the $^1$H-NMR spectrogram of compound TM-6 of the present invention.

As shown in FIG. 12, $^1$H-NMR (400 MHz, DMSO-$D_6$): δ 12.97 (s, 1H), 8.20 (d, J=1.3 Hz, 1H), 8.09 (d, J=1.3 Hz, 1H), 7.95 (s, 1H), 7.79-7.77 (d, J=7.7 Hz, 1H), 7.63-7.61 (m, 2H), 7.55-7.53 (m, 2H), 7.44 (t, J=7.7 Hz, 1H), 6.09 (s, 1H), 5.19 (s, 2H), 3.61-3.54 (m, 1H), 3.42-3.33 (m, 1H), 2.90 (td, J=8.9, 2.5 Hz, 2H), 2.47-2.42 (m, 2H), 1.37 (d, J=7.0 Hz, 6H).

Figure 13:
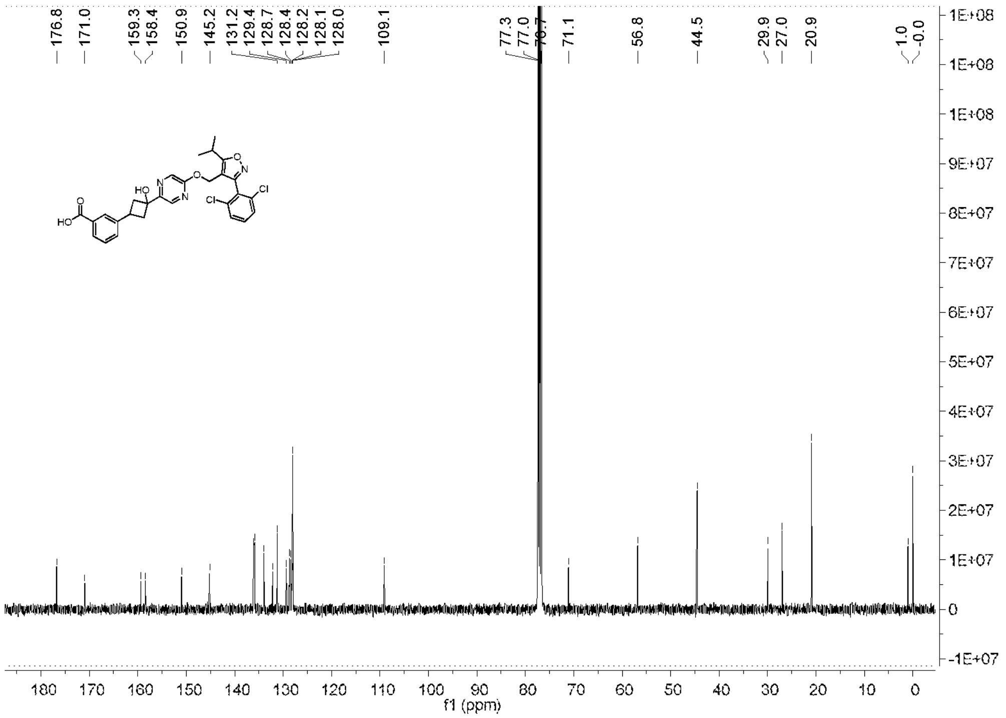
FIG. 13 is the 1$^3$C-NMR spectrogram of compound TM-6 of the present invention.

As shown in FIG. 13, 1$^3$C-NMR (100 MHz, CDCl3): 176.8, 171.0, 159.3, 158.4, 150.9, 145.2, 131.2, 129.4, 128.7, 128.4, 128.2, 128.1, 128.0, 109.1, 71.1, 56.8, 44.5, 29.9, 27.0, 20.9, 1.0.

Figure 14:
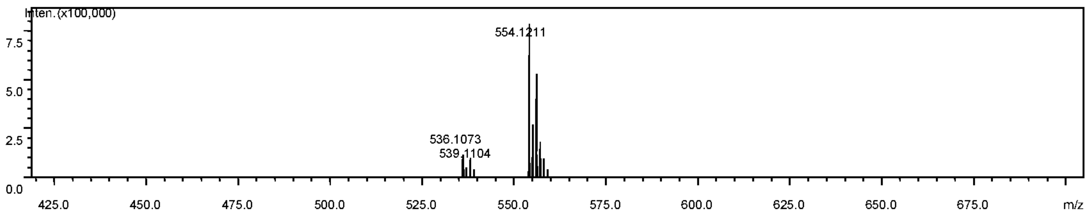
FIG. 14 is the mass spectrogram of compound TM-6 of the present invention.

As shown in FIG. 14, ESI-MS: m/z[M+H]+: Calcd. for $C_{28}H_{25}Cl_2N_3O_5$: 553.1171, Found: 554.1211.

Embodiment 7: Synthesis of Compound TM-7

Synthesis of 4-(5-bromopyrazine-2-ylmethoxy)-5-phenyl-3-(2, 6-dichlorophenyl) isoxazole

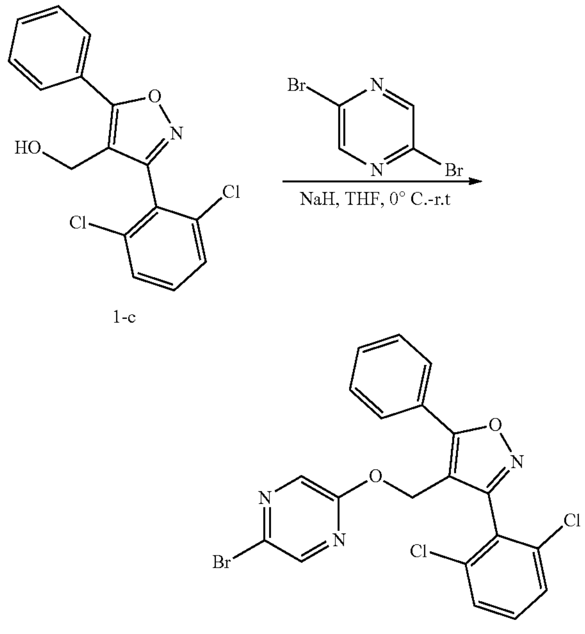

1-c 2-c

In a 100 mL round bottom flask, sodium hydride (60%, 0.83 g, 21 mmol) was placed, a small amount of petroleum ether was added, and the kerosene layer on the surface of the NaH was washed twice. 30 mL tetrahydrofuran was added and the reaction flask was cooled in a 0° C. ice bath. 2, 5-dibromopyrazine (833 mg, 3.5 mmol) was dissolved in 10 mL tetrahydrofuran and added dropwise to the round bottom flask with stirring. After the reaction for 20 min, 3-(2, 6-dichlorophenyl)-4-hydroxymethyl-5-phenylisoxazole (1.12 g, 3.5 mmol) was dissolved in 10 mL of tetrahydrofuran, and the mixture was slowly dropped into the reaction flask by the needle tube. The reaction was warmed to room temperature to react for 12 h. After the reaction, the reaction solution was poured into 100 mL of ice-water mixture, and then extracted with ethyl acetate (3×100 mL). The combined organic phase was washed with water and saturated salt solution and dried by anhydrous MgSO4. Separation and purification by silica gel column chromatography gradient elution (PE:EA=10:1, v/v) was performed to give a white solid (4-(5-bromopyrazine-2-ylmethoxy)-5-phenyl-3-(2, 6-dichlorophenyl) isoxazole), 752 mg, 45% yield.

Synthesis of 3-(3-(5-((3-(2, 6-dichlorophenyl)-5-phenylisoxazol-4-yl) methoxy) pyrazine-2-yl)-3-hydroxycyclobutyl) methyl benzoate

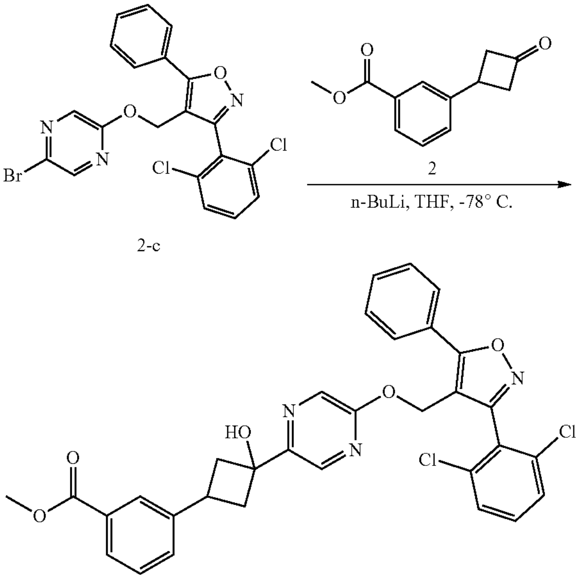

2-c

2

3-d

In a 100 mL three-necked flask under nitrogen protection, 4-(5-bromopyrazine-2-ylmethoxy)-5-phenyl-3-(2, 6-dichlorophenyl) isoxazole (1 g, 2.1 mmol) dissolved in anhydrous tetrahydrofuran (20 mL) was put into a reaction flask. Ethanol and liquid nitrogen were added into a 500 mL low temperature Dewar flask to reduce the temperature to −78° C. N-butyllithium solution (1.1N cyclohexane solution, 1.75 ml, 2.8 mmol) was added dropwise. After the mixture was stirred for 10 min, a solution of 3-(3-oxocyclobutanone) methyl benzoate (0.47 g, 2.3 mmol) dissolved in tetrahydrofuran (10 mL) was slowly added dropwise. The mixture was allowed to warm to room temperature to react overnight after reaction for 2 h at −78° C. After the reaction, the reaction solution was slowly poured into an ice-water mixture and extracted with ethyl acetate, with the ester layer washed with water (100 mL), dried over anhydrous magnesium sulfate, suction filtered, with the organic solvent distilled off under reduced pressure, and separated and purified by silica gel column chromatography gradient elution (PE: EA=10:1, v/v) to obtain 3-(3-(5-((3-(2, 6-dichlorophenyl)-5-phenylisoxazol-4-yl) methoxy) pyrazine-2-yl)-3-hydroxycyclobutyl) methyl benzoate as a white solid 329 mg, yield 26%.

Synthesis of 3-(3-(5-(5-phenyl-3-(2, isoxazole-4-ylmethoxy)-2-pyrazine)-1-hydroxycyclobutane) benzoic acid

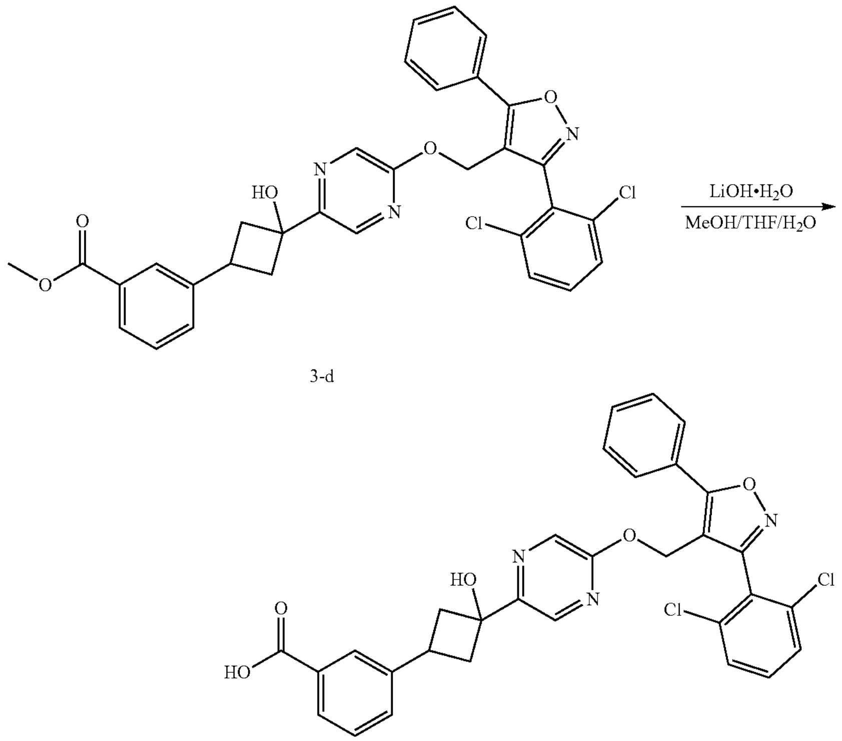

3-d

TM-7

3-(3-(5-((3-(2, 6-dichlorophenyl)-5-phenylisoxazol-4-yl) methoxy) pyrazine-2-yl)-3-hydroxycyclobutyl) methyl benzoate (118 mg, 0.2 mmol, 1 eq) was dissolved in 20 mL THF and a solution of LiOH·$H_2O$ (35 mg, 0.8 mmol, 4.2 eq) in water (5 mL) was added at 35° C. The mixture was stirred overnight. The organic solvent was removed by distillation under reduced pressure. The pH was adjusted to 5 with 1N hydrochloric acid. The mixture was extracted three times by adding ethyl acetate, dried with anhydrous magnesium sulfate, with the solvent removed by distillation under reduced pressure, and separated and purified by high-pressure preparative liquid chromatography. A Waters X Bridge C18 column (150 nm*4.6 nm*3.5 um) is used, with a mobile phase of acetonitrile and water, a flow rate of 18 mL/min, fractions collected with a gradient of 45%-75%, and most of the acetonitrile removed by concentrating. The mixture was treated by lyophilization with a lyophilizer to give 39 mg of (3-(3-(5-(5-phenyl-3-(2, 6-dichlorophenyl) isoxazole-4-yl-methoxy)-2-pyrazine)-1-hydroxycyclobutane) benzoic acid as a white powder solid, yield 33%.

Figure 15:
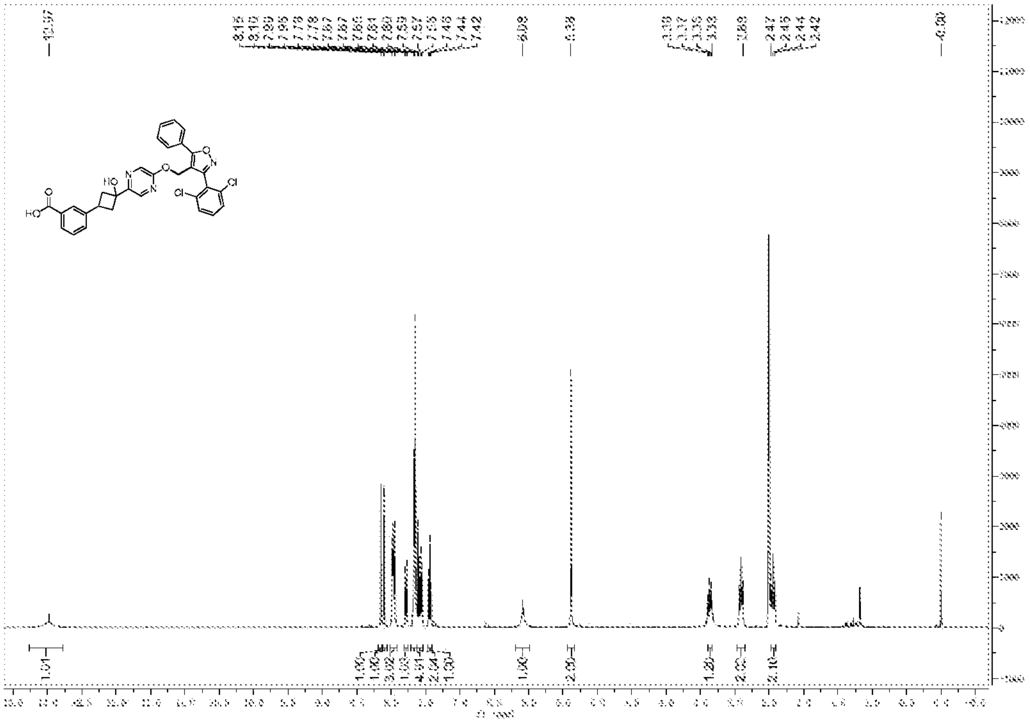
FIG. 15 is the $^1$H-NMR spectrogram of compound TM-7 of the present invention.

As shown in FIG. 15, $^{1}$H-NMR (400 MHz, DMSO-D6): δ 12.97 (s, 1H), 8.15 (d, J=1.3 Hz, 1H), 8.10 (d, J=1.3 Hz, 1H), 7.99-7.95 (m, J=16 Hz, 3H), 7.79-7.78 (d, J=4 Hz, 1H), 7.67-7.65 (m, J=8 Hz, 5H), 7.61-7.55 (m, J=8 Hz, 2H), 7.46-7.42 (m, 1H), 6.08 (s, 1H), 5.38 (s, 2H), 5.39-3.33 (m, 1H), 2.94-2.88 (m, 2H), 2.47-2.42 (m, 2H).

Figure 16:
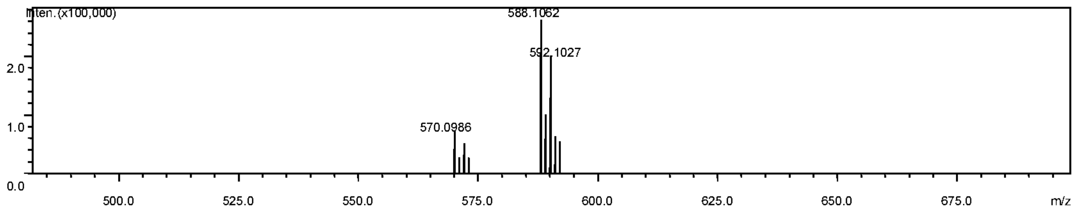
FIG. 16 is the mass spectrogram of compound TM-7 of the present invention.

As shown in FIG. 16, ESI-MS: m/z[M+H]+: Calcd. for $C_{31}H_{23}Cl_2N_3O_5$: 587.1015, Found: 588.1062.

Embodiment 8: Synthesis of Compound TM-8

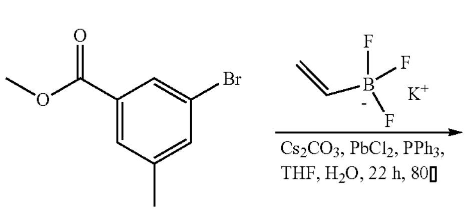

4a

-continued
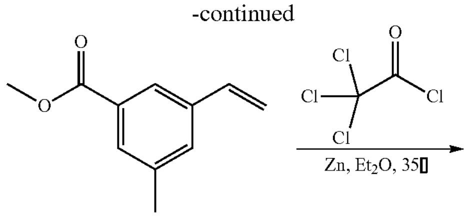
4b
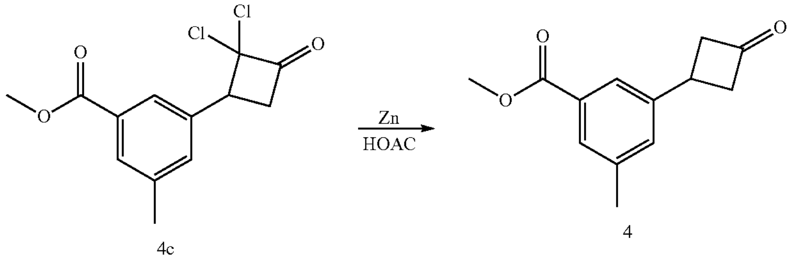
4c 4
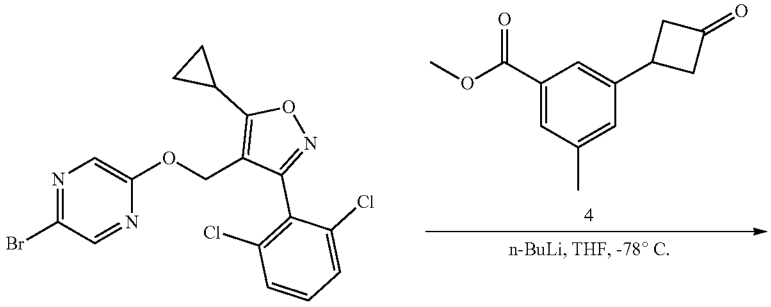
2-a
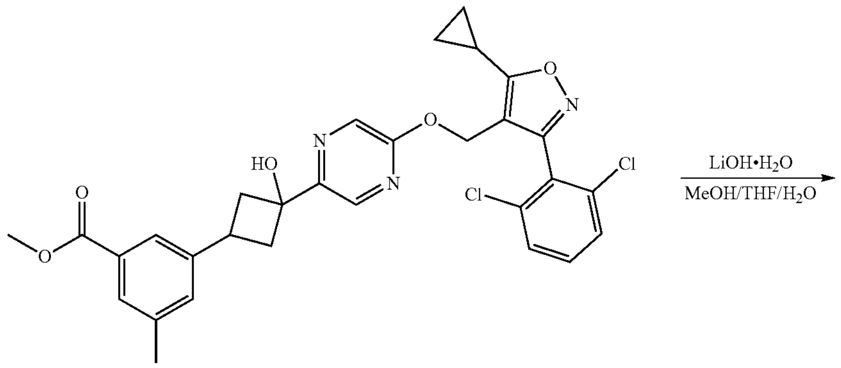
3-e
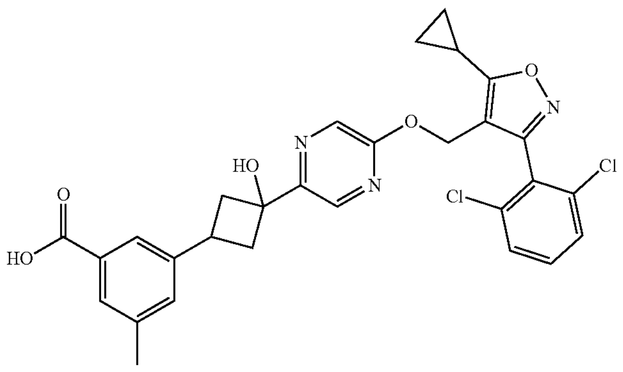
TM-8

3-methyl-5-methyl vinylbenzoate

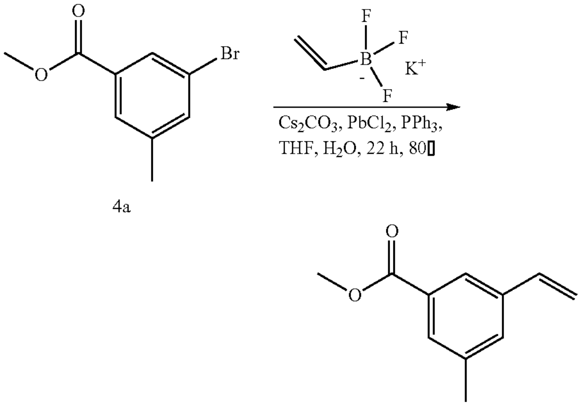

4a

4b

In a 100 mL round bottom flask, methyl 3-bromobenzoate (1.12 g, 5 mmol), potassium vinyltrifluoroborate (820 mg, 6.12 mmol), $PdCl_2$ (17.5 mg, 0.1 mmol), $PPh_3$ (80 mg, 0.3 mmol) and $Cs_2CO_3$ (5 g, 15 mmol) were added, followed by THF (18 mL) and $H_2O$ (2 mL) under $N_2$. The mixture was stirred at 80° C. for 22 h, and then cooled to room temperature, washed with water, dried over anhydrous magnesium sulfate and suction filtered, distillation under reduced pressure. Separation and purification by silica gel column chromatography gradient elution (PE:EA=60:1, v/v) was performed to give a pale pink oily liquid (3-methyl-5-methyl vinylbenzoate) 164 mg, yield 30%.

3-(2, 2-dichloro-3-oxocyclobutanone)-5-methyltoluate

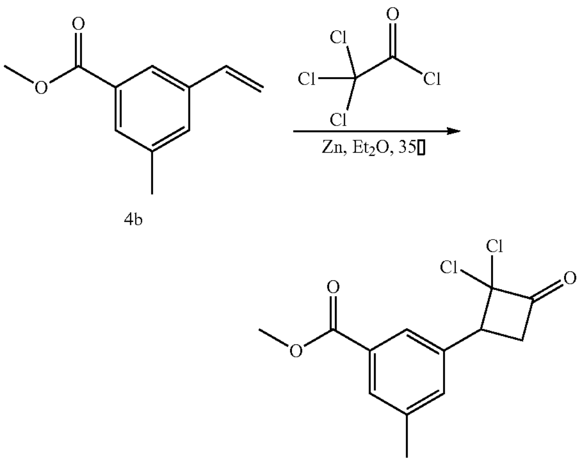

4b

4c 3-methyl-5-methyl vinylbenzoate (5.46 g, 31 mmol, 1 eq) was dissolved in diethyl ether (150 mL) under nitrogen protection. Zinc dust (6 g, 93 mmol, 3 eq) was added. After sonication for 30 min, a solution of trichloroacetyl chloride (8.7 mL, 77.5 mmol, 2.5 eq) in $Et_2O$ (50 mL) was added dropwise, with sonication continued for 30 min. The mixture was heated to 35° C. Sonication was continued for 2.5 h. After the reaction, it was cooled to room temperature and quenched by slowly dropwise addition of water (50 mL). The mixture was poured into water, stirred for 20 min, filtered, and rinsed with $Et_2O$. The organic layer was washed with water (250 mL), saturated sodium bicarbonate (250 mL) and saturated sodium chloride (250 mL), dried over anhydrous magnesium sulfate, filtered, with the solvent distilled off under reduced pressure to give the crude product as a yellow oil. Separation and purification by silica gel column chromatography gradient elution (PE:EA=50:1, v/v) was performed to give 3-(2, 2-dichloro-3-oxocyclobutanone)-5-methyltoluate as a yellow oily liquid 3.56 g, yield 40%.

3-methyl-5-(3-oxocyclobutyl) methyl benzoate

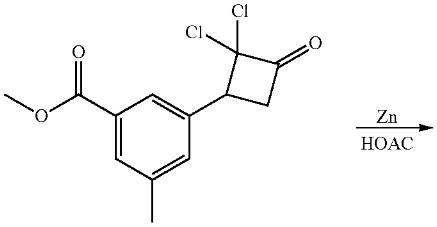

4c

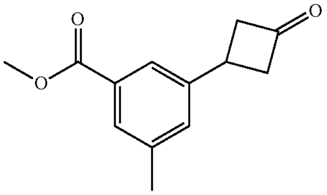

4

3-(2, 2-dichloro-3-oxocyclobutanone)-5-methyltoluate (2.79 g, 9.7 mmol, 1 eq) combined with zinc dust (2.54 g, 38.8 mmol, 4 eq) was dissolved in 60 mL acetic acid and the mixture was stirred at room temperature for 1 h. It was then refluxed for 3.5 h at 80° C. in an oil bath and cooled to room temperature after the reaction.

The solvent acetic acid was diluted with 100 mL of water and extracted with diethyl ether (3×40 mL). The combined organic phases were washed sequentially with saturated sodium carbonate solution (3×40 mL), water (100 mL), and saturated salt solution (100 mL). The drying was carried out with an amount of anhydrous $MgSO_4$. Separation and purification by silica gel column chromatography gradient elution (PE:EA=50:1, v/v) was performed to give the compound (3-(3-oxocyclobutanone) methyl benzoate) 1.38 g, yield 65%.

Synthesis of 3-(3-(5-((5-cyclopropyl-3-(2, 6-dichlorophenyl) isoxazol-4-yl) methoxy) pyrazine-2-yl)-3-hydroxycyclobutyl)-5-methyltoluate

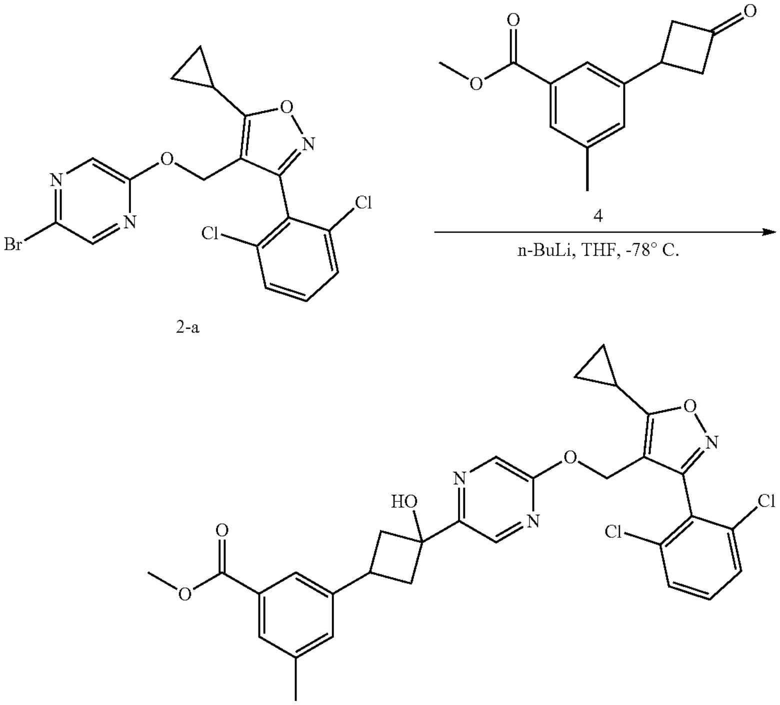

2-a 3-e

In a 100 ml three-necked flask under nitrogen protection, 4-(5-bromopyrazine-2-ylmethoxy)-5-cyclopropyl-3-(2, 6-dichlorophenyl) isoxazole (1.02 g, 2.3 mmol) dissolved in anhydrous tetrahydrofuran (20 mL) was put into a reaction flask. Ethanol and liquid nitrogen were added into a 500 mL low-temperature Dewar flask to reduce the temperature to −78° C. N-butyllithium (1.7 ml, 2.7 mmol) was slowly added dropwise, and the mixture was stirred for 10 min. A solution of 3-methyl-5-(3-oxocyclobutyl) methyl benzoate (0.55 g, 2.5 mmol) dissolved in tetrahydrofuran (10 mL) was slowly added dropwise. The mixture was allowed to warm to room temperature to react overnight after reaction for 2 h at −78° C. After the reaction, the reaction solution was slowly poured into an ice-water mixture and extracted with ethyl acetate, with the ester layer washed with water (100 mL), dried over anhydrous magnesium sulfate, suction filtered, with the organic solvent distilled off under reduced pressure, and separated and purified by silica gel column chromatography gradient elution (PE:EA=10:1, v/v) to obtain 3-(3-(5-((5-cyclopropyl-3-(2, 6-dichlorophenyl) isoxazol-4-yl) methoxy) pyrazine-2-yl)-3-hydroxycyclobutyl)-5-methyltoluate as a white solid, 47% yield.

3-(3-(5-((5-cyclopropyl-3-(2, 6-dichlorophenyl) isoxazol-4-yl) methoxy) pyrazine-2-yl)-3-hydroxycyclobutyl)-5-methyl benzoic acid

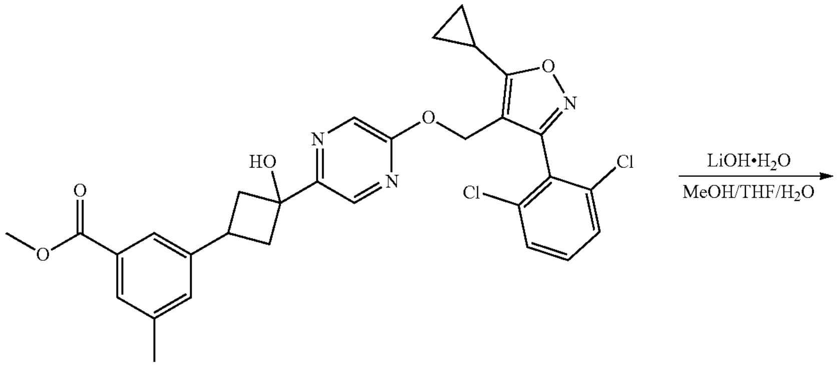

3-e

-continued

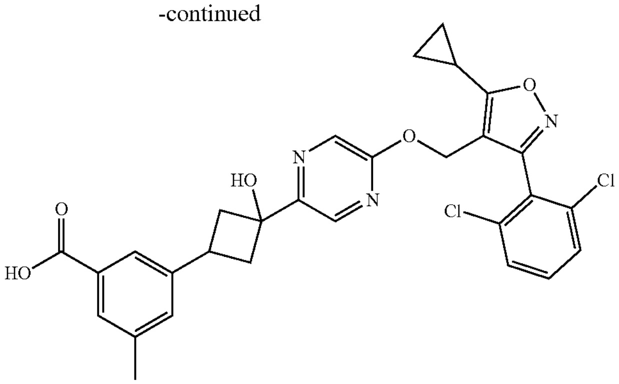

TM-8

3-(3-(5-((3-(2, 6-dichlorophenyl)-5-isopropylisoxazol-4-yl) methoxy) pyrazine-2-yl)-3-hydroxycyclobutyl)-5-methyl benzoate (116 mg, 0.2 mmol, 1 eq) was dissolved in 20 mL THF and a solution of $LiOH{\cdot}H_2O$ (35 mg, 0.8 mmol, 4.2 eq) in water (5 mL) was added at 35° C. The mixture was stirred overnight. The organic solvent was removed by distillation under reduced pressure. The pH was adjusted to 5 with 1N hydrochloric acid. The mixture was extracted three times by adding ethyl acetate, dried with anhydrous magnesium sulfate, with the solvent removed by distillation under reduced pressure, and separated and purified by high-pressure preparative liquid chromatography. A Waters X Bridge C18 column (150 nm*4.6 nm*3.5 um) is used, with a mobile phase of acetonitrile and water, a flow rate of 18 mL/min, fractions collected with a gradient of 45%-75%, and most of the acetonitrile removed by concentrating. The mixture was treated by lyophilization with a lyophilizer to give 3-(3-(5-((5-cyclopropyl-3-(2, 6-dichlorophenyl) isoxazol-4-yl) methoxy) pyrazine-2-yl)-3-hydroxycyclobutyl)-5-methyl benzoic acid as a white powder solid, 37 mg, yield 33%.

Figure 17:
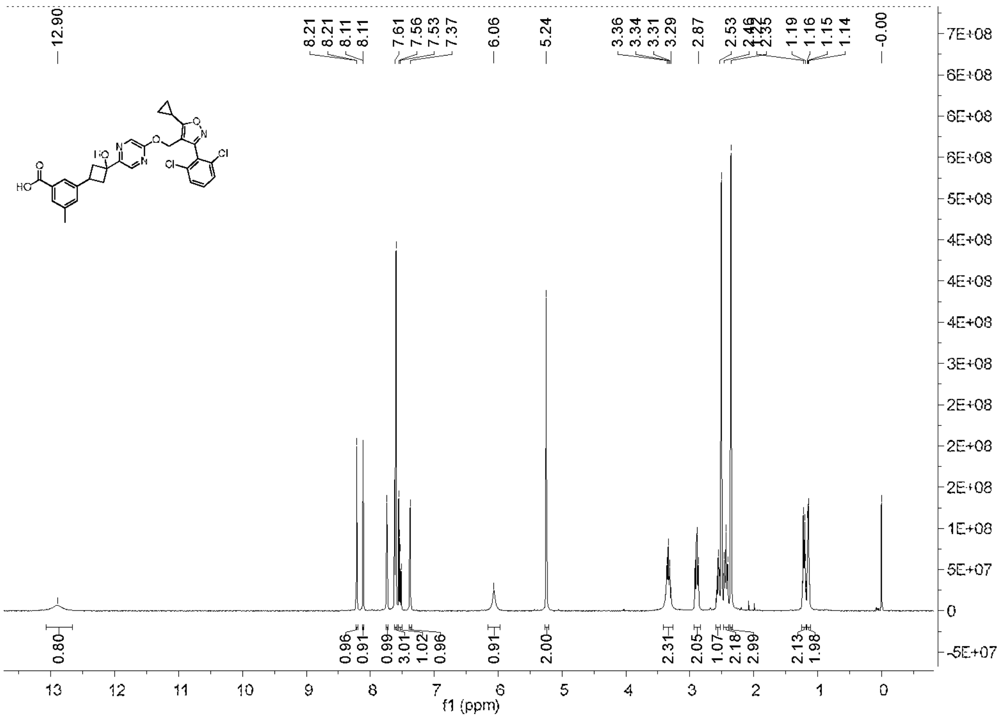
FIG. 17 is the $^1$H-NMR spectrogram of compound TM-8 of the present invention.

As shown in FIG. 17, $^1$H-NMR (400 MHz, DMSO-D6): δ 12.90 (1H, s), 8.21 (1H, d, J=1.2 Hz), 8.11 (1H, d, J=1.2 Hz), 7.74 (1H, s), 7.62-7.60 (3H, m), 7.56-7.52 (1H, m), 7.37 (1H, s), 6.06 (1H, s), 5.24 (2H, s), 3.38-3.29 (1H, m), 2.92-2.87 (2H, m), 2.59-2.53 (1H, m), 2.46-2.41 (2H, m), 2.35 (3H, s), 1.24-1.18 (2H, m), 1.16-1.14 (2H, m).

Figure 18:
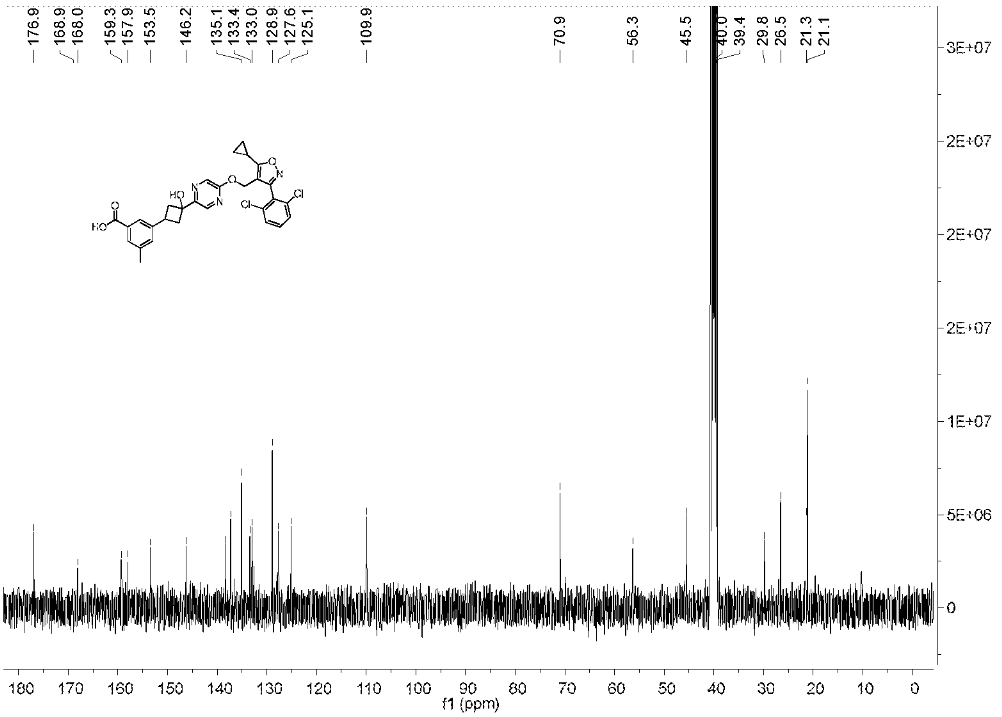
FIG. 18 is the $1^3$C-NMR spectrogram of compound TM-8 of the present invention.

As shown in FIG. 18, $1^3$C-NMR (400 MHz, DMSO-D6): δ 176.9, 168.9, 168.0, 159.3, 157.9, 153.5, 146.2, 135.1, 133.4, 133.0, 128.9, 127.6, 125.1, 109.9, 70.9, 56.3, 45.5, 29.8, 26.5, 21.3, 21.1.

Figure 19:
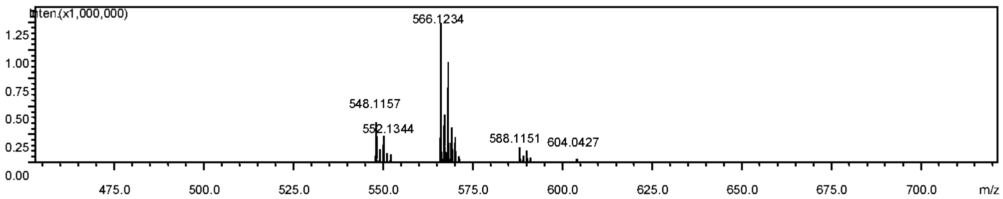
FIG. 19 is the mass spectrogram of compound TM-8 of the present invention.

As shown in FIG. 19, ESI-MS: m/z[M+H]+: Calcd. for $C_{29}H_{25}Cl_2N_3O_5$: 565.1171, Found: 566.1234.

Embodiment 9: Synthesis of Compound TM-9

Synthesis of 3-(3-(5-((3-(2, 6-dichlorophenyl)-5-isopropylisoxazol-4-yl) methoxy) pyrazine-2-yl)-3-hydroxycyclobutyl)-5-methyl toluate

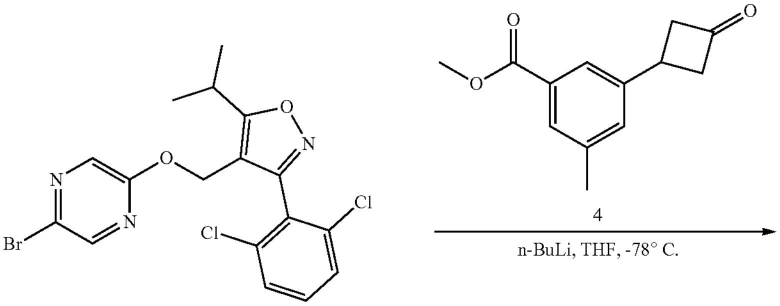

2-b

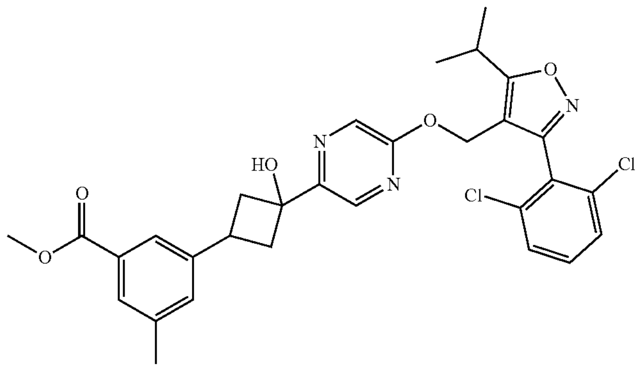

3-f

In a 100 ml three-necked flask under nitrogen protection, 4-(5-bromopyrazine-2-ylmethoxy)-5-phenyl-3-(2, 6-dichlorophenyl) isoxazole (1.02 g, 2.3 mmol) dissolved in anhydrous tetrahydrofuran (20 mL) was put into a reaction flask. Ethanol and liquid nitrogen were added into a 500 mL low-temperature Dewar flask to reduce the temperature to −78° C. N-butyllithium (1.7 ml, 2.7 mmol) was slowly added dropwise, and the mixture was stirred for 10 min. A solution of 3-methyl-5-(3-oxocyclobutyl) methyl benzoate (0.55 g, 2.5 mmol) dissolved in tetrahydrofuran (10 mL) was slowly added dropwise. The mixture was allowed to warm to room temperature to react overnight after reaction for 2 h at −78° C. After the reaction, the reaction solution was slowly poured into an ice-water mixture and extracted with ethyl acetate, with the ester layer washed with water (100 mL), dried over anhydrous magnesium sulfate, suction filtered, with the organic solvent distilled off under reduced pressure, and separated and purified by silica gel column chromatography gradient elution (PE:EA=10 1, v/v, PE is petroleum ether, EA is ethyl acetate) to give a white solid (3-(3-(5-((3-(2, 6-dichlorophenyl)-5-isopropylisoxazol-4-yl) methoxy) pyrazine-2-yl)-3-hydroxycyclobutyl)-5-methyl toluate), 643 mg, yield 48%.

Synthesis of 3-(3-(5-((3-(2, 6-dichlorophenyl)-5-isopropylisoxazol-4-yl) methoxy) pyrazine-2-yl)-3-hydroxycyclobutyl)-5-methyl benzoic acid 3-(3-(5-((3-(2, 6-dichlorophenyl)-5-cyclopropylisoxazol-4-yl) methoxy) pyrazine-2-yl)-3-hydroxycyclobutyl) methyl toluate (117 mg, 0.2 mmol, 1 eq) was dissolved in 20 mL THF and a solution of $LiOH{\cdot}H_2O$ (35 mg, 0.8 mmol, 4.2 eq) in water (5 mL) was added at 35° C. The mixture was stirred overnight. The organic solvent was removed by distillation under reduced pressure. The pH was adjusted to 5 with 1N hydrochloric acid. The mixture was extracted three times by adding ethyl acetate, dried with anhydrous magnesium sulfate, with the solvent removed by distillation under reduced pressure, and separated and purified by high-pressure preparative liquid chromatography. A Waters X Bridge C18 column (150 nm*4.6 nm*3.5 um) is used, with a mobile phase of acetonitrile and water, a flow rate of 18 mL/min, fractions collected with a gradient of 45%-75%, and most of the acetonitrile removed by concentrating. The mixture was treated by lyophilization with a lyophilizer to give a white powdery solid (3-(3-(5-((3-(2, 6-dichlorophenyl)-5-isopropylisoxazol-4-yl) methoxy) pyrazine-2-yl)-3-hydroxycyclobutyl)-5-methyl benzoic acid), 46 mg, yield 40%.

Figure 20:
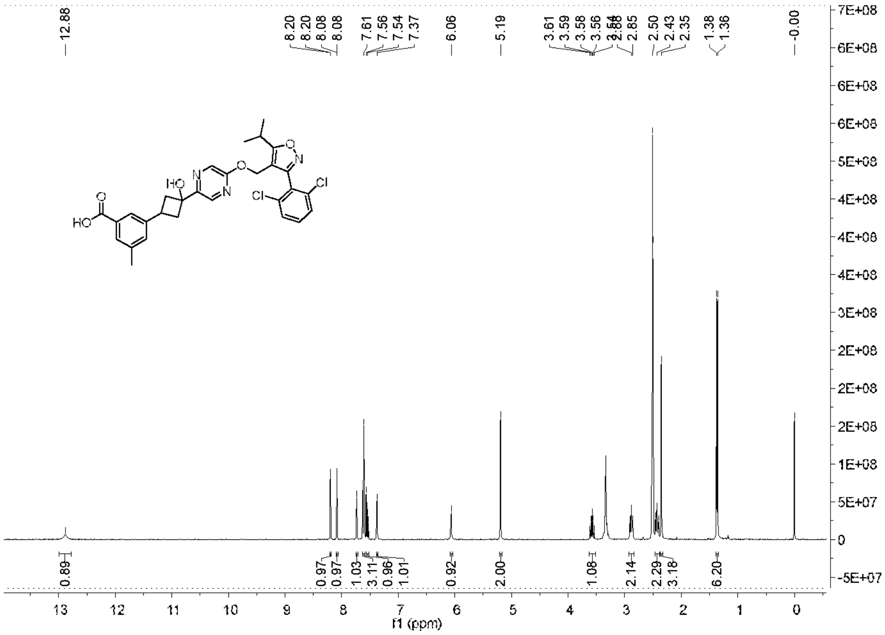
FIG. 20 is the $^1$H-NMR spectrogram of compound TM-9 of the present invention.

As shown in FIG. 20, $^1$H-NMR (400 MHz, DMSO-D6): δ 12.88 (1H, brs), 8.20 (1H, d, J=1.2 Hz), 8.08 (1H, d, J=1.2 Hz), 7.73 (1H, s), 7.63-7.60 (3H, m), 7.56-7.52 (1H, s), 7.37 (1H, s), 6.06 (1H, brs), 5.19 (2H, s), 3.61-3.54 (1H, m), 2.91-2.85 (2H, m), 2.45-2.40 (2H, m), 2.35 (3H, s), 1.38-1.36 (6H, d, J=8 Hz).

Figure 21:
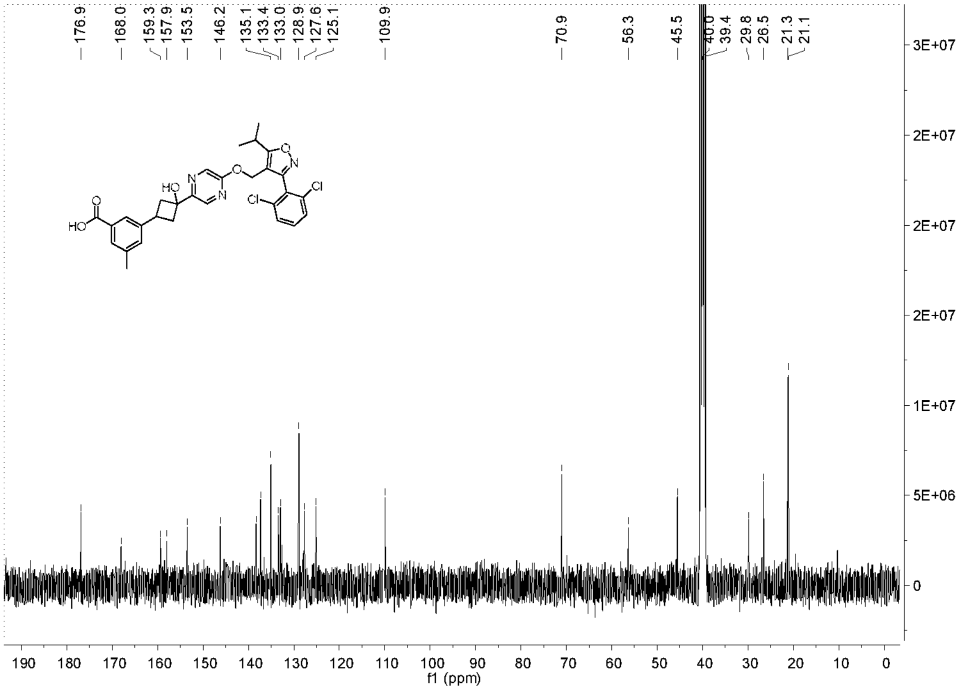
FIG. 21 is the $1^3$C-NMR spectrogram of compound TM-9 of the present invention.

As shown in FIG. 21, $1^3$C-NMR (100 MHz, DMSO-D6): 176.9, 168.0, 159.3, 157.9, 153.5, 146.2, 135.1, 133.4, 133.0, 128.9, 127.6, 125.1, 109.9, 70.9, 56.3, 45.5, 29.8, 26.5, 21.3, 21.1.

Figure 22:
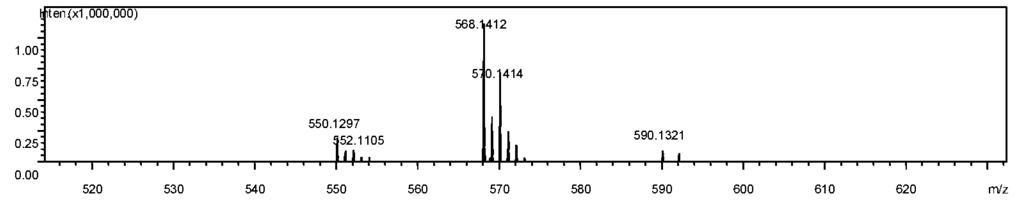
FIG. 22 is the mass spectrogram of compound TM-9 of the present invention.

As shown in FIG. 22, ESI-MS: m/z[M+H]+: Calcd. for $C_{29}H_{27}Cl_2N_3O_5$: 567.1328, Found: 568.1412.

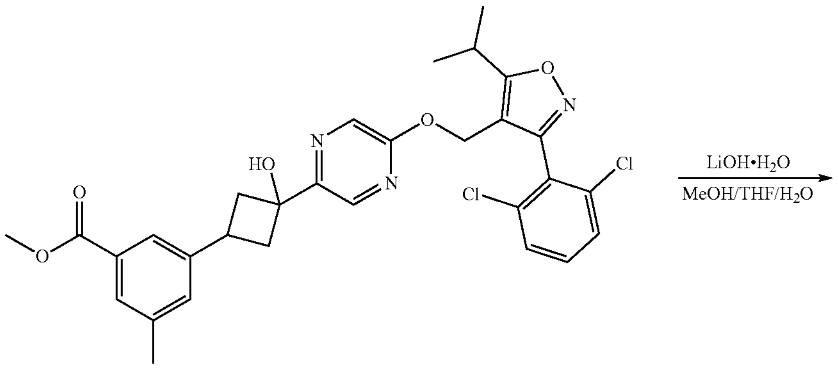

3-f

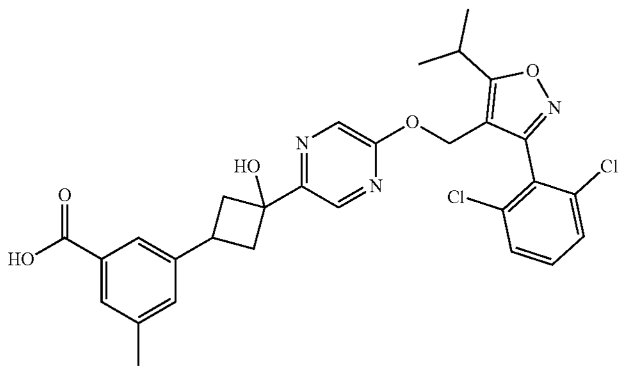

TM-9

Embodiment 10: Synthesis of Compound TM-10

Synthesis of 3-(3-(5-((3-(2, 6-dichlorophenyl)-5-phenylisoxazol-4-yl) methoxy) pyrazine-2-yl)-3-hydroxycyclobutyl)-5-methyl toluate

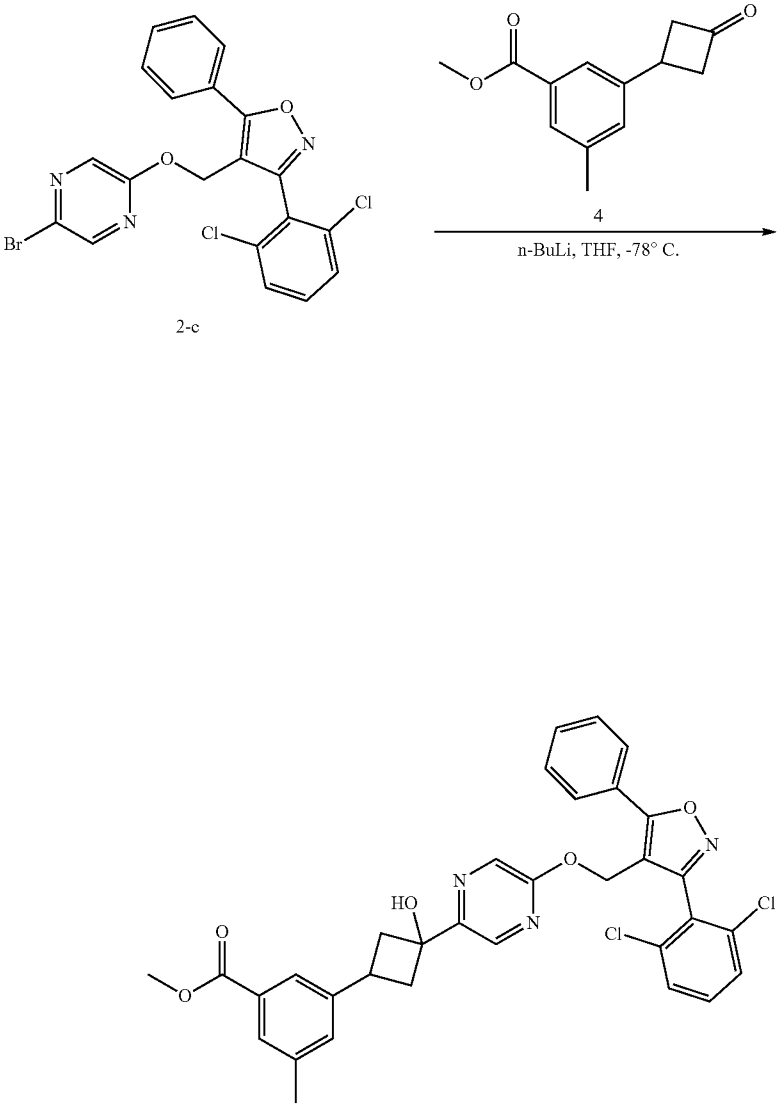

3-g

In a 100 ml three-necked flask under nitrogen protection, 4-(5-bromopyrazine-2-ylmethoxy)-5-phenyl-3-(2, 6-dichlorophenyl) isoxazole (1.03 g, 2.3 mmol) dissolved in anhydrous tetrahydrofuran (20 mL) was put into a reaction flask. Ethanol and liquid nitrogen were added into a 500 mL low-temperature Dewar flask to reduce the temperature to −78° C. N-butyllithium (1.7 ml, 2.7 mmol) was slowly added dropwise, and the mixture was stirred for 10 min. A solution of 3-methyl-5-(3-oxocyclobutyl) methyl benzoate (0.55 g, 2.5 mmol) dissolved in tetrahydrofuran (10 mL) was slowly added dropwise. The mixture was allowed to warm to room temperature to react overnight after reaction for 2 h at −78° C. After the reaction, the reaction solution was slowly poured into an ice-water mixture and extracted with ethyl acetate, with the ester layer washed with water (100 mL), dried over anhydrous magnesium sulfate, suction filtered, with the organic solvent distilled off under reduced pressure, and separated and purified by silica gel column chromatography gradient elution (PE:EA=10:1, v/v) to obtain a white solid (3-(3-(5-((3-(2, 6-dichlorophenyl)-5-phenylisoxazol-4-yl) methoxy) pyrazine-2-yl)-3-hydroxycyclobutyl)-5-methyl toluate) 496 mg, 35% yield.

Synthesis of 3-(3-(5-((3-(2, 6-dichlorophenyl)-5-phenylisoxazol-4-yl) methoxy) pyrazine-2-yl)-3-hydroxycyclobutyl)-5-methyl benzoic acid

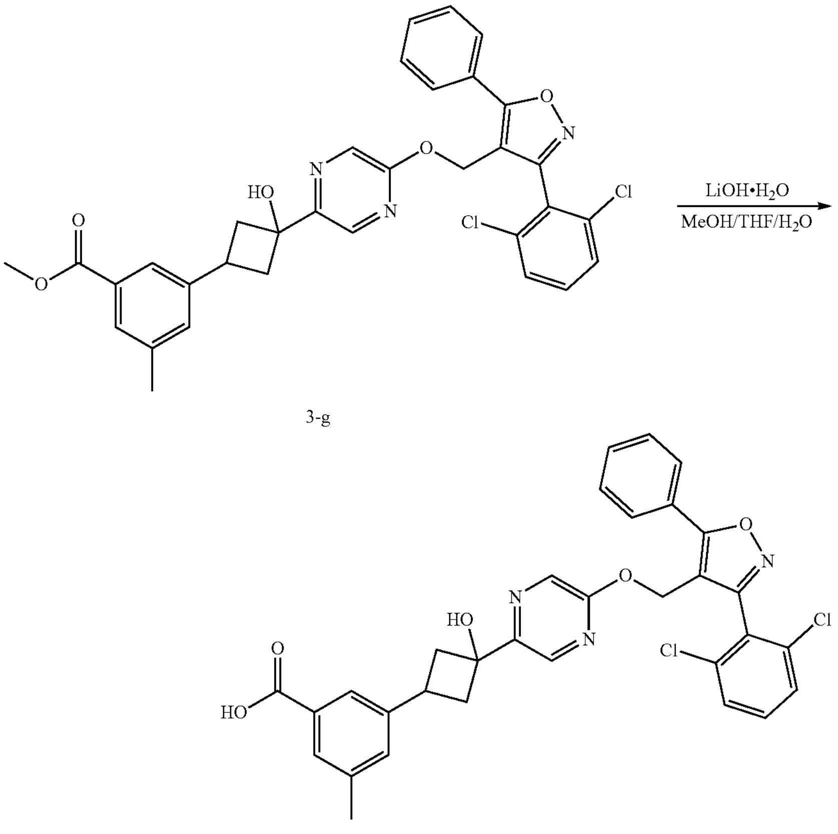

3-g

TM-10

3-(3-(5-((3-(2, 6-dichlorophenyl)-5-phenylisoxazol-4-yl) methoxy) pyrazine-2-yl)-3-hydroxycyclobutyl)-5-methyl toluate (123 mg, 0.2 mmol, 1 eq) was dissolved in 20 mL THF and a solution of LiOH·$H_2O$ (35 mg, 0.8 mmol, 4.2 eq) in water (5 mL) was added at 35° C. The mixture was stirred overnight. The organic solvent was removed by distillation under reduced pressure. The pH was adjusted to 5 with 1N hydrochloric acid. The mixture was extracted three times by adding ethyl acetate, dried with anhydrous magnesium sulfate, with the solvent removed by distillation under reduced pressure, and separated and purified by high-pressure preparative liquid chromatography. A Waters X Bridge C18 column (150 nm*4.6 nm*3.5 um) is used, with a mobile phase of acetonitrile and water, a flow rate of 18 mL/min, fractions collected with a gradient of 45%-75%, and most of the acetonitrile removed by concentrating. The mixture was treated by lyophilization with a lyophilizer to give a white powdery solid (3-(3-(5-((3-(2, 6-dichlorophenyl)-5-phenylisoxazol-4-yl) methoxy) pyrazine-2-yl)-3-hydroxycyclobutyl)-5-methyl benzoic acid), 37 mg, yield 31%.

Figure 23:
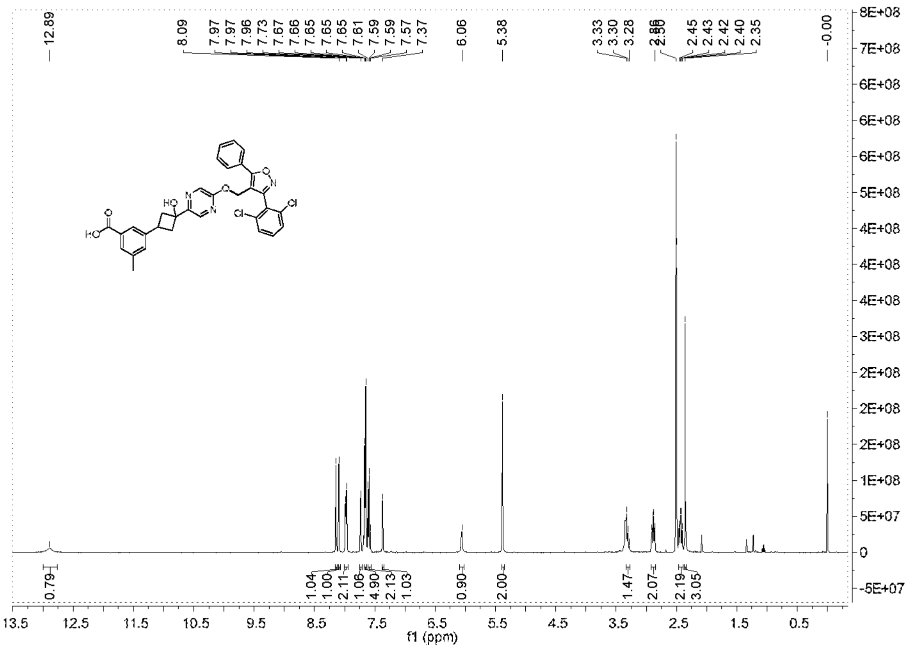
FIG. 23 is the $^1$H-NMR spectrogram of compound TM-10 of the present invention.

As shown in FIG. 23, $^1$H-NMR (400 MHz, DMSO-D6): δ 12.89 (1H, s), 8.14 (1H, d, J=1.6 Hz), 8.09 (1H, d, J=1.6 Hz), 7.99-7.96 (3H, m), 7.73 (1H, s), 7.67-7.65 (5H, m), 7.61-7.57 (2H, m), 7.37 (1H, s), 6.06 (1H, s), 5.38 (2H, s), 3.33-3.28 (1H, m), 2.91-2.86 (2H, m), 2.45-2.40 (2H, m), 2.35 (3H, s).

Figure 24:
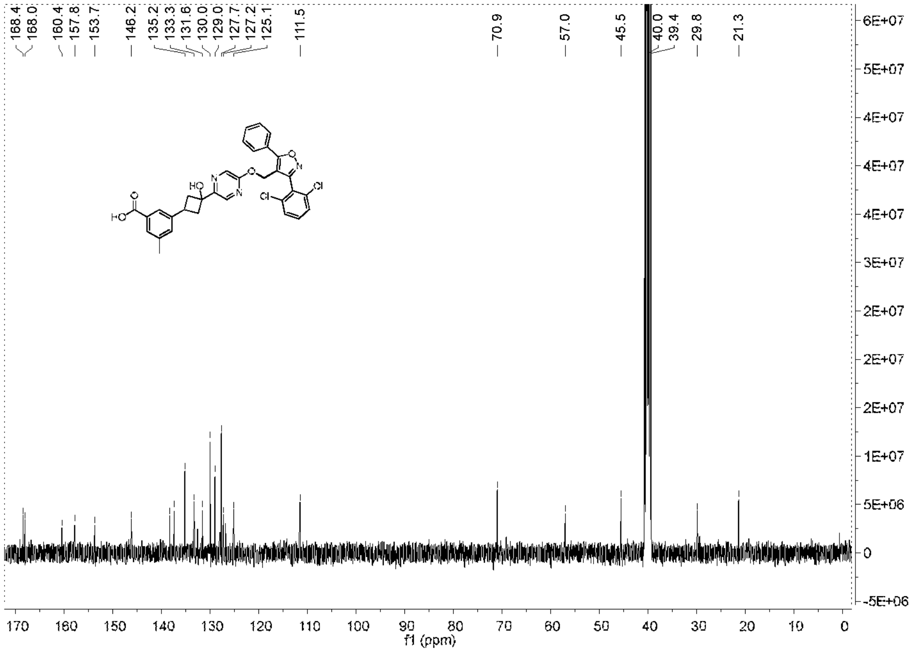
FIG. 24 is the $1^3$C-NMR spectrogram of compound TM-10 of the present invention.

As shown in FIG. 24, 1$^3$C-NMR (100 MHz, DMSO-D6): 168.4, 168.0, 160.4, 157.8, 153.7, 146.2, 135.2, 133.3, 131.6, 130.0, 129.0, 127.7, 127.2, 125.1, 111.5, 70.9, 57.0, 45.5, 29.8, 21.3.

Figure 25:
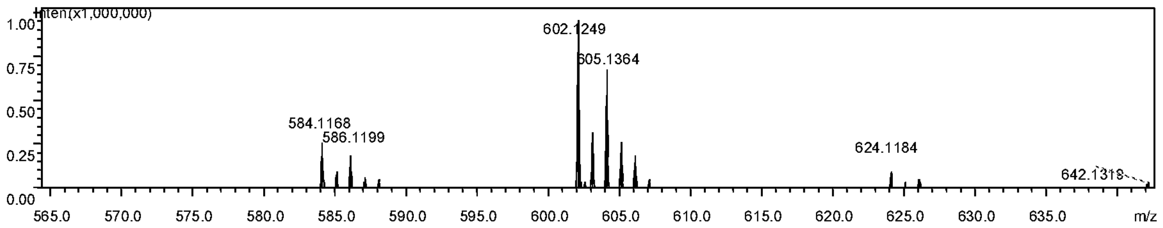
FIG. 25 is the mass spectrogram of compound TM-10 of the present invention.

As shown in FIG. 25, ESI-MS: m/z[M+H]+: Calcd. for $C_{32}H_{25}Cl_2N_3O_5$: 601.1171, Found: 602.1249.

The invention claimed is:

1. A compound having the structure of Formula (I):

Formula (I)

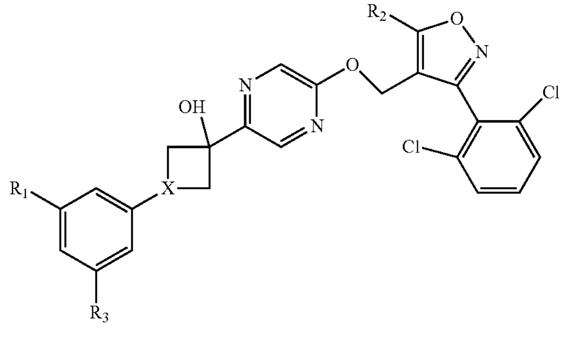

wherein $R_1$ is halogen, —COOH,

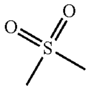 or 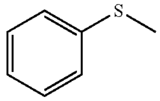 ;

$R_2$ is $C_1$-$C_6$ alkyl, cyclic hydrocarbyl, aryl, substituted alkyl, or substituted aryl;

$R_3$ is —H, $C_1$-$C_3$ alkyl, cyclic hydrocarbyl, or substituted alkyl; and,

X is C or N, or a hydrate, a solvate, a pharmaceutically acceptable salt, or a resolved single isomer thereof.

2. The compound according to claim 1, wherein $R_1$ is —Br;

$R_2$ is $C_1$-$C_3$ alkyl or cyclic hydrocarbyl;

$R_3$ is —$CH_3$.

3. The compound according to claim 1, wherein $R_2$ is

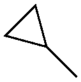 , 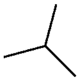 or 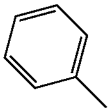 .

4. The compound according to claim 1, wherein said compound is

TM-1

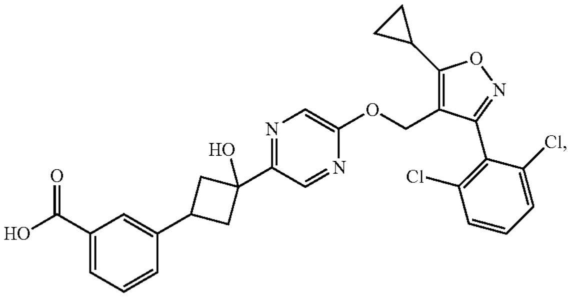

TM-2

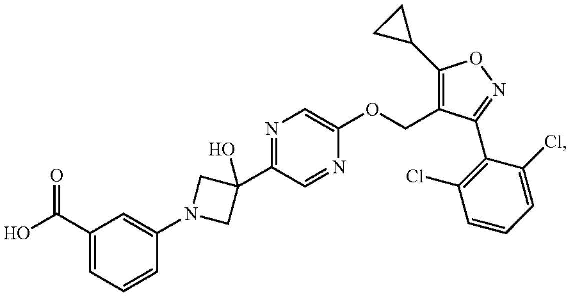

-continued

TM-3

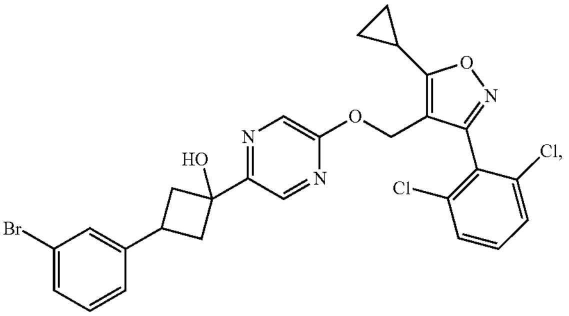

TM-4

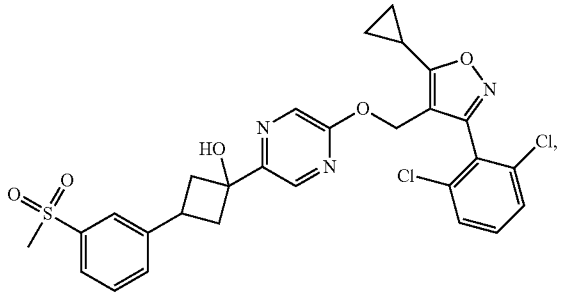

TM-5

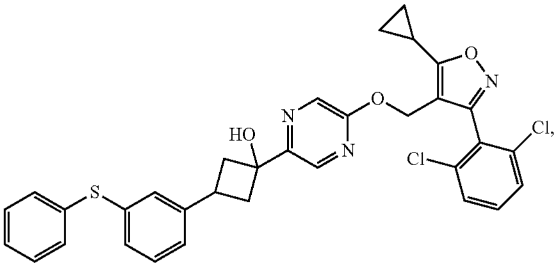

TM-6

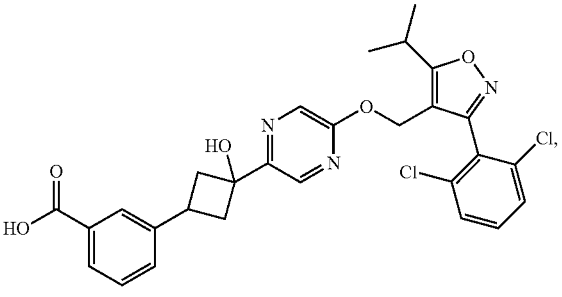

TM-7

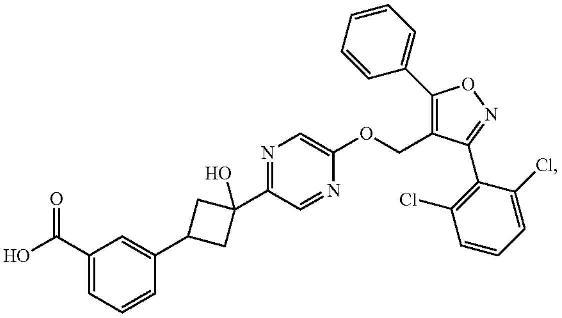

-continued

TM-8

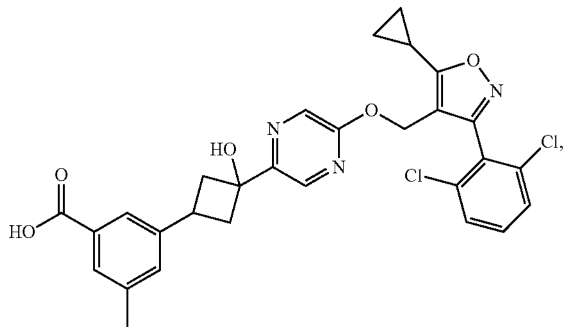

TM-9

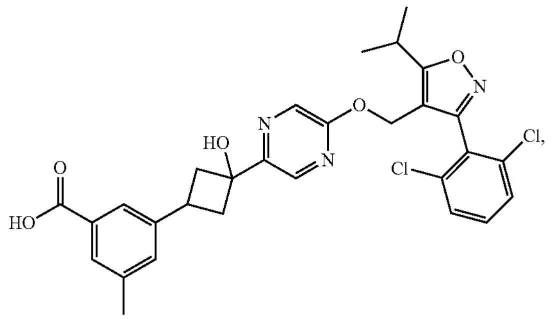

or

TM-10

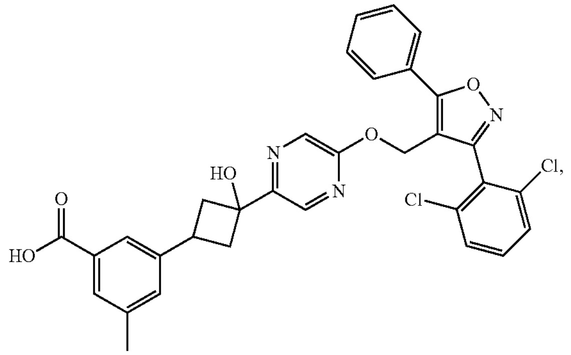

or a pharmaceutically acceptable salt thereof.

5. A pharmaceutical composition comprising a compound or a pharmaceutically acceptable salt thereof according to claim 1 as an active ingredient.

6. The pharmaceutical composition according to claim 5, further comprising a pharmaceutically acceptable carrier.

7. A method for preparing a compound according to claim 1, comprising Scheme 1:

Scheme 1

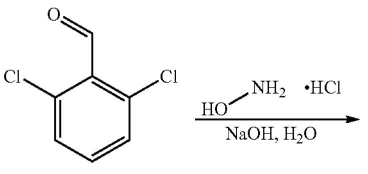

1a

-continued

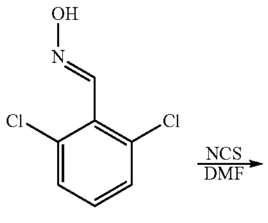

1b

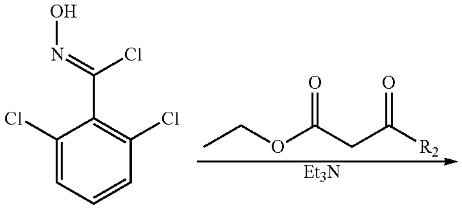

1c

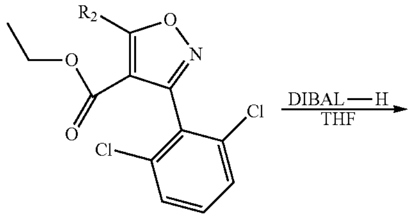

1d~1f

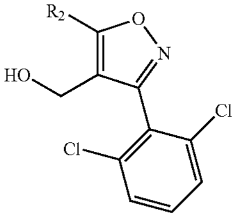

1-a~1-c

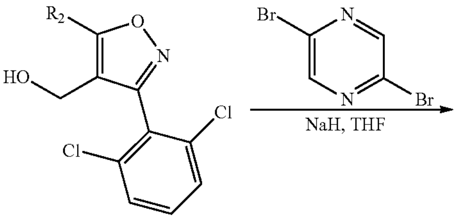

1-a~1-c

-continued

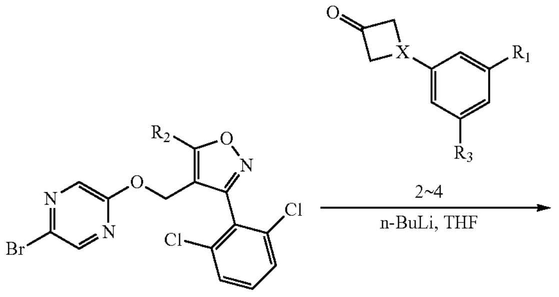

2-a~2-c

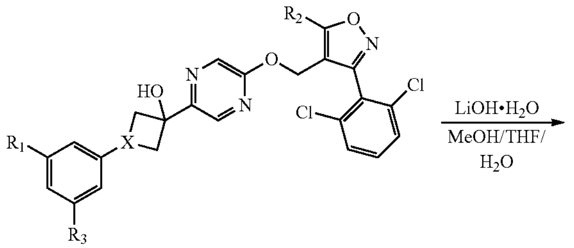

3-a~3-g

-continued

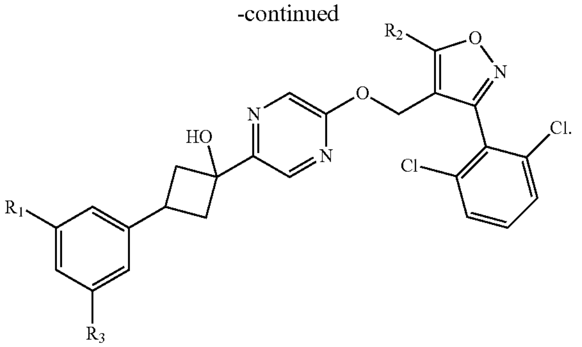

TM

8. A method for treating non-alcoholic fatty liver disease comprising administering to a subject in need thereof a compound according to claim 1.

9. The method according to claim 8, wherein the non-alcoholic fatty liver disease is non-alcoholic steatohepatitis.

10. A method for treating non-alcoholic fatty liver disease comprising administering to a subject in need thereof the pharmaceutical composition according to claim 5.

11. The method according to claim 10, wherein the non-alcoholic fatty liver disease is non-alcoholic steatohepatitis.

* * * * *